(12) United States Patent
Kellar et al.

(10) Patent No.: US 8,308,812 B2
(45) Date of Patent: Nov. 13, 2012

(54) PROSTHETIC JOINT ASSEMBLY AND JOINT MEMBER THEREFOR

(75) Inventors: Franz W. Kellar, Gastonia, NC (US); Harold Lloyd Crowder, Jr., Concord, NC (US); Scott M. Duquette, Clemmons, NC (US)

(73) Assignee: BioMedFlex, LLC, Gastonia, NC (US)

( * ) Notice: Subject to any disclaimer, the term of this patent is extended or adjusted under 35 U.S.C. 154(b) by 0 days.

(21) Appl. No.: 13/342,584

(22) Filed: Jan. 3, 2012

(65) Prior Publication Data
US 2012/0095569 A1    Apr. 19, 2012

Related U.S. Application Data

(63) Continuation-in-part of application No. 13/311,119, filed on Dec. 5, 2011, which is a continuation of application No. 13/073,963, filed on Mar. 28, 2011, now Pat. No. 8,070,823, which is a continuation-in-part of application No. 12/826,620, filed on Jun. 29, 2010, now Pat. No. 7,914,580, which is a continuation-in-part of application No. 12/714,288, filed on Feb. 26, 2010, now Pat. No. 7,905,919, which is a continuation-in-part of application No. 11/936,601, filed on Nov. 7, 2007.

(60) Provisional application No. 60/864,667, filed on Nov. 7, 2006.

(51) Int. Cl.
*A61F 2/30* (2006.01)
*A61F 2/32* (2006.01)

(52) U.S. Cl. ............... 623/23.4; 623/18.11; 623/22.11; 623/22.3; 623/23.39; 623/23.43

(58) Field of Classification Search ............ 623/16.11, 623/17.11–17.16, 18.11, 19.11–19.13, 20.14–20.15, 623/20.21–20.24, 20.28–20.35, 21.13, 21.16–21.18, 623/22.11–22.3, 22.39–22.42, 23.39–23.43, 623/23.53
See application file for complete search history.

(56) References Cited

U.S. PATENT DOCUMENTS 3,521,302 A    7/1970    Muller
3,723,995 A    4/1973    Baumann
(Continued)

FOREIGN PATENT DOCUMENTS

DE    4102509    7/1992
(Continued)

OTHER PUBLICATIONS

Wenzel, S.A. and Shepherd, D.E.T., "Contact Stresses in Lumbar Total Disc Arthroplasty", vol. 17, No. 3, 2007, pp. 169-173, "Biomedical Materials and Engineering", Edgbaston, UK.

Clewlow, J.P., Pylios, T. and Shepherd, D.E.T., "Soft Layer Bearing Joins for Spine Arthroplasty", vol. 29, No. 10, Dec. 2008, pp. 1981-1985, "Materials and Design", Edgabaston, UK.

(Continued)

*Primary Examiner* — David Isabella
*Assistant Examiner* — Andrew Iwamaye
(74) *Attorney, Agent, or Firm* — Trego, Hines & Ladenheim, PLLC

(57) ABSTRACT

A prosthetic joint member includes: a generally concave cup with an outer surface that is bone-implantable, the cup including a first indexing feature; a concave insert disposed inside the cup, the insert comprising a rigid material and including a concave interior defining a nominal surface, the interior including a cantilevered flange defined by an undercut in the insert, the flange defining a wear-resistant first contact surface which protrudes inward relative to the nominal surface, the insert including a second indexing feature. The first and second indexing features engage each other so as to retain the insert in a fixed angular orientation relative to the cup.

18 Claims, 48 Drawing Sheets

U.S. PATENT DOCUMENTS

| | | | |
|---|---|---|---|
| 3,744,061 A | 7/1973 | Frost |
| 3,842,442 A | 10/1974 | Kolbel |
| 3,945,739 A | 3/1976 | Abe |
| 4,031,570 A | 6/1977 | Frey |
| 4,044,403 A | 8/1977 | D'Errico |
| 4,123,806 A | 11/1978 | Amstutz et al. |
| 4,126,924 A | 11/1978 | Akins et al. |
| 4,159,544 A | 7/1979 | Termanini |
| 4,224,696 A | 9/1980 | Murray et al. |
| 4,309,778 A | 1/1982 | Buechel et al. |
| 4,437,193 A | 3/1984 | Oh |
| 4,550,450 A | 11/1985 | Kinnett |
| 4,568,348 A | 2/1986 | Johnson et al. |
| 4,662,891 A | 5/1987 | Noiles |
| 4,673,408 A | 6/1987 | Grobbelaar |
| 4,676,798 A | 6/1987 | Noiles |
| 4,718,911 A | 1/1988 | Kenna |
| 4,759,766 A | 7/1988 | Buettner Janz et al. |
| 4,795,469 A | 1/1989 | Oh |
| 4,813,961 A | 3/1989 | Sostegni |
| 4,878,918 A | 11/1989 | Tari et al. |
| 4,904,106 A | 2/1990 | Love |
| 4,955,919 A | 9/1990 | Pappas et al. |
| 4,964,865 A | 10/1990 | Burkhead et al. |
| 4,997,432 A | 3/1991 | Keller |
| 5,061,288 A | 10/1991 | Berggren et al. |
| 5,062,853 A | 11/1991 | Forte |
| 5,080,675 A | 1/1992 | Lawes et al. |
| 5,080,678 A | 1/1992 | Spotorno et al. |
| 5,092,898 A | 3/1992 | Bekki et al. |
| 5,095,898 A | 3/1992 | Don Michael |
| 5,116,375 A | 5/1992 | Hofmann |
| 5,116,376 A | 5/1992 | May |
| 5,133,769 A | 7/1992 | Wagner et al. |
| 5,181,926 A | 1/1993 | Koch et al. |
| 5,197,987 A | 3/1993 | Koch et al. |
| 5,358,530 A | 10/1994 | Hodorek |
| 5,405,394 A | 4/1995 | Davidson |
| 5,413,604 A | 5/1995 | Hodge |
| 5,458,650 A | 10/1995 | Carret et al. |
| 5,462,362 A | 10/1995 | Yuhta et al. |
| 5,480,442 A | 1/1996 | Bertagnoli |
| 5,480,446 A | 1/1996 | Goodfellow et al. |
| 5,480,448 A | 1/1996 | Mikhail |
| 5,507,816 A | 4/1996 | Bullivant |
| 5,549,693 A | 8/1996 | Roux et al. |
| 5,549,695 A | 8/1996 | Spotorno et al. |
| 5,549,697 A | 8/1996 | Caldarise |
| 5,549,699 A | 8/1996 | MacMahon et al. |
| 5,549,700 A | 8/1996 | Graham et al. |
| 5,593,445 A | 1/1997 | Waits |
| 5,609,645 A | 3/1997 | Vinciguerra |
| 5,641,323 A | 6/1997 | Caldarise |
| 5,674,296 A | 10/1997 | Bryan et al. |
| 5,676,701 A | 10/1997 | Yuan et al. |
| 5,676,704 A | 10/1997 | Ries et al. |
| 5,702,456 A | 12/1997 | Pienkowski |
| 5,702,470 A | 12/1997 | Menon |
| 5,702,478 A | 12/1997 | Tornier |
| 5,725,584 A | 3/1998 | Walker et al. |
| 5,766,260 A | 6/1998 | Whiteside |
| 5,782,927 A | 7/1998 | Klawitter et al. |
| 5,800,555 A | 9/1998 | Gray et al. |
| 5,824,101 A | 10/1998 | Pappas |
| 5,871,542 A | 2/1999 | Goodfellow et al. |
| 5,871,546 A | 2/1999 | Colleran et al. |
| 5,879,404 A | 3/1999 | Bateman et al. |
| 5,879,406 A | 3/1999 | Lilley |
| 5,879,407 A | 3/1999 | Waggener |
| 5,893,889 A | 4/1999 | Harrington |
| 5,916,269 A | 6/1999 | Serbousek et al. |
| 5,935,174 A | 8/1999 | Dye |
| 5,935,175 A | 8/1999 | Ostiguy, Jr. et al. |
| 5,938,702 A | 8/1999 | Lopez et al. |
| 5,957,979 A | 9/1999 | Beckman et al. |
| 5,989,293 A | 11/1999 | Cook et al. |
| 5,989,294 A | 11/1999 | Marlow |
| 5,997,579 A | 12/1999 | Albretsson et al. |
| 6,013,103 A | 1/2000 | Kaufman et al. |
| 6,042,293 A | 3/2000 | Maughan |
| 6,059,830 A | 5/2000 | Lippencott, III et al. |
| 6,080,195 A | 6/2000 | Colleran et al. |
| 6,096,083 A | 8/2000 | Keller et al. |
| 6,126,695 A | 10/2000 | Semlitsch |
| 6,129,765 A | 10/2000 | Lopez et al. |
| 6,146,421 A | 11/2000 | Gordon et al. |
| 6,152,961 A | 11/2000 | Ostiguy, Jr. et al. |
| 6,162,252 A | 12/2000 | Kuras et al. |
| 6,162,256 A | 12/2000 | Ostiguy, Jr. et al. |
| 6,179,874 B1 | 1/2001 | Cauthen |
| 6,190,415 B1 | 2/2001 | Cooke et al. |
| 6,203,576 B1 | 3/2001 | Afriat et al. |
| 6,206,929 B1 | 3/2001 | Ochoa et al. |
| 6,217,249 B1 | 4/2001 | Merlo |
| 6,231,264 B1 | 5/2001 | McLaughlin et al. |
| 6,299,646 B1 | 10/2001 | Chambat et al. |
| 6,364,910 B1 | 4/2002 | Shultz et al. |
| 6,368,350 B1 | 4/2002 | Erickson et al. |
| 6,375,682 B1 | 4/2002 | Fleischmann et al. |
| 6,416,553 B1 | 7/2002 | White et al. |
| 6,425,921 B1 | 7/2002 | Grundei et al. |
| 6,475,243 B1 | 11/2002 | Sheldon et al. |
| 6,494,916 B1 | 12/2002 | Babalola et al. |
| 6,537,321 B1 | 3/2003 | Horber |
| 6,558,427 B2 | 5/2003 | Leclercq et al. |
| 6,626,947 B2 | 9/2003 | Lester et al. |
| 6,660,040 B2 | 12/2003 | Chan et al. |
| RE38,409 E | 1/2004 | Noiles |
| 6,719,800 B2 | 4/2004 | Meyers et al. |
| 6,740,117 B2 | 5/2004 | Ralph et al. |
| 6,740,118 B2 | 5/2004 | Eisermann et al. |
| 6,743,258 B1 | 6/2004 | Keller |
| 6,770,095 B2 | 8/2004 | Grinberg et al. |
| 6,866,685 B2 | 3/2005 | Chan et al. |
| 6,875,235 B2 | 4/2005 | Ferree |
| 6,893,465 B2 | 5/2005 | Huang |
| 6,896,703 B2 | 5/2005 | Barbieri et al. |
| 6,916,342 B2 | 7/2005 | Frederick et al. |
| 6,942,701 B2 | 9/2005 | Taylor |
| 6,949,105 B2 | 9/2005 | Bryan et al. |
| 6,964,686 B2 | 11/2005 | Gordon |
| 6,972,039 B2 | 12/2005 | Metzger et al. |
| 6,981,989 B1 | 1/2006 | Fleischmann et al. |
| 6,981,991 B2 | 1/2006 | Ferree |
| 6,986,791 B1 | 1/2006 | Metzger |
| 7,001,433 B2 | 2/2006 | Songer et al. |
| 7,022,142 B2 | 4/2006 | Johnson |
| 7,037,341 B2 | 5/2006 | Nowakowski |
| 7,060,099 B2 | 6/2006 | Carli et al. |
| 7,060,101 B2 | 6/2006 | O'Connor et al. |
| 7,066,963 B2 | 6/2006 | Naegerl |
| 7,083,650 B2 | 8/2006 | Moskowitz et al. |
| 7,083,651 B2 | 8/2006 | Diaz et al. |
| 7,083,652 B2 | 8/2006 | McCue et al. |
| 7,108,719 B2 | 9/2006 | Horber |
| 7,108,720 B2 | 9/2006 | Hanes |
| 7,115,145 B2 | 10/2006 | Richards |
| 7,121,755 B2 | 10/2006 | Schlapfer et al. |
| 7,128,761 B2 | 10/2006 | Kuras et al. |
| 7,153,325 B2 | 12/2006 | Kim et al. |
| 7,153,328 B2 | 12/2006 | Kim |
| 7,160,332 B2 | 1/2007 | Frederick et al. |
| 7,179,294 B2 | 2/2007 | Eisermann et al. |
| 7,214,243 B2 | 5/2007 | Taylor |
| 7,214,244 B2 | 5/2007 | Zubok et al. |
| 7,250,060 B2 | 7/2007 | Trieu |
| 7,267,693 B1 | 9/2007 | Mandell et al. |
| 7,270,679 B2 | 9/2007 | Istephanous et al. |
| 7,276,082 B2 | 10/2007 | Zdeblick et al. |
| 7,297,164 B2 | 11/2007 | Johnson et al. |
| 7,309,363 B2 | 12/2007 | Dietz |
| 7,326,250 B2 | 2/2008 | Beaurain et al. |
| 7,326,252 B2 | 2/2008 | Otto et al. |
| 7,326,253 B2 | 2/2008 | Synder et al. |
| 7,338,529 B1 | 3/2008 | Higgins |
| 7,393,362 B2 | 7/2008 | Cruchet et al. |
| 7,407,513 B2 | 8/2008 | Alleyne et al. |

| | | | |
|---|---|---|---|
| 7,442,211 B2 | 10/2008 | de Villiers et al. | |
| 7,465,320 B1 | 12/2008 | Kito et al. | |
| 7,468,076 B2 | 12/2008 | Zubok et al. | |
| 7,468,079 B2 | 12/2008 | Collier | |
| 7,470,287 B2 | 12/2008 | Tornier et al. | |
| 7,485,145 B2 | 2/2009 | Purcell | |
| 7,494,507 B2 | 2/2009 | Dixon et al. | |
| 7,531,002 B2 | 5/2009 | Sutton et al. | |
| 7,537,615 B2 | 5/2009 | Lemaire | |
| 7,550,009 B2 | 6/2009 | Arnin et al. | |
| 7,550,010 B2 | 6/2009 | Humphreys et al. | |
| 7,572,295 B2 | 8/2009 | Steinberg | |
| 7,572,296 B2 | 8/2009 | Scott et al. | |
| 7,578,848 B2 | 8/2009 | Albert et al. | |
| 7,582,115 B2 | 9/2009 | Weber | |
| 7,588,384 B2 | 9/2009 | Yokohara | |
| 7,601,174 B2 | 10/2009 | Kelley et al. | |
| 7,611,653 B1 | 11/2009 | Elsner et al. | |
| 7,618,439 B2 | 11/2009 | Zubok et al. | |
| 7,618,459 B2 | 11/2009 | Justin et al. | |
| 7,621,956 B2 | 11/2009 | Paul et al. | |
| 7,655,041 B2 | 2/2010 | Clifford et al. | |
| 7,658,767 B2 | 2/2010 | Wyss | |
| 7,682,398 B2 | 3/2010 | Croxton et al. | |
| 7,740,659 B2 | 6/2010 | Zarda et al. | |
| 7,758,645 B2 | 7/2010 | Studer | |
| 7,758,653 B2 | 7/2010 | Steinberg | |
| 7,776,085 B2 | 8/2010 | Bernero et al. | |
| 7,879,095 B2 | 2/2011 | Pisharodi | |
| 7,905,919 B2 | 3/2011 | Kellar et al. | |
| 7,914,580 B2 | 3/2011 | Kellar et al. | |
| 7,955,395 B2 | 6/2011 | Shea et al. | |
| 8,007,539 B2 | 8/2011 | Slone | |
| 8,029,574 B2 | 10/2011 | Kellar et al. | |
| 8,070,823 B2 | 12/2011 | Kellar et al. | |
| 2002/0035400 A1 | 3/2002 | Bryan et al. | |
| 2002/0111682 A1 | 8/2002 | Ralph et al. | |
| 2002/0143402 A1 | 10/2002 | Steinberg | |
| 2002/0147499 A1 | 10/2002 | Shea et al. | |
| 2003/0055500 A1 | 3/2003 | Fell et al. | |
| 2003/0081989 A1 | 5/2003 | Kondoh | |
| 2003/0114935 A1 | 6/2003 | Chan et al. | |
| 2003/0191534 A1 | 10/2003 | Viart et al. | |
| 2003/0220691 A1 | 11/2003 | Songer et al. | |
| 2004/0010316 A1 | 1/2004 | William et al. | |
| 2004/0024460 A1 | 2/2004 | Ferree | |
| 2004/0034433 A1 | 2/2004 | Chan et al. | |
| 2004/0073311 A1 | 4/2004 | Ferree | |
| 2004/0088052 A1 | 5/2004 | Dearnaley | |
| 2004/0093087 A1 | 5/2004 | Ferree et al. | |
| 2004/0117021 A1 | 6/2004 | Biedermann et al. | |
| 2004/0143332 A1 | 7/2004 | Krueger et al. | |
| 2004/0143334 A1 | 7/2004 | Ferree | |
| 2004/0167626 A1 | 8/2004 | Geremakis et al. | |
| 2004/0167629 A1 | 8/2004 | Geremakis et al. | |
| 2004/0172021 A1 | 9/2004 | Khalili | |
| 2004/0215345 A1 | 10/2004 | Perrone, Jr. et al. | |
| 2004/0220674 A1 | 11/2004 | Pria et al. | |
| 2004/0260396 A1 | 12/2004 | Ferree et al. | |
| 2004/0267374 A1 | 12/2004 | Friedrichs | |
| 2004/0267375 A1 | 12/2004 | Friedrichs | |
| 2005/0004572 A1 | 1/2005 | Biedermann et al. | |
| 2005/0015152 A1 | 1/2005 | Sweeney | |
| 2005/0021145 A1 | 1/2005 | de Villiers et al. | |
| 2005/0038516 A1 | 2/2005 | Spoonamore | |
| 2005/0055101 A1 | 3/2005 | Sifneos | |
| 2005/0071007 A1 | 3/2005 | Malek | |
| 2005/0080488 A1 | 4/2005 | Schultz | |
| 2005/0113926 A1 | 5/2005 | Zucherman et al. | |
| 2005/0113931 A1 | 5/2005 | Horber | |
| 2005/0125065 A1 | 6/2005 | Zucherman et al. | |
| 2005/0143827 A1 | 6/2005 | Globerman et al. | |
| 2005/0165485 A1 | 7/2005 | Trieu | |
| 2005/0171604 A1 | 8/2005 | Michalow | |
| 2005/0171614 A1 | 8/2005 | Bacon | |
| 2005/0192674 A1 | 9/2005 | Ferree | |
| 2005/0197706 A1 | 9/2005 | Hovorka et al. | |
| 2005/0203626 A1 | 9/2005 | Sears et al. | |
| 2005/0216081 A1 | 9/2005 | Taylor | |
| 2005/0251261 A1 | 11/2005 | Peterman | |
| 2005/0251262 A1 | 11/2005 | de Villiers et al. | |
| 2005/0261776 A1 | 11/2005 | Taylor | |
| 2005/0288793 A1 | 12/2005 | Dong et al. | |
| 2006/0020342 A1 | 1/2006 | Ferree et al. | |
| 2006/0025862 A1 | 2/2006 | Villiers et al. | |
| 2006/0041314 A1 | 2/2006 | Millard | |
| 2006/0064169 A1 | 3/2006 | Ferree | |
| 2006/0085076 A1 | 4/2006 | Krishna et al. | |
| 2006/0095135 A1 | 5/2006 | Kovacevic | |
| 2006/0129240 A1 | 6/2006 | Lessar et al. | |
| 2006/0136062 A1 | 6/2006 | DiNello et al. | |
| 2006/0178744 A1 | 8/2006 | de Villiers et al. | |
| 2006/0190079 A1 | 8/2006 | Istephanous et al. | |
| 2006/0200247 A1 | 9/2006 | Charrois | |
| 2006/0217809 A1 | 9/2006 | Albert et al. | |
| 2006/0217815 A1 | 9/2006 | Gibbs et al. | |
| 2006/0235527 A1 | 10/2006 | Buettner-Janz et al. | |
| 2006/0241765 A1 | 10/2006 | Burn et al. | |
| 2006/0241766 A1 | 10/2006 | Felton et al. | |
| 2006/0259147 A1 | 11/2006 | Krishna et al. | |
| 2006/0259148 A1 | 11/2006 | Bar-Ziv | |
| 2006/0271200 A1 | 11/2006 | Greenlee | |
| 2006/0293752 A1 | 12/2006 | Moumene et al. | |
| 2007/0021837 A1 | 1/2007 | Ashman | |
| 2007/0032875 A1 | 2/2007 | Blacklock et al. | |
| 2007/0032877 A1 | 2/2007 | Whiteside | |
| 2007/0050032 A1 | 3/2007 | Gittings et al. | |
| 2007/0073405 A1 | 3/2007 | Verhulst et al. | |
| 2007/0073410 A1 | 3/2007 | Raugel | |
| 2007/0083267 A1 | 4/2007 | Miz et al. | |
| 2007/0100447 A1 | 5/2007 | Steinberg | |
| 2007/0100454 A1 | 5/2007 | Burgess et al. | |
| 2007/0100456 A1 | 5/2007 | Dooris et al. | |
| 2007/0106391 A1 | 5/2007 | Ronk | |
| 2007/0118223 A1 | 5/2007 | Allard et al. | |
| 2007/0123990 A1 | 5/2007 | Sharifi-Mehr | |
| 2007/0156246 A1 | 7/2007 | Meswania et al. | |
| 2007/0168037 A1 | 7/2007 | Posnick | |
| 2007/0173936 A1 | 7/2007 | Hester et al. | |
| 2007/0185578 A1 | 8/2007 | O'Neil et al. | |
| 2007/0208427 A1 | 9/2007 | Davidson et al. | |
| 2007/0213821 A1 | 9/2007 | Kwak et al. | |
| 2007/0225806 A1 | 9/2007 | Squires et al. | |
| 2007/0225810 A1 | 9/2007 | Colleran et al. | |
| 2007/0225818 A1 | 9/2007 | Reubelt et al. | |
| 2007/0233244 A1 | 10/2007 | Lopez et al. | |
| 2007/0239276 A1 | 10/2007 | Squires et al. | |
| 2008/0065211 A1 | 3/2008 | Albert et al. | |
| 2008/0065216 A1 | 3/2008 | Hurlbert et al. | |
| 2008/0071381 A1 | 3/2008 | Buscher et al. | |
| 2008/0077137 A1 | 3/2008 | Balderston | |
| 2008/0133017 A1 | 6/2008 | Beyar et al. | |
| 2008/0133022 A1 | 6/2008 | Caylor | |
| 2008/0154263 A1 | 6/2008 | Janowski et al. | |
| 2008/0154369 A1 | 6/2008 | Barr et al. | |
| 2008/0161924 A1 | 7/2008 | Viker | |
| 2008/0161930 A1 | 7/2008 | Carls et al. | |
| 2008/0195212 A1 | 8/2008 | Nguyen et al. | |
| 2008/0215156 A1 | 9/2008 | Duggal et al. | |
| 2008/0221689 A1 | 9/2008 | Chaput et al. | |
| 2008/0221690 A1 | 9/2008 | Chaput et al. | |
| 2008/0228276 A1 | 9/2008 | Mathews et al. | |
| 2008/0228282 A1 | 9/2008 | Brodowski | |
| 2008/0243253 A1 | 10/2008 | Levieux | |
| 2008/0243262 A1 | 10/2008 | Lee | |
| 2008/0243263 A1 | 10/2008 | Lee et al. | |
| 2008/0300685 A1 | 12/2008 | Carls et al. | |
| 2009/0005872 A1 | 1/2009 | Moumene et al. | |
| 2009/0012619 A1 | 1/2009 | Cordaro et al. | |
| 2009/0030521 A1 | 1/2009 | Lee et al. | |
| 2009/0036992 A1 | 2/2009 | Tsakonas | |
| 2009/0043391 A1 | 2/2009 | de Villiers et al. | |
| 2009/0054986 A1 | 2/2009 | Cordaro et al. | |
| 2009/0062920 A1 | 3/2009 | Tauber | |
| 2009/0076614 A1 | 3/2009 | Arramon | |
| 2009/0082867 A1 | 3/2009 | Sebastian Bueno et al. | |
| 2009/0082873 A1 | 3/2009 | Hazebrouck et al. | |
| 2009/0088865 A1 | 4/2009 | Brehm | |

| | | | |
|---|---|---|---|
| 2009/0105758 A1 | 4/2009 | Gimbel et al. |
| 2009/0125111 A1 | 5/2009 | Copf, Jr. |
| 2009/0138090 A1 | 5/2009 | Hurlbert et al. |
| 2009/0157185 A1 | 6/2009 | Kim |
| 2009/0192616 A1 | 7/2009 | Zielinski |
| 2009/0192617 A1 | 7/2009 | Arramon et al. |
| 2009/0215111 A1 | 8/2009 | Veenstra et al. |
| 2009/0234458 A1 | 9/2009 | de Villiers et al. |
| 2009/0248161 A1 | 10/2009 | Theofilos et al. |
| 2009/0265009 A1 | 10/2009 | Ward et al. |
| 2009/0270986 A1 | 10/2009 | Christensen |
| 2009/0276051 A1 | 11/2009 | Arramon et al. |
| 2009/0281629 A1 | 11/2009 | Roebling et al. |
| 2009/0306784 A1 | 12/2009 | Blum |
| 2009/0306785 A1 | 12/2009 | Farrar et al. |
| 2009/0326656 A1 | 12/2009 | de Villiers et al. |
| 2009/0326663 A1 | 12/2009 | Dun |
| 2009/0326664 A1 | 12/2009 | Wagner et al. |
| 2009/0326665 A1 | 12/2009 | Wyss et al. |
| 2009/0326666 A1 | 12/2009 | Wyss et al. |
| 2009/0326668 A1 | 12/2009 | Dun |
| 2010/0004746 A1 | 1/2010 | Arramon |
| 2010/0030335 A1 | 2/2010 | Arramon |
| 2010/0063589 A1 | 3/2010 | Tepic |
| 2010/0063597 A1 | 3/2010 | Gradel |
| 2010/0100189 A1 | 4/2010 | Metzger |
| 2010/0100191 A1 | 4/2010 | May et al. |
| 2010/0131073 A1 | 5/2010 | Meridew et al. |
| 2010/0161064 A1 | 6/2010 | Kellar et al. |
| 2010/0161072 A1 | 6/2010 | Drescher |
| 2010/0191342 A1 | 7/2010 | Byrd et al. |
| 2010/0262250 A1 | 10/2010 | Kellar et al. |
| 2010/0268340 A1 | 10/2010 | Capote et al. |
| 2010/0292794 A1 | 11/2010 | Metz-Stavenhagen |
| 2010/0331993 A1 | 12/2010 | Gradl |
| 2011/0009975 A1 | 1/2011 | Allen et al. |
| 2011/0015752 A1 | 1/2011 | Meridew |
| 2011/0190901 A1 | 8/2011 | Weissberg et al. |

FOREIGN PATENT DOCUMENTS

| | | |
|---|---|---|
| DE | 4102510 | 7/1992 |
| DE | 4423020 | 1/1996 |
| DE | 10164328 | 7/2003 |
| DE | 202008004709 | 7/2008 |
| EP | 46926 | 3/1982 |
| EP | 636353 | 2/1995 |
| EP | 648478 | 4/1995 |
| EP | 974316 | 1/2000 |
| EP | 1114624 | 7/2001 |
| EP | 1508315 | 2/2005 |
| FR | 2750036 | 12/1997 |
| FR | 2805456 | 8/2001 |
| FR | 2883723 | 10/2006 |
| FR | 2897528 | 8/2007 |
| FR | 2936145 | 3/2010 |
| GB | 1322680 | 7/1973 |
| GB | 1417407 | 12/1975 |
| GB | 1527498 | 10/1978 |
| GB | 1528906 | 10/1978 |
| GB | 2191402 | 12/1987 |
| JP | 2004011782 | 1/2004 |
| JP | 2004169820 | 6/2004 |
| WO | 9523566 | 9/1995 |
| WO | 9604867 | 2/1996 |
| WO | 9716138 | 5/1997 |
| WO | 9738650 | 11/1997 |
| WO | 0023015 | 4/2000 |
| WO | 03049649 | 6/2003 |
| WO | 2004066882 | 8/2004 |
| WO | 2005039455 | 5/2005 |
| WO | 2006069465 | 7/2006 |
| WO | 2007087730 | 8/2007 |
| WO | 2008088777 | 7/2008 |
| WO | 2008094260 | 8/2008 |
| WO | 2009094477 | 7/2009 |
| WO | 2009105884 | 9/2009 |
| WO | 2009121450 | 10/2009 |
| WO | 2009126908 | 10/2009 |
| WO | 2010095125 | 8/2010 |
| WO | 2011011340 | 1/2011 |

OTHER PUBLICATIONS

Parea, Philippe E., Chana, Frank W., Bhattacharyab, Sanghita and Goelb, Vijay K., "Surface Slide Track Mapping of Implants for Total Disc Arthroplasty", vol. 42, No. 2, Jan. 19, 2009, pp. 131-139, "Journal of Biomechanics", [online] [retrieved Feb. 19, 2010].

Dooris, Andrew P., Goel, Vijay K., Todd, Dwight T., Grosland, Nicole M., Wilder, David G., "Load Sharing in a Lumbar Motion Segment Implanted with an Artificial Disc Under Combined Sagittal Plane Loading", BED-vol. 42, 1999, pp. 277-278, "American Society of Mechanical Engineers", Iowa City, Iowa.

Wang, W., Wang, F., Jin, Z., Dowson, D., Hu, Y., "Numerical Lubrication Simulation of Metal-on-Metal Artificial Hip Joint Replacements: Ball-in-Socket Model and Ball-on-Plane Model", vol. 223 Part J, 2009, pp. 1073-1082, "Journal Engineering Tribology", [online] [retrieved Mar. 28, 2011].

Wang, F., Jin, Z., "Effect of Non-Spherical Bearing Geometry on Transient Elastohydrodynamic Lubrication in Metal-on-Metal Hip Joint Replacements", vol. 221, Part J, 2007, pp. 379-389, "Journal of Engineering Tribology", [online] [retrieved Mar. 28, 2011].

Wang, F., Brockett, C., Williams, S., Udofia, I., Fisher, J., Jin, Z., "Lubrication and Friction Prediction in Metal-on-Metal Hip Implants", vol. 53, Jan. 2008, pp. 1277-1293, "Phys. Med. Biol.", United Kingdom.

Clarke, I., "Role of Ceramic Implants: Design and Clinical Success with Total Hip Prosthetic Ceramic-to-Ceramic Bearings", No. 282, Sep. 1992, pp. 19-30, "Clinical Orthopeadics and Related Research", Kinamed, Inc., Newbury Park, California.

Gardelin, R, Seminario, J., Corradini, C., Fenollosa Gomez, J., "Total Hip Prostheses with Cup and Ball in Ceramic and Metal Sockets", vols. 192-195, 2001, pp. 983-988, "Key Engineering Materials", Trans Tech Publications, Switzerland.

Bruckmann, H., Keuscher, G., Huttinger, K., "Carbon, A Promising Material in Endoprosthetics. Part 2: Tribological Properties", vol. 1, Apr. 1980, pp. 73-81, "Biomaterials", IPC Business Press, West Germany.

Jalali-Vahid, D., Jagatia, M., Jin, Z., Dowson, D., "Prediction of Lubricating Film Thickness in UHMWPE Hip Joint Replacements", vol. 34, 2001, pp. 261-266, "Journal of Biomechanics", Elsevier Science Ltd., United Kingdom.

Post, Zachary D., Matar, Wadih Y., Van De Leur, Tim, Grossman, Eric L., Austin, Matthew S., "Mobile-Bearing Total Knee Arthroplasty", vol. 25, No. 6, 2010, pp. 998-1003, "Journal of Arthroplasty", Philadelphia, Pennsylvania.

Fregly, Benjamin, J., Bei, Yanhong, Sylvester, Mark E., "Experimental Evaluation of an Elastic Foundation Model to Predict Contact Pressures in Knee Replacements", vol. 36, No. 11, Nov. 2003, pp. 1659-1668, "Journal of Biomechanics", Gainesville, Florida.

Minns, R.J., Campbell, J., "The 'Sliding Meniscus' Knee Prosthesis: Design Concepts", vol. 8, No. 4, Oct. 1979, pp. 201-205, "Engineering in Medicine", London, England.

Strickland, M.A., Taylor, M., "In-Silico Wear Prediction for Knee Replacements—Methodology and Corroboration", vol. 42, No. 10, Jul. 2009, "Journal of Biomechanics", Southampton, United Kingdom.

Halloran, Jason P., Easley, Sarah K., Patrella, Anthony J., Rullkoetter, Paul J., "Comparison of Deformable and Elastic Foundation Finite Element Simulations for Predicting Knee Replacement Mechanics", vol. 127, No. 5, Oct. 2005, pp. 813-818, "Journal of Biomechanical Engineering", Denver, Colorado.

Guerinot, Alexandre, E., Magleby, Spencer, P. Howell, Larry L., "Preliminary Design Concepts for Compliant Mechanism Prosthetic Knee Joints", vol. 2B, pp. 1103-1111, 2004, "Proceedings of the ASME Design Engineering Technical Conference", Provo, Utah.

Walker, Peter, S., Sathasivam, Shivani, "The Design of Guide Surfaces for Fixed-Bearing and Mobile-Bearing Knee Replacements", vol. 32, No. 1, pp. 27-34, Jan. 1999, "Journal of Biomechanics", Middlesex, United Kingdom.

Swanson, S., "The State of the Art in Joint Replacement, Part 2: Present Practice and Results", pp. 335-339, Nov. 1977, "Journal of Medical Engineering and Technology", London, United Kingdom.

Huttinger, K.J., Bruckmann, H., Rettig, H., Weber, U., "Development and Clinical Testing of Carbon Implants for Orthopedic Surgery", "Bundesministerium fur Forschung und Technologie", Jan. 1981, Schunk & Ebe GmbH, Germany, translation from German to English by the U.S. Department of Commerce, National Technical Information Service.

Faizan, A., Goel, V.K., Garfin, S.R., Bono, C.M., Serhan, H., Biyani, A., Elgafy, H., Krishna, M. Friesem, T., "Do Design Variations in the Artificial Disc Influence Cervical Spine Biomechanics? A Finite Investigation", Engineering Center for Orthopaedic Research Exellence (E-CORE), Departments of Bioengineering and Orthopaedic Surgery, 5046 NI, MS 303, Colleges of Engineering and Medicine, University of Toledo, Toledo, Ohio 43606, USA, Published online: Nov. 21, 2009.

Walter, A., Plitz, W., "Wear Characteristics of Ceramic-to-Ceramic Hip Joint Endoprostheses", vol. VIII, p. 178, Apr. 25-28, 1985, "The 11th Annual Meeting of the Society for Biomaterials", San Diego, California, US.

St. John, K.R., Zardiackas, L.D., Poggie, R.A., "Wear Evaluation of Cobalt-Chromium Alloy for Use in a Metal-on-Metal Hip Prosthesis", vol. 68, pp. 1-14, Jan. 15, 2004, "Journal of Biomedical Materials Research, Part B, Applied Biomaterials", Wiley Periodicals, United States.

Scholes, S.C., Burgess, I.C., Marsden, H.R., Unsworth, A., Jones, E., Smith, N., "Compliant Layer Acetabular Cups: Friction Testing of a Range of Materials and Designs for a New Generation of Prosthesis that Mimics the Natural Joint", vol. 220, pp. 583-596, Jul. 2006, "Proceedings of the Institution of Mechanical Engineers, Part H", "Journal of Engineering in Medicine", United Kingdom.

Gao, L., Wang, F., Yang, R. Jin, Z., "Effect of 3D Physiological Loading and Motion on Elastohydrodynamic Lubrication of Metal-on-Metal Total Hip Replacements", vol. 31, pp. 720-729, 2009, "Medical Engineering & Physics".

Kellar et al.; U.S. Appl. No. 13/311,119, filed Dec. 5, 2011.

PROSTHETIC JOINT ASSEMBLY AND JOINT MEMBER THEREFOR

CROSS-REFERENCE TO RELATED APPLICATIONS

This application is a Continuation-in-Part of application Ser. No. 13/311,119, filed Dec. 5, 2011, currently pending, which is a Continuation of application Ser. No. 13/073,963, filed Mar. 28, 2011, now U.S. Pat. No. 8,070,823, which is a Continuation-in-Part of application Ser. No. 12/826,620, filed Jun. 29, 2010, Now U.S. Pat. No. 7,914,580, which is a Continuation-in-Part of application Ser. No. 12/714,288, filed Feb. 26, 2010, now U.S. Pat. No. 7,905,919, which is a Continuation-in-Part of application Ser. No. 11/936,601, filed Nov. 7, 2007, currently pending, which claims the benefit of Provisional Patent Application 60/864,667, filed Nov. 7, 2006.

BACKGROUND OF THE INVENTION

This invention relates generally to medical implants, and more particularly to prosthetic joints having conformal geometries and wear resistant properties.

Medical implants, such as knee, hip, and spine orthopedic replacement joints and other joints and implants have previously consisted primarily of a hard metal motion element that engages a polymer contact pad. This has usually been a high density high wear resistant polymer, for example Ultra-High Molecular Weight Polyethylene (UHMWPE), or other resilient material. The problem with this type of configuration is the polymer eventually begins to degrade due to the caustic nature of blood, the high impact load, and high number of load cycles. As the resilient member degrades, pieces of polymer may be liberated into the joint area, often causing accelerated wear, implant damage, and tissue inflammation and harm.

It is desirable to employ a design using a hard member on a hard member (e.g. metals or ceramics), thus eliminating the polymer. Such a design is expected to have a longer service life. Extended implant life is important as it is now often required to revise or replace implants. Implant replacement is undesirable from a cost, inconvenience, patient health, and resource consumption standpoint.

Implants using two hard elements of conventional design will be, however, subject to rapid wear. First, a joint having one hard, rigid element on another will not be perfectly shaped to a nominal geometry. Such imperfections will result in points of high stress, thus causing localized wear. Furthermore, two hard elements would lack the resilient nature of a natural joint. Natural cartilage has a definite resilient property, absorbing shock and distributing periodic elevated loads. This in turn extends the life of a natural joint and reduces stress on neighboring support bone and tissue. If two rigid members are used, this ability to absorb the shock of an active lifestyle could be diminished. The rigid members would transmit the excessive shock to the implant to bone interface. Some cyclical load in these areas stimulates bone growth and strength; however, excessive loads or shock stress or impulse loading the bone-to-implant interface will result in localized bone mass loss, inflammation, and reduced support.

BRIEF SUMMARY OF THE INVENTION

These and other shortcomings of the prior art are addressed by the present invention, which provides a prosthetic joint having wear-resistant contacting surfaces with conformal properties.

According to one aspect of the invention, a prosthetic member includes: a cup with an outer surface that is bone-implantable, the cup including a first indexing feature; an insert disposed inside the cup, the insert comprising a rigid material and including a concave interior defining a nominal surface, the interior including a cantilevered flange defined by an undercut in the insert, the flange defining a wear-resistant first contact surface which protrudes inward relative to the nominal surface, the insert including a second indexing feature; wherein the first and second indexing features engage each other so as to retain the insert in a fixed angular orientation relative to the cup.

BRIEF DESCRIPTION OF THE DRAWINGS

The invention may be best understood by reference to the following description taken in conjunction with the accompanying drawing figures in which.

DETAILED DESCRIPTION OF THE INVENTION

The present invention provides a specialized implant contact interface (implant geometry). In this geometry, an implanted joint includes two typically hard (i.e. metal or ceramic) members; however, at least one of the members is formed such that it has the characteristics of a resilient member, such as: the ability to absorb an impact load; the ability to absorb high cycle loading; the ability to be self cleaning; and the ability to function as a hydrodynamic and/or hydrostatic bearing.

Generally, the contact resilient member is flexible enough to allow elastic deformation and avoid localized load increases, but not so flexible as to risk plastic deformation, cracking and failure. In particular, the resilient member is designed such that the stress levels therein will be below the high-cycle fatigue endurance limit. As an example, the resilient member might be only about 10% to about 20% as stiff as a comparable solid member. It is also possible to construct the resilient member geometry with a variable stiffness, i.e. having a low effective spring rate for small deflections and a higher rate as the deflections increase, to avoid failure under sudden heavy loads.

Figure 1:
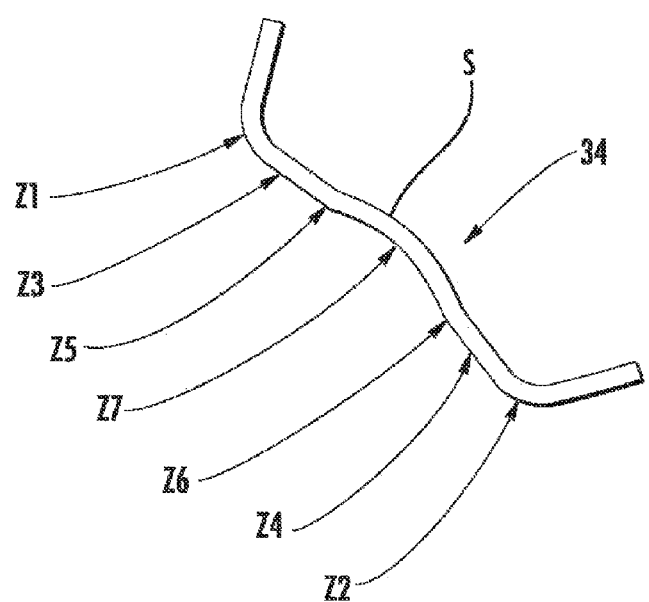
FIG. 1 is a cross-sectional view of a portion of a resilient contact member constructed in accordance with the present invention.

FIG. 1 illustrates an exemplary contact member 34 including a basic resilient interface geometry. The contact member 34 is representative of a portion of a medical implant and is made of one or more metals or ceramics (for example, partially stabilized Zirconia). It may be coated as described below. The geometry includes a lead-in shape, Z1 and Z2, a contact shape, Z3 and Z4, a lead-out shape, Z5 and Z6, and a relieved shape, Z7. It may be desired to vary the cross-sectional thickness to achieve a desired mechanical stiffness to substrate resilience characteristic. The presence of the relieved region Z7 introduces flexibility into the contact member 34, reduces the potential for concentrated point contact with a mating curved member, and provides a reservoir for a working fluid.

The Z7 region may be local to the contact member 34 or may be one of several. In any case, it may contain a means of providing fluid pressure to the internal contact cavity to produce a hydrostatic interface. A passive (powered by the regular motion of the patient) or active (powered by micro components and a dedicated subsystem) pumping means and optional filtration may be employed to provide the desired fluid interaction.

A hydrodynamic interface is desirable as, by definition, it means the contact member 34 is not actually touching the mating joint member. The lead-in and lead-out shapes Z1, Z2, Z5, Z6 are configured to generate a shear stress in the working fluid so as to create the fluid "wedge" of a hydrodynamic support.

Figure 2:
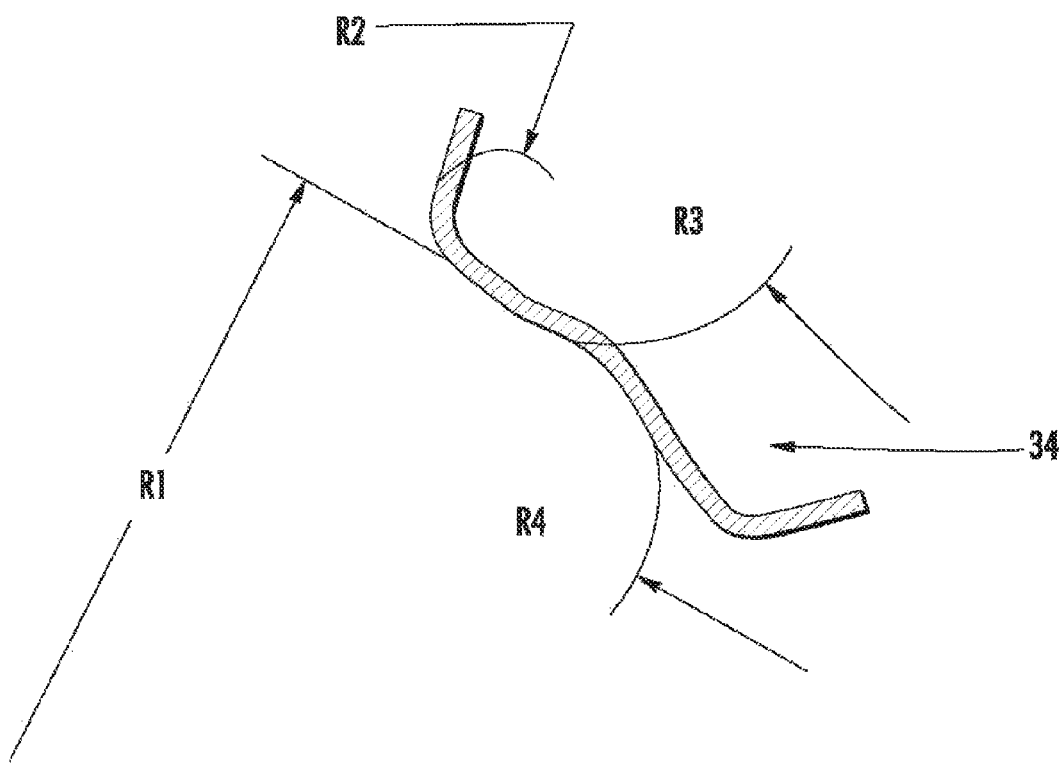
FIG. 2 is an enlarged view of the contact member of FIG. 1 in contact with a mating joint member.
Figure 3:
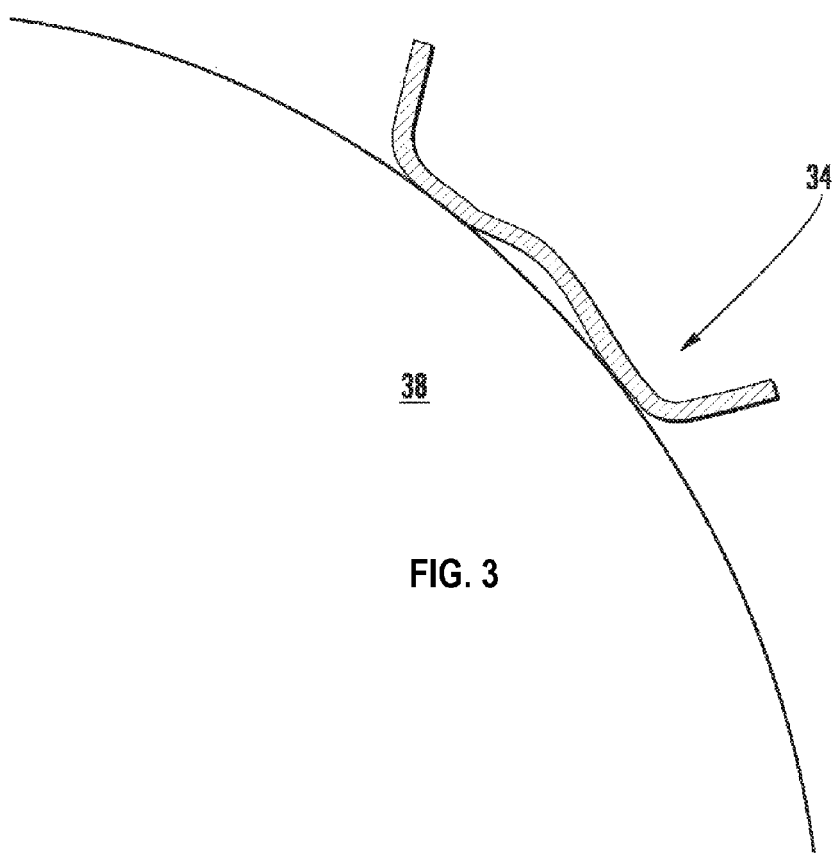
FIG. 3 is a side view of a resilient contact member in contact with a mating joint member.

FIG. 2 shows a closer view of the contact member 34. It may be desirable to make the contact radius (Z3 and Z4) larger or smaller, depending on the application requirement and flexural requirement. For example, FIG. 3 illustrates the contact member 34 in contact with a mating joint member 38 having a substantially larger radius than the contact member 34. The radius ratio between the two joint members is not particularly critical, so long as one of the members exhibits the resilient properties described herein.

The contact member 34 includes an osseointegration surface "S", which is a surface designed to be infiltrated by bone growth to improve the connection between the implant and the bone. Osseointegration surfaces may be made from materials such as TRABECULAR METAL, textured metal, or sintered or extruded implant integration textures. TRABECULAR METAL is an open metal structure with a high porosity (e.g. about 80%) and is available from Zimmer, Inc., Warsaw, Ind. 46580 USA.

Figure 4:
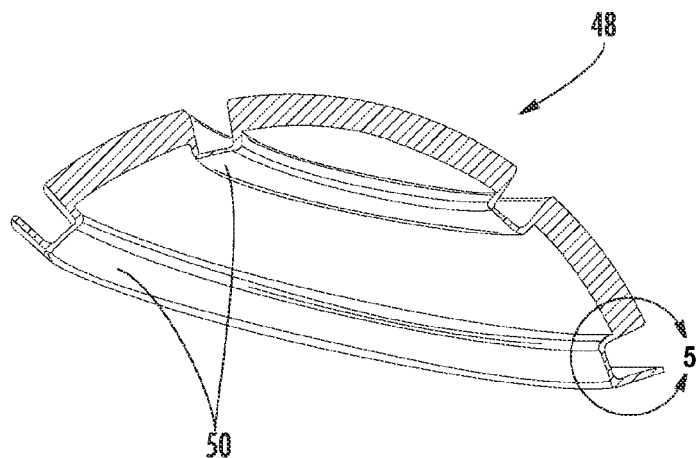
FIG. 4 is a cross-sectional view of a cup for an implant according to an alternate embodiment of the invention.
Figure 5:
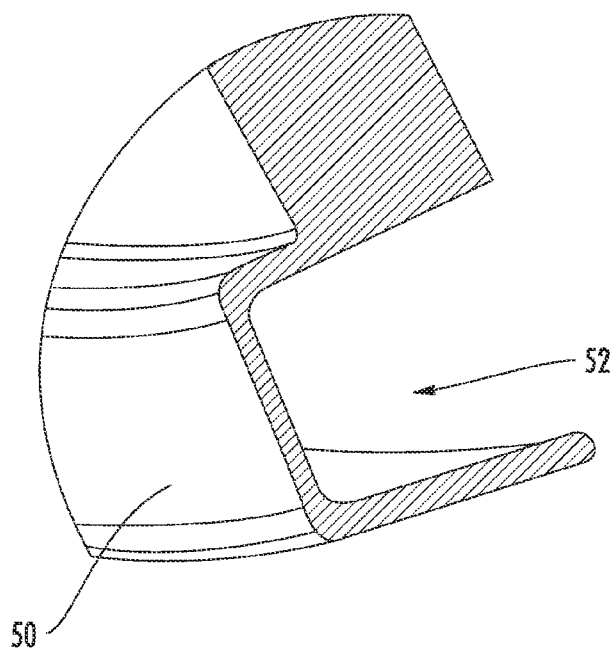
FIG. 5 is an enlarged view of a portion of the cup of FIG. 4.
Figure 6:
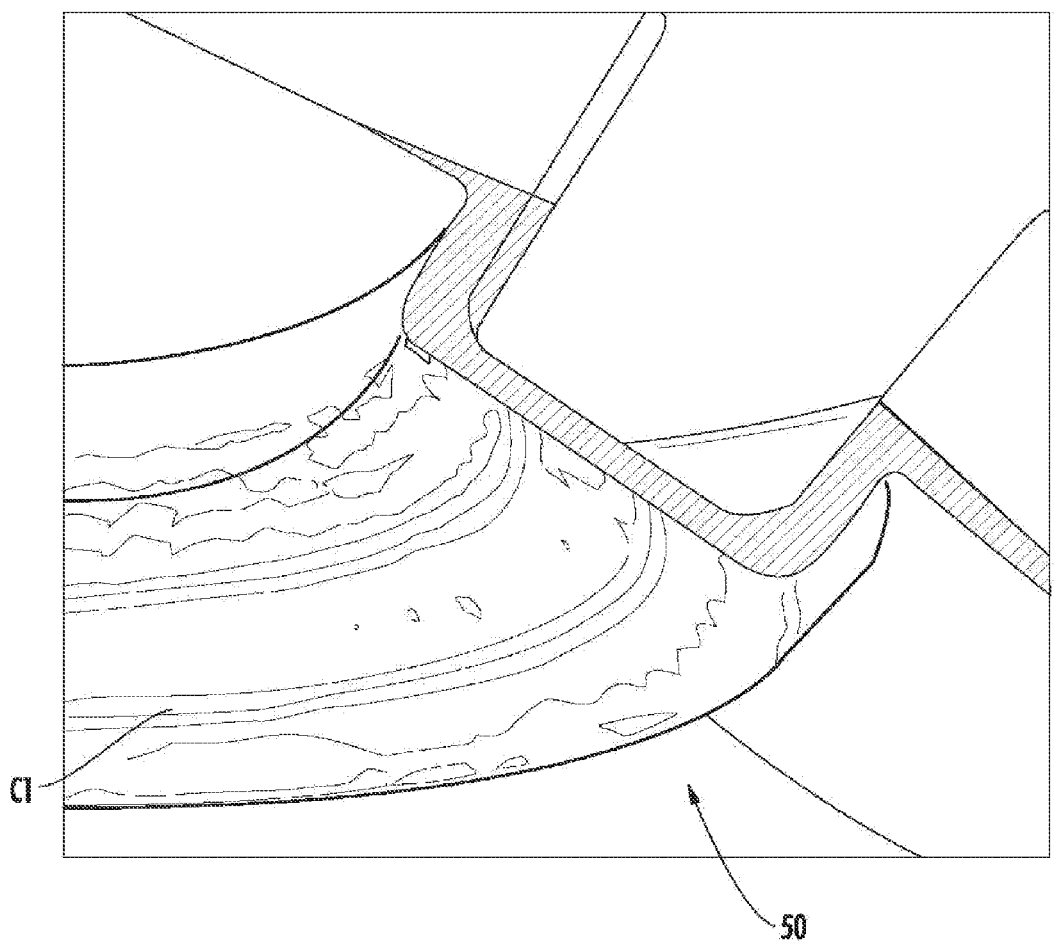
FIG. 6 is a perspective view of a finite element model of a joint member.

FIGS. 4 and 5 illustrate a cup 48 of metal or ceramic with two integrally-formed contact rings 50. More contact rings may be added if needed. As shown in FIG. 5, the volume behind the contact rings 50 may be relieved. This relieved area 52 may be shaped so as to produce a desired balance between resilience and stiffness. A varying cross-section geometry defined by varying inner and outer spline shapes may be desired. In other words, a constant thickness is not required. A material such as a gel or non-Newtonian fluid (not shown) may be disposed in the relieved area 52 to modify the stiffness and damping characteristics of the contact rings 50 as needed for a particular application. The cup 48 could be used as a stand-alone portion of a joint, or it could be positioned as a liner within a conventional liner. The contact ring 50 is shown under load in FIG. 6, which depicts contour lines of highest compressive stress at "C1". This is the portion of the contact ring 50 that would be expected to undergo bending first. The bearing interface portion of the resilient contact member could be constructed as a bridge cross-section supported on both sides as shown or as a cantilevered cross-section depending on the desired static and dynamic characteristics.

Figure 8:
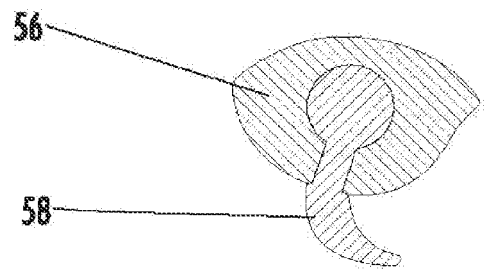
FIG. 8 is an enlarged view of a portion of FIG. 7.
Figure 7:
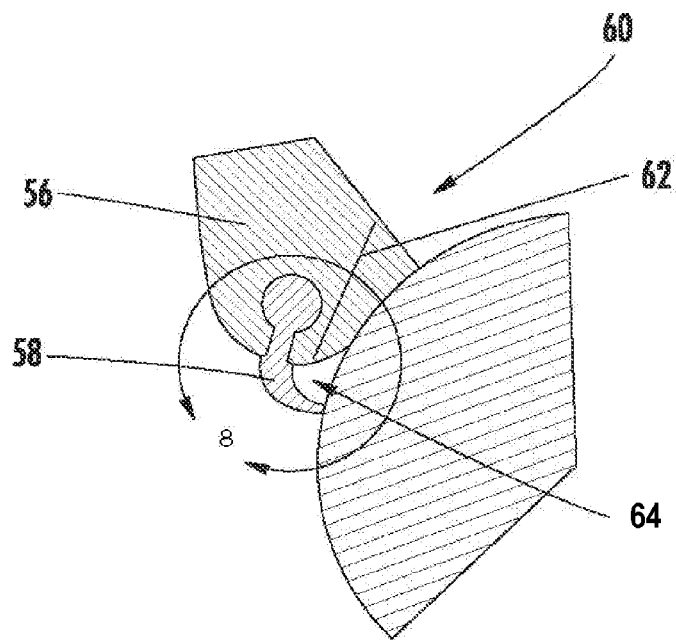
FIG. 7 is a cross-sectional view of an implant joint including a flexible seal.
Figure 9:
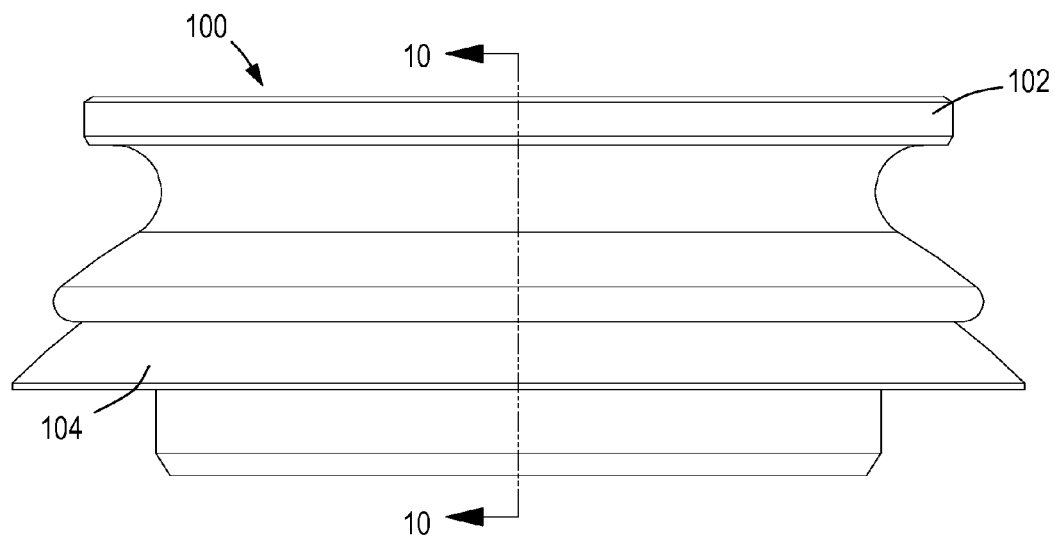
FIG. 9 is a side view of a prosthetic joint constructed in accordance with an aspect of the present invention.

FIGS. 7 and 8 illustrate an implant 56 of rigid material which includes a wiper seal 58. The wiper seal 58 keeps particles out of the contact area (seal void) 60 of the implant 58, and working fluid (natural or synthetic) in. The seal geometry is intended to be representative and a variety of seal characteristics may be employed; such as a single lip seal, a double or multiple lip seal, a pad or wiper seal made from a variety of material options. Different seal mounting options may be used, for example a lobe in a shaped groove as shown in FIGS. 7 and 8, a retaining ring or clamp, or an adhesive. The wiper seal 58 may also be integrated into the contact face of the interface zone.

It may be desirable to create a return passage 62 from the seal void region 60 back into the internal zone 64 in order to stabilize the pressure between the two and to allow for retention of the internal zone fluid if desired. This is especially relevant when the hydrostatic configuration is considered.

Figure 10:
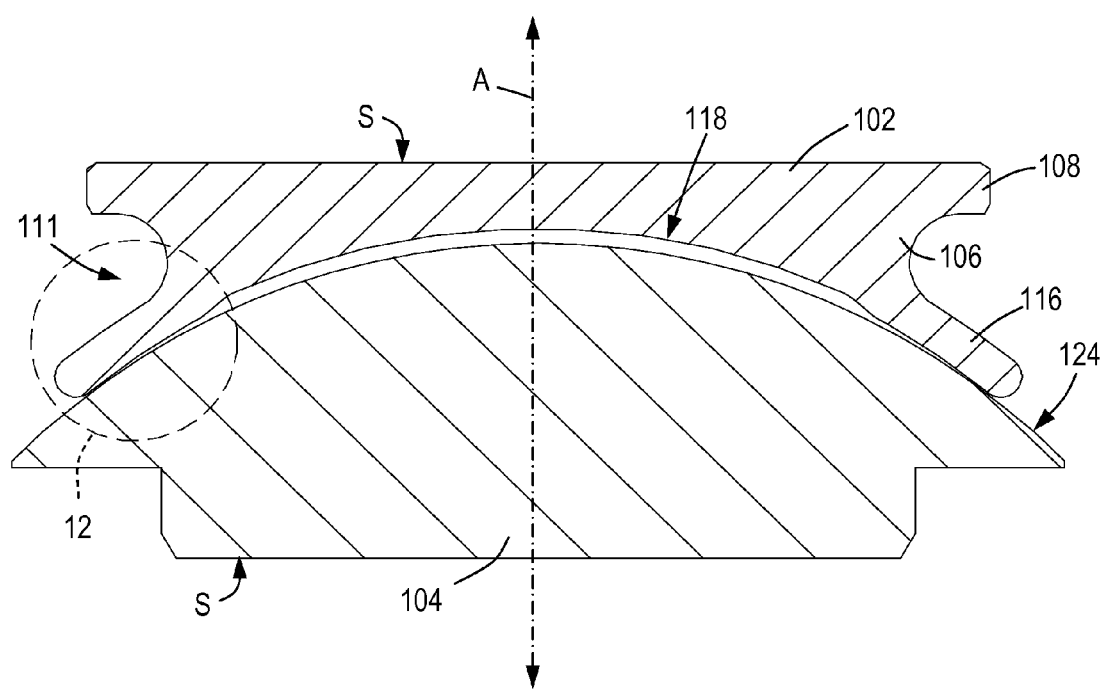
FIG. 10 is a cross-sectional view of the prosthetic joint of FIG. 9 in an unloaded condition.
Figure 11:
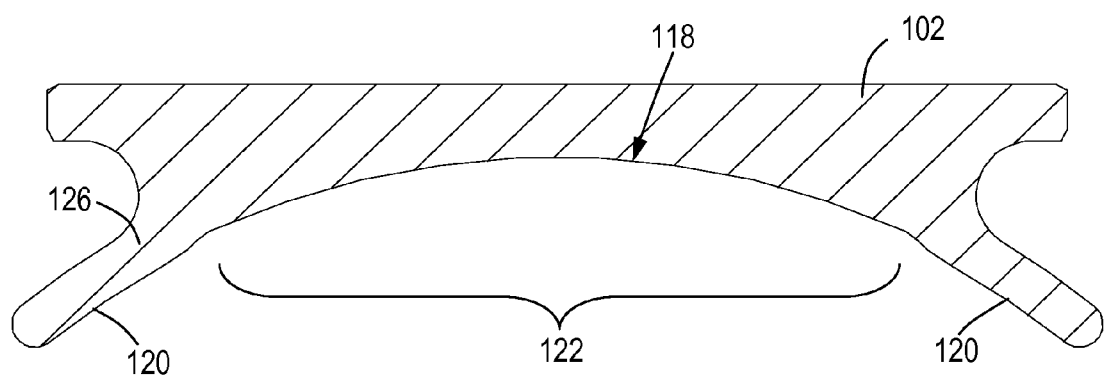
FIG. 11 is a cross-sectional view of one of the members of the prosthetic joint of FIG. 9.

FIGS. 9-14 illustrate a prosthetic joint 100 comprising first and second members 102 and 104. The illustrated prosthetic joint 100 is particularly adapted for a spinal application, but it will be understood that the principles described herein may be applied to any type of prosthetic joint. Both of the members 102 and 104 may be bone-implantable, meaning they include osseointegration surfaces, labeled "S", which are surfaces designed to be infiltrated by bone growth to improve the connection between the implant and the bone. Osseointegration surfaces may be made from materials such as TRABECULAR METAL, textured metal, or sintered or extruded implant integration textures, as described above. As shown in FIG. 10, a central axis "A" passes through the centers of the first and second members 102 and 104 and is generally representative of the direction in which external loads are applied to the joint 100 in use. In the illustrated examples, the first and second joint members are bodies of revolution about this axis, but the principles of the present invention also extend to shapes that are not bodies of revolution.

The first member 102 includes a body 106 with a perimeter flange 116 extending in a generally radially outward direction at one end. Optionally, a disk-like base 108 may be disposed at the end of the body 106 opposite the flange 116, in which case a circumferential gap 111 will be defined between the base 106 and the flange 116. The first member 102 is constructed from a rigid material. As used here, the term "rigid" refers to a material which has a high stiffness or modulus of elasticity. Nonlimiting examples of rigid materials having appropriate stiffness for the purpose of the present invention include stainless steels, cobalt-chrome alloys, titanium, aluminum, and ceramics. By way of further example, materials such as polymers would generally not be considered "rigid" for the purposes of the present invention. Generally, a rigid material should have a modulus of elasticity of about $0.5 \times 10^6$ psi or greater. Collectively, one end of the body 106 and the flange 116 define a wear-resistant, concave first contact surface 118. As used herein, the term "wear-resistant" refers to a material which is resistant to surface material loss when placed under load. Generally the wear rate should be no more than about 0.5 μm (0.000020 in.) to about 1.0 μm (0.000040 in.) per million cycles when tested in accordance with ASTM Guide F2423. As a point of reference, it is noted that any of the natural joints in a human body can easily experience one million operating cycles per year. Nonlimiting examples of wear-resistant materials include solid metals and ceramics. Known coatings such as titanium nitride, chrome plating, carbon thin films, and/or diamond-like carbon coatings may be used as a face layer to impart wear resistance to the first contact surface 118. Optionally, the first contact surface 118 could comprise a substantially thicker face layer (not shown) of a wear-resistant material such as ultra-high molecular weight (UHMW) polyethylene.

Figure 14:
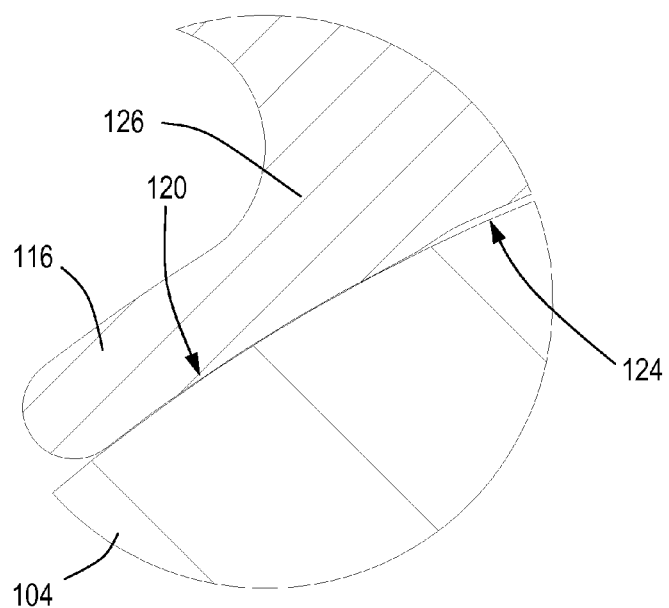
FIG. 14 is an enlarged view of a portion of FIG. 13.
Figure 15:
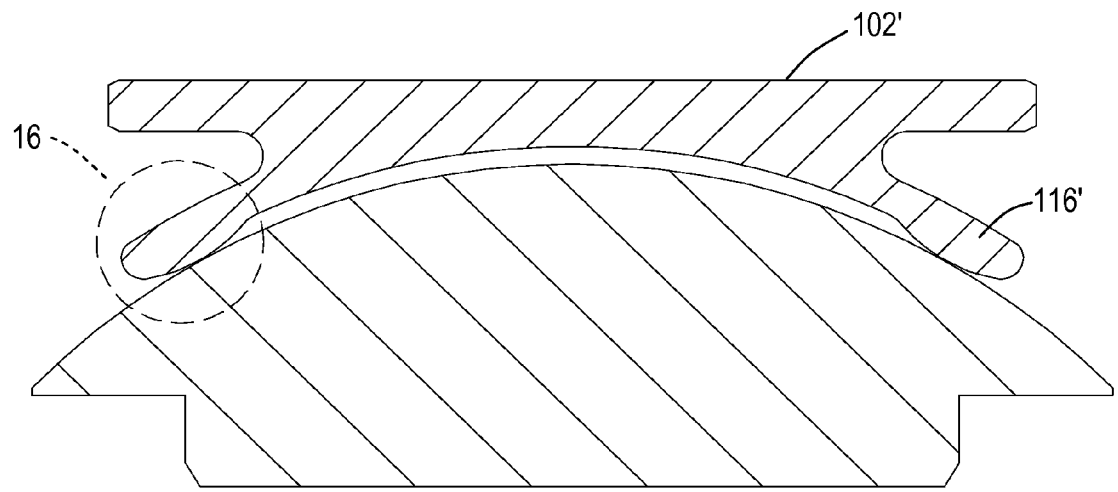
FIG. 15 is a cross-sectional view of an alternative joint member.
Figure 16:
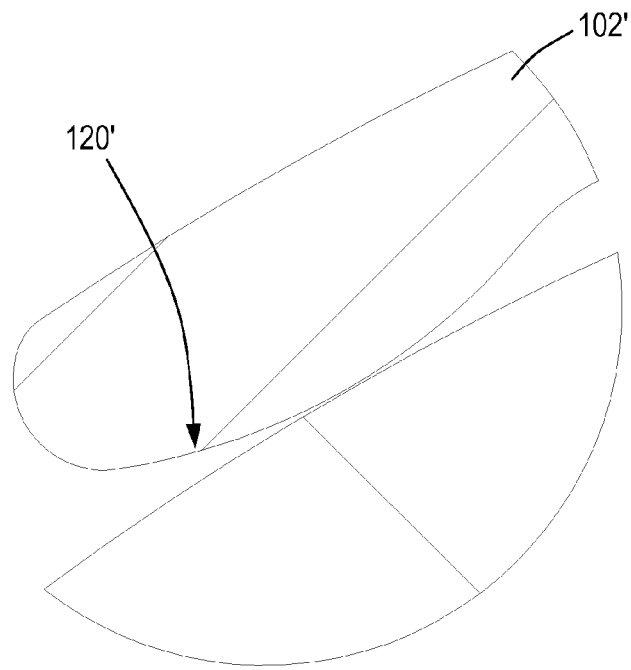
FIG. 16 is an enlarged view of a portion of FIG. 15.

The first contact surface 118 includes a protruding peripheral rim 120 (see FIG. 11), and a recessed central portion 122, which may also be considered a "pocket" or a "relief". As used herein, the term "recessed" as applied to the central portion 122 means that the central portion 122 lies outside of the nominal exterior surface of the second member 104 when the joint 100 is assembled. The terms "recessed" and "protruding" as used herein are opposite in meaning to one another. For example, the peripheral rim 120 protrudes relative to a nominal surface defined by the central portion 122, and the central portion 122 is recessed relative to the rim 120. In one configuration, shown in FIGS. 9-14, and best seen in FIG. 11, the rim 120 is concave, with the radius of curvature being quite high, such that the cross-sectional shape of the surface of the rim 120 approaches a straight line. FIGS. 15 and 16 show another configuration of a joint member 102' with a flange 116' in which the rim 120' has a convex-curved cross-sectional shape. The cross-sectional shape of the rim may be flat or curved as necessary to suit a particular application.

The annular configuration of first contact surface 118 with the protruding rim 120 results in a configuration which permits only pivoting and rotational motion, and is statically and dynamically determinate for the life of the joint 100. In contrast, prior art designs employing mating spherical shapes, even very accurate shapes, quickly reach a statically and dynamically indeterminate condition after use and wear. This condition accelerates wear, contributes to the fretting corrosion wear mechanism, and permits undesired lateral translation between the joint members.

The second member 104 is also made from a rigid material and has a wear-resistant, convex second contact surface 124. The first and second contact surfaces 118 and 124 bear directly against each other so as to transfer axial and lateral loads from one member to the other while allowing pivoting motion between the two members 102 and 104.

Nominally the first and second members 102 and 104 define a "ring" or "band" contact interface therebetween. In practice it is impossible to achieve surface profiles completely free of minor imperfections and variations. If the first and second members 102 and 104 were both completely rigid, this would cause high Hertzian contact stresses and rapid wear. Accordingly, an important feature of the illustrated joint 100 is that the flange 116 (and thus the first contact surface 118) of the first member 102 is conformable to the second contact surface 124 when the joint is placed under load.

Figure 12:
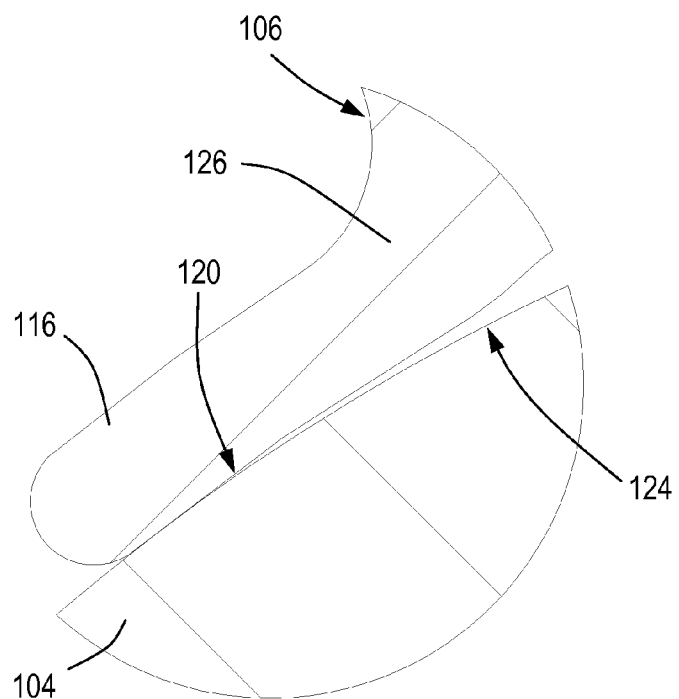
FIG. 12 is an enlarged view of a portion of FIG. 10.
Figure 13:
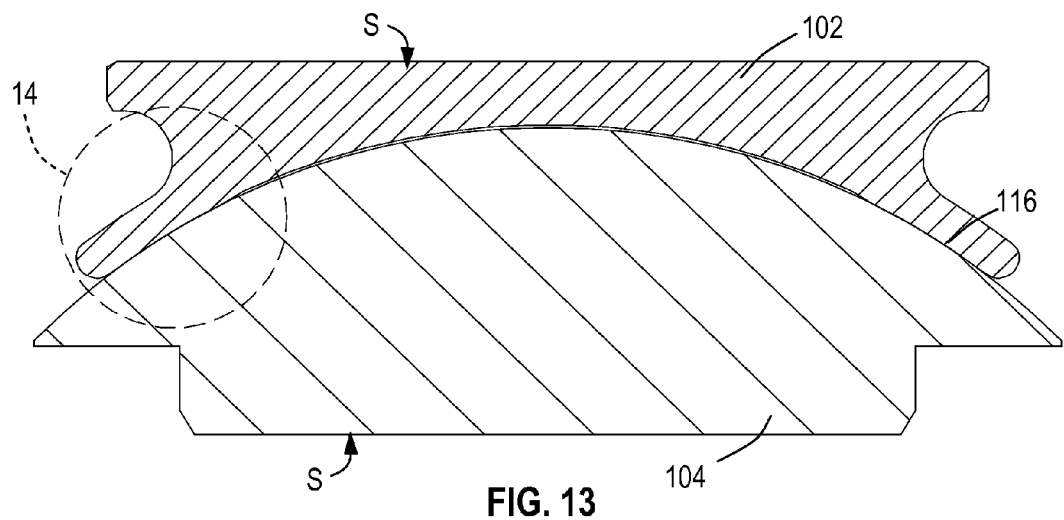
FIG. 13 is a cross-sectional view of the prosthetic joint of FIG. 9 in a loaded condition.

FIGS. 10 and 12 show a cross-sectional view of the flange 116 in an unloaded condition or free shape. It can be seen that the distal end of the rim 120 contacts the second contact surface 124, while the inboard end of the rim 120 (i.e. near where the flange 116 joins the body 106) does not. FIGS. 13 and 14 show the flange 116 in a deflected position or loaded shape, where substantially the entire section width of the rim 120 contacts the second contact surface 124, resulting in a substantially increased contact surface area between the two members 102 and 104, relative to the free shape. The rim 120' of the joint member 102' (see FIG. 16) is similarly conformable; however, given the curved cross-sectional shape, the total amount of surface contact area remains substantially constant in both loaded and unloaded conditions, with the rim 120' undergoing a "rolling" or "rocking" motion as the loading changes.

The conformable nature of the flange 116 is explained in more detail with reference to FIGS. 24 through 30. As noted above, the first member 102 has a flange 116 and a concave first contact surface 118. The second member 104 has a convex second contact surface 124. When assembled and in use the joint 100 is subject, among other loads, to axial loading in the direction of the arrows labeled "F" in FIG. 24 (i.e. along axis "A" of FIG. 10). As previously stated, it is impossible in practice for either of the contact surfaces 118 or 124 to be perfect surfaces (i.e. a perfect sphere or other curve or collection of curves). It is believed that in most cases that a defect such as a protrusion from the nominal contact surface of just 0.00127 mm (0.00005 in.), that is, 50 millionths of an inch, or larger, would be sufficient to cause fretting corrosion and failure of a metal-on-metal joint constructed to prior art standards. A defect may include a variance from a nominal surface shape as well as a discontinuity in the contact surface. Defects may arise through a variety of sources such as manufacturing, installation, and/or operating loads in the implanted joint.

Figure 25:
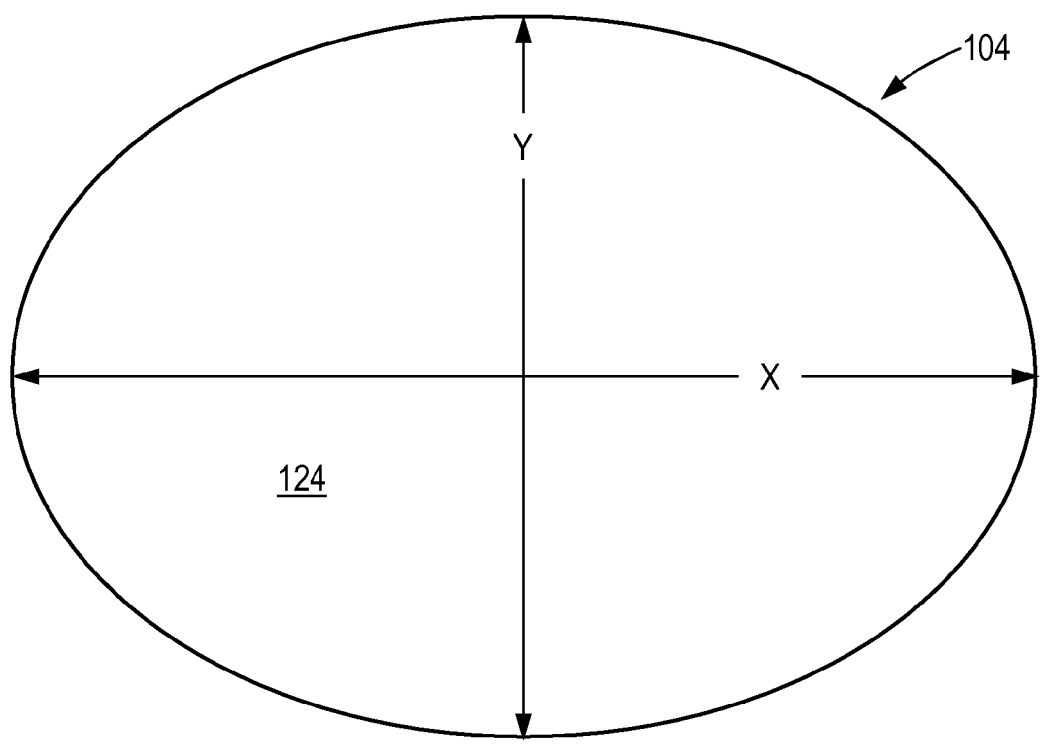
FIG. 25 is a top plan view of one of the joint members shown in FIG. 24.
Figure 26:
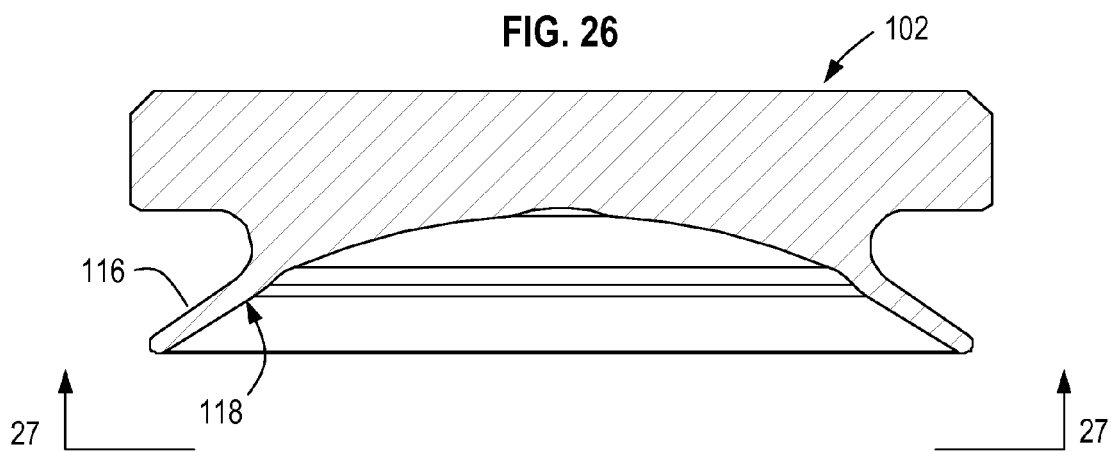
FIG. 26 is a cross-sectional view of one of the joint members shown in FIG. 24.
Figure 27:
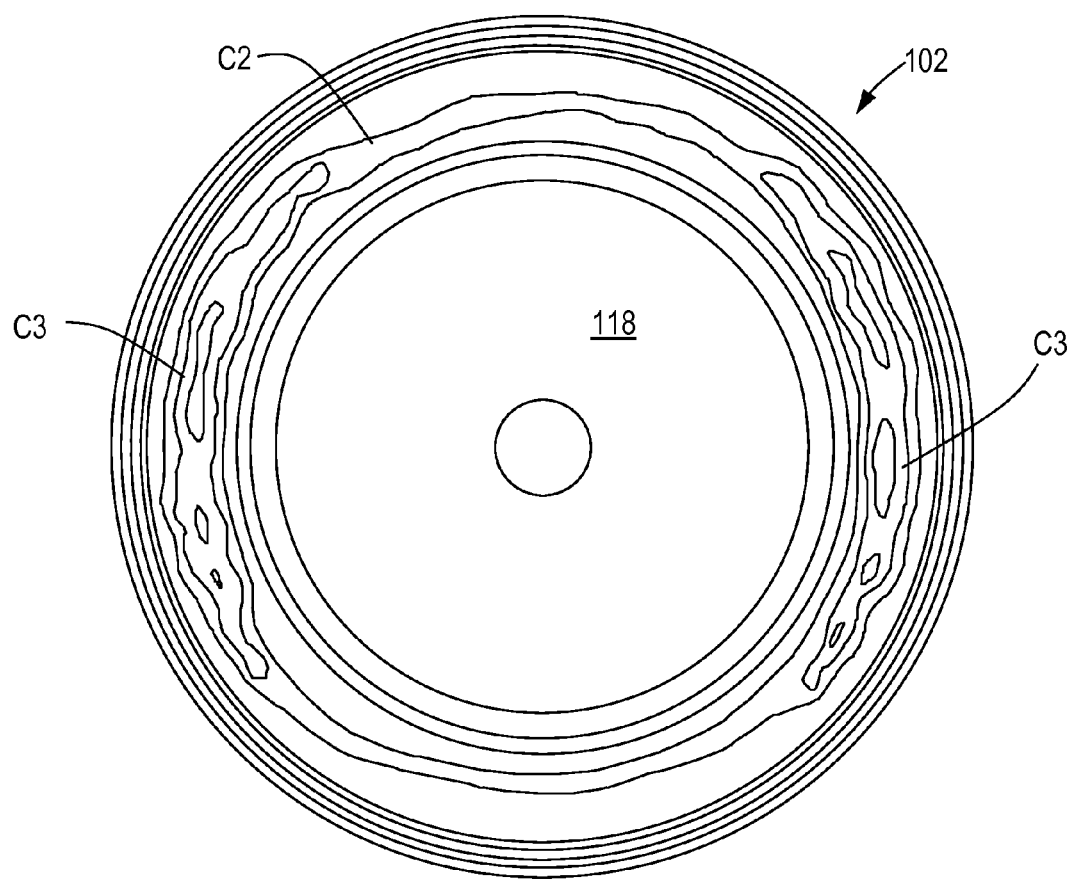
FIG. 27 is a contact stress plot of the joint member shown in FIG. 26.

FIG. 25 shows the second member 104 which in this particular example varies from a nominal shape in that it is elliptical rather than circular in plan view. The elliptical shape is grossly exaggerated for illustrative purposes. For reference, the dimensions of the second member 104 along the major axis labeled "X" is about 0.0064 mm (0.00025 in.) larger than its dimension along the minor axis labeled "Y". When assembled and loaded, the flange 116 conforms to the imperfect second contact surface 124 and deflects in an irregular shape. In other words, in addition to any uniform deflection which may be present, the deflected shape of the flange 116 includes one or more specific locations or portions that are deflected towards or away from the nominal free shape to a greater or lesser degree than the remainder of the flange 116. Most typically the deflected shape would be expected to be non-axisymmetric. For example, the deflection of the flange 116 at points located at approximately the three o'clock and nine o'clock positions is substantially greater than the deflection of the remainder of the flange 116. As a result, the contact stress in that portion of the first contact surface 118 is relieved. FIG. 27 is a plan view plot (the orientation of which is shown by arrow in FIG. 26) which graphically illustrates the expected contact stresses in the first contact surface 118 as determined by analytical methods. The first contour line "C2" shows that a very low level of contract stress is present around the entire perimeter of the first contact surface 118. This is because the entire first contact surface 118 is in contact with the second contact surface 124. Another contour line "C3" represents the areas of maximum contact stress corresponding to the protruding portions of the elliptical second contact surface 124.

Figure 28:
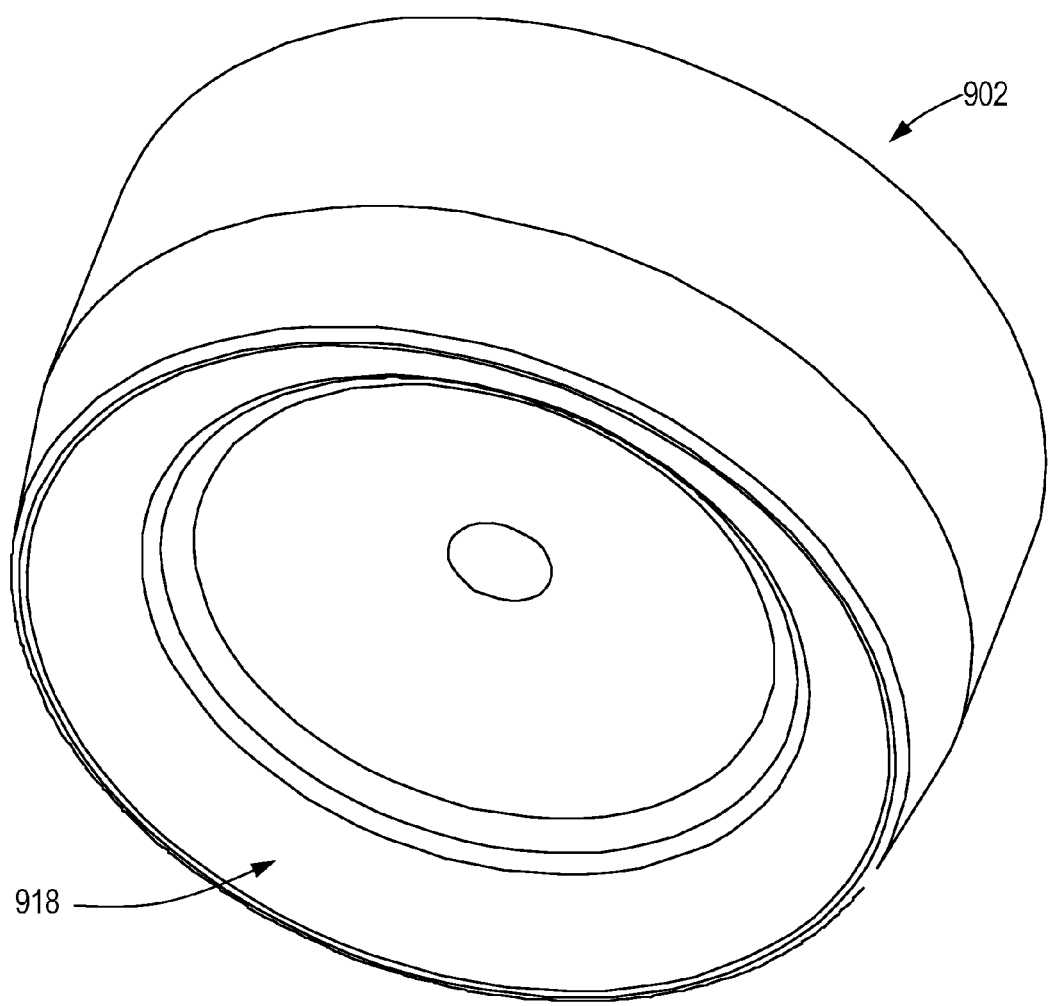
FIG. 28 is a perspective view of a rigid joint member used for comparison purposes.
Figure 29:
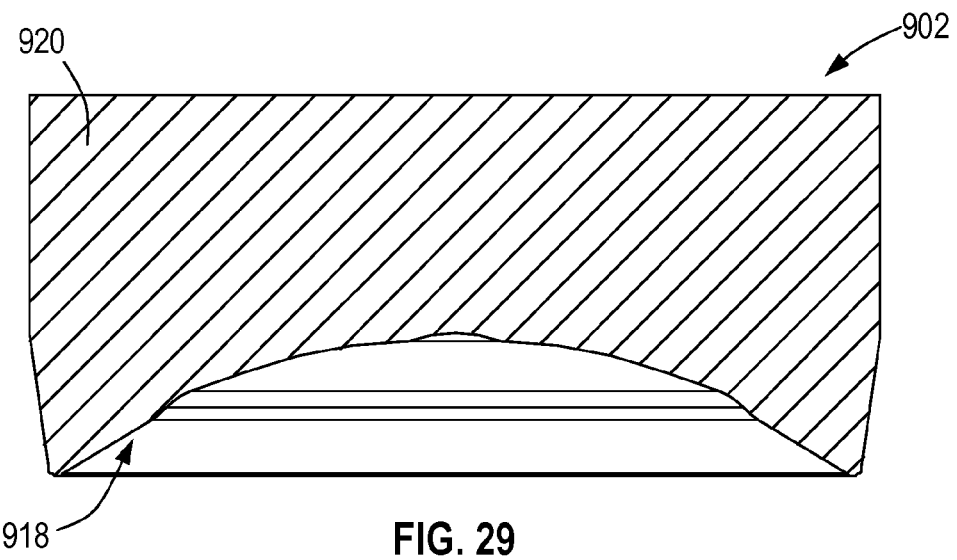
FIG. 29 is a cross-sectional view of the joint member shown in FIG. 28.
Figure 30:
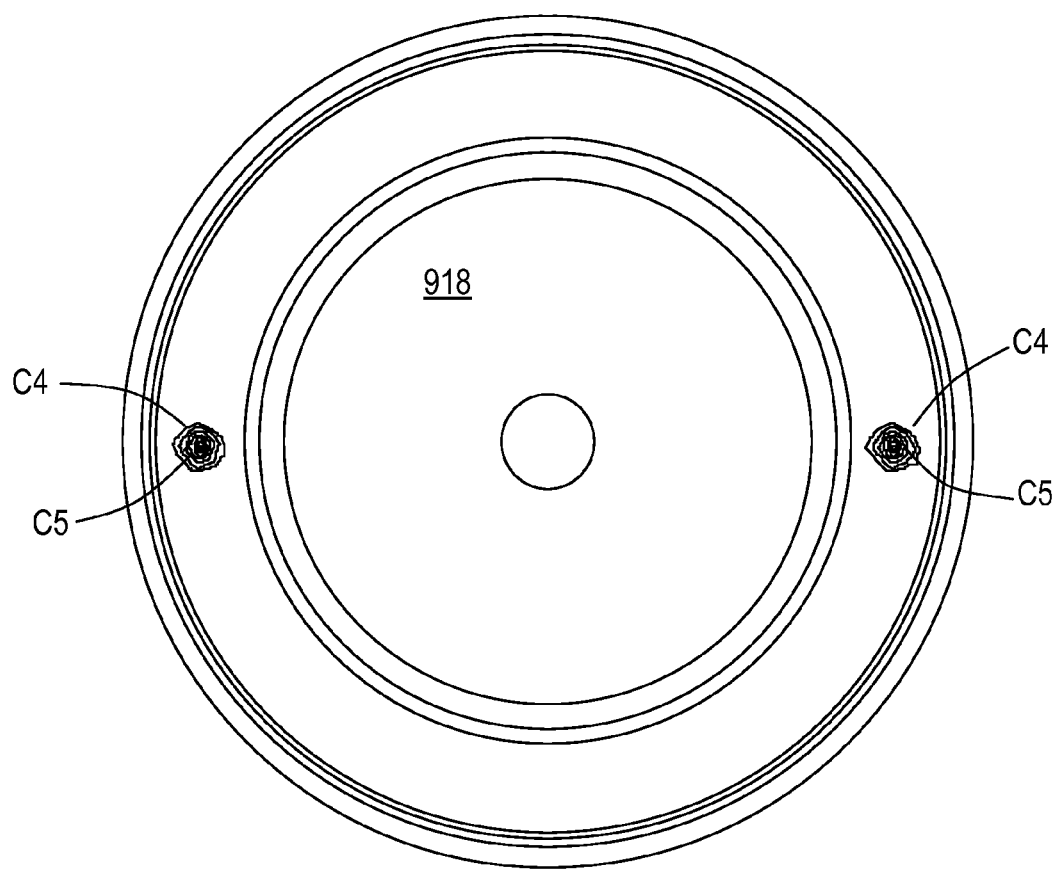
FIG. 30 is a contact stress plot of the joint member shown in FIG. 29.

For comparative purposes, FIGS. 28 and 29 depict a member 902 constructed according to prior art principles. The member 902 has a contact surface 918 with an identical profile and dimensions of the first contact surface 118 of the first member 102. However, consistent with the prior art, the member 902 has a massive body 920 behind the entire contact surface 918, rendering the entire member 902 substantially rigid. FIG. 30 graphically illustrates the expected contact stresses in the contact surface 918 as determined by analytical methods, when the member 902 is assembled and placed in contact with the second member 104, using the same applied load as depicted in FIG. 27. Because of the rigidity of the member 902, a "bridging" effect is present wherein contact between the contact surfaces (one of which is circular in plan view, and the other of which is elliptical) effectively occurs at only two points, located at approximately the three o'clock and nine o'clock positions. A first contour line "C4" shows two discrete areas where the lowest level of contract stress is present. These lines are not contiguous because there is no contact in the remaining area of the contact surfaces (for example at the six o'clock and twelve o'clock positions). Another contour line "C5" represents the areas of maximum contact stress. Analysis shows a peak contact stress having a magnitude of two to twenty times (or more) the peak contact stress of the inventive joint as shown in FIG. 27.

To achieve this controlled deflection, the flange 116 is thin enough to permit bending under working loads, but not so thin as to allow material yield or fatigue cracking The deflection is opposed by the elasticity of the flange 116 in bending, as well as the hoop stresses in the flange 116. To achieve long life, the first member 102 is sized so that stresses in the flange 116 will be less than the endurance limit of the material, when a selected external load is applied. In this particular example, the joint 100 is intended for use between two spinal vertebrae, and the design average axial working load is in the range of about 0 N (0 lbs.) to about 1300 N (300 lbs.). These design working loads are derived from FDA-referenced ASTM and ISO standards for spinal disc prostheses. In this example, the thickness of the flange 116, at a root 126 where it joins the body 106 (see FIG. 12) is about 0.4 mm (0.015 in.) to about 5.1 mm (0.200 in.), where the outside diameter of the flange 116 is about 6.4 mm (0.25 in.) to about 7.6 cm (3.0 in.).

Figure 17:
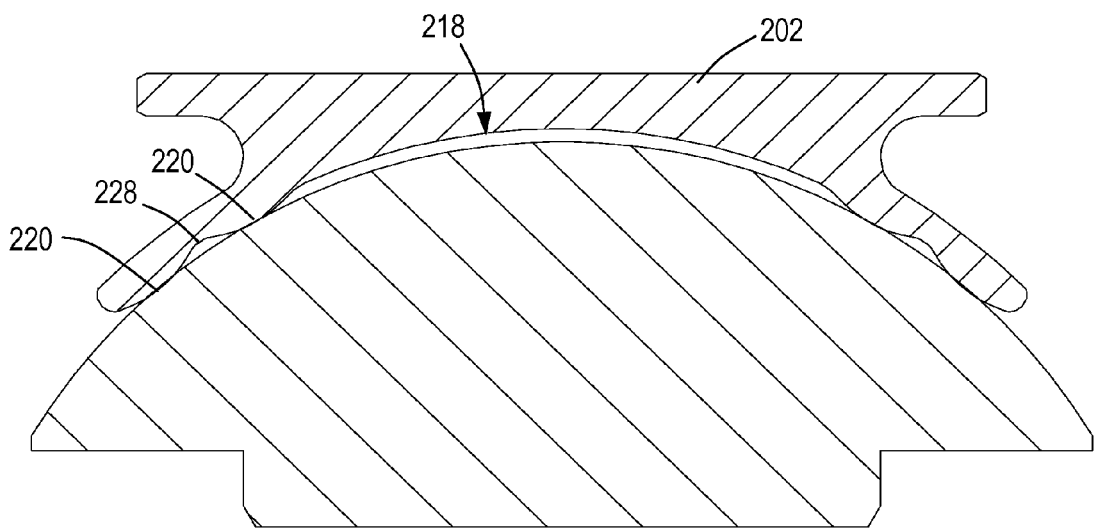
FIG. 17 is a cross-sectional view of another alternative joint member.

The joint members may include multiple rims. For example, FIG. 17 illustrates a joint member 202 where the first contact surface 218 includes two protruding rims 220, with a circumferential groove or relief area 228 therebetween. The presence of multiple rims increases the contact surface areas between the two joint members.

Figure 18:
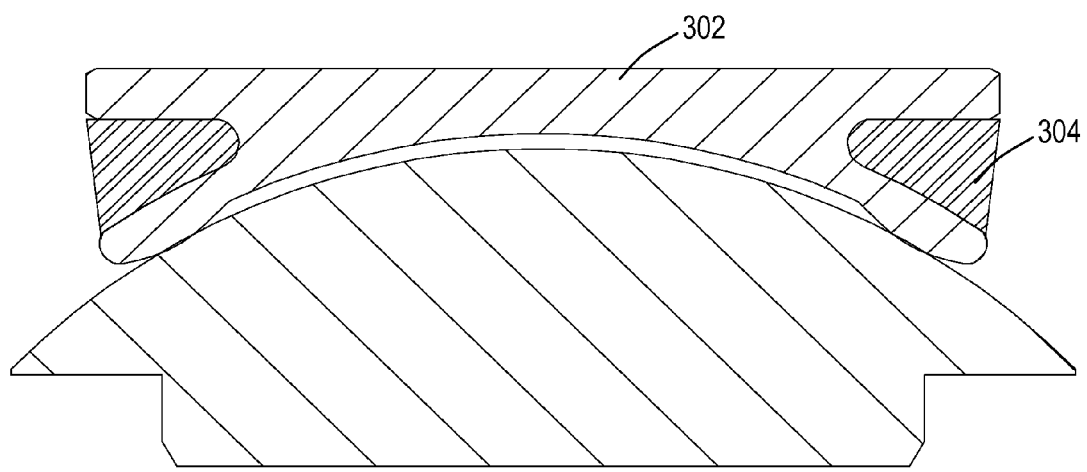
FIG. 18 is a cross-sectional view of another alternative joint member including a filler material.

If present, the circumferential gap between the flange and the base of the joint member may be filled with resilient nonmetallic material to provide damping and/or additional spring restoring force to the flange. FIG. 18 illustrates a joint member 302 with a filler 304 of this type. Examples of suitable resilient materials include polymers, natural or synthetic rubbers, and the like.

Figure 19:
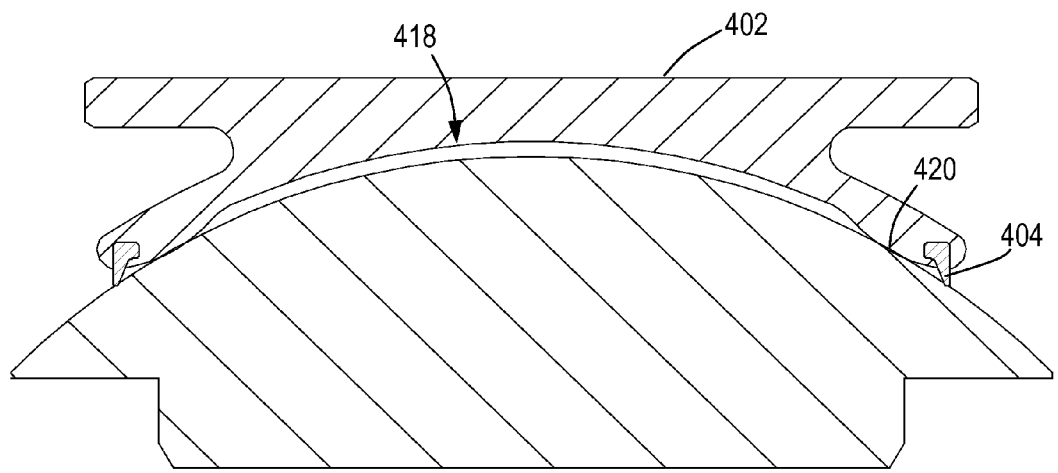
FIG. 19 is a cross-sectional view of another alternative joint member including a wiper seal.

As discussed above, the joint may incorporate a wiper seal. For example, FIG. 19 illustrates a joint member 402 with a resilient wiper seal 404 protruding from the rim 420 of the first contact surface 418. The wiper seal 404 keeps particles out of the contact area (seal void), while containing working fluid (natural or synthetic). The seal geometry is intended to be representative and a variety of seal characteristics may be employed; such as a single lip seal, a double or multiple lip seal. A pad or wiper seal may be made from a variety of material options. Different seal mounting options may be used, for example a lobe in shaped groove as shown in FIG. 18, a retaining ring or clamp, adhesion substance. The seal may also be incorporated into the contact face of the interface zone.

Figure 20:
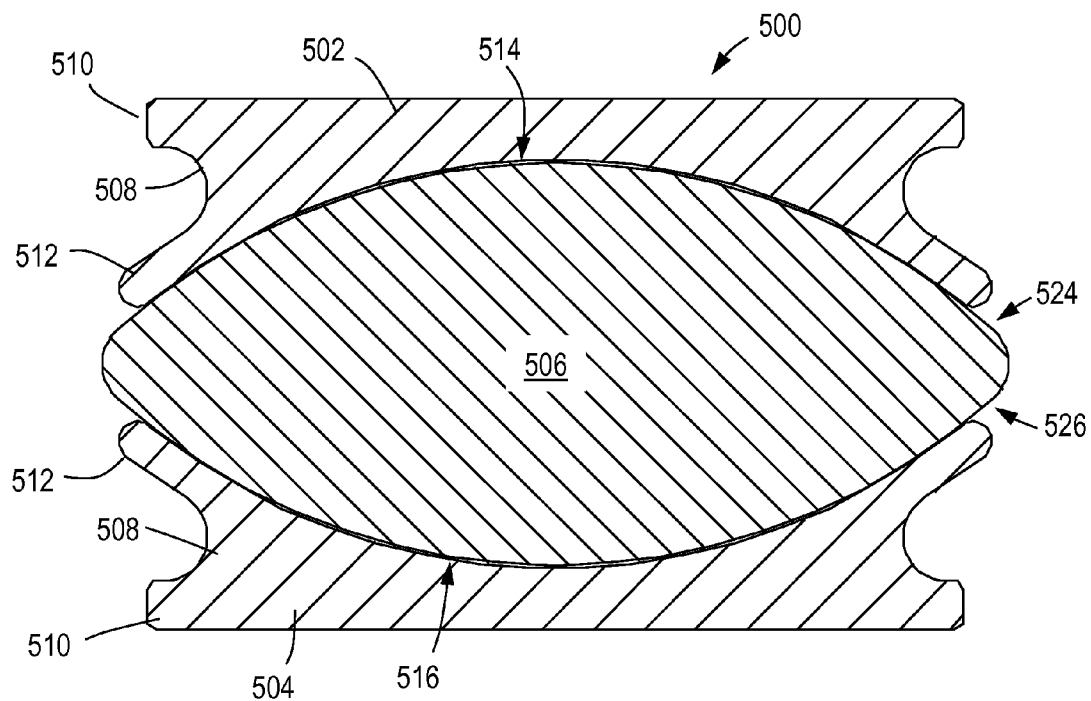
FIG. 20 is a cross-sectional view of another alternative prosthetic joint.

The joint construction described above can be extended into a three-part configuration. For example, FIG. 20 illustrates a prosthetic joint 500 having first, second, and third members 502, 504, and 506. The first and second members 502 and 504 are similar in construction to the first member 102 described above, and each includes a body 508, an optional disk-like base 510, and a flange 512. The flanges 512 define wear-resistant concave first and second contact surfaces 514 and 516, each of which includes a protruding peripheral rim, and a recessed central portion as described above. The third member 506 has a double-convex shape defining opposed wear-resistant, convex third and fourth contact surfaces 524 and 526. The first and second 514 and 516 bear against the third and fourth contact surfaces 524 and 526, respectively, so as to transfer axial (i.e. compression) and lateral loads between the first and second members 502 and 504 through the third member 506, while allowing pivoting motion between the members 502, 504, and 506. The first and second contact surfaces 514 and 516 are conformal to the third and fourth contact surfaces 524 and 526 as described in more detail above.

Figure 21:
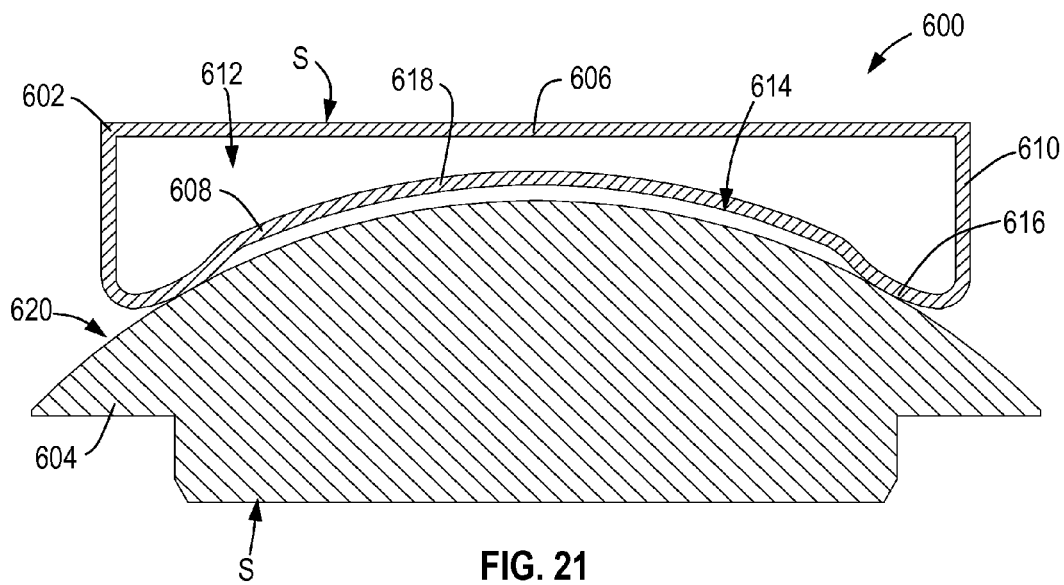
FIG. 21 is a cross-sectional view of a prosthetic joint constructed in accordance with another aspect of the present invention.

FIG. 21 illustrates an alternative prosthetic joint 600 comprising first and second members 602 and 604 constructed from rigid materials. Both of the members 602 and 604 may be bone-implantable, meaning they include osseointegration surfaces, labeled "S", as described in more detail above.

The first member 602 is hollow and includes a disk-like base 606 and a cup 608, interconnected by a peripheral wall 610. An interior cavity 612 is defined between the base 606 and the cup 608. The cup 608 is constructed from a rigid material and defines a wear-resistant, concave first contact surface 614. The first contact surface 614 includes a protruding peripheral rim 616, and a recessed central portion 618, which may also be considered a "pocket" or a "relief". The rim 616 may have a conical or curved cross-sectional shape. The interior cavity 612 may be filled with resilient nonmetallic material to provide damping and/or additional spring restoring force to the flange. Examples of suitable resilient materials include polymers, natural or synthetic rubbers, and the like.

The second member 604 is constructed from a rigid material and has a wear-resistant, convex second contact surface 620. The first and second contact surfaces 614 and 616 bear directly against each other so as to transfer axial and lateral loads from one member to the other while allowing pivoting motion between the two members 602 and 604.

As described above with reference to the prosthetic joint 100, the cup 606 of the first member 602 is thin enough to permit bending under working loads, but not so thin as to allow material yield or fatigue cracking. The first contact surface 614 is thus conformable to the second contact surface 620 when the prosthetic joint 600 is placed under external load.

Figure 22:
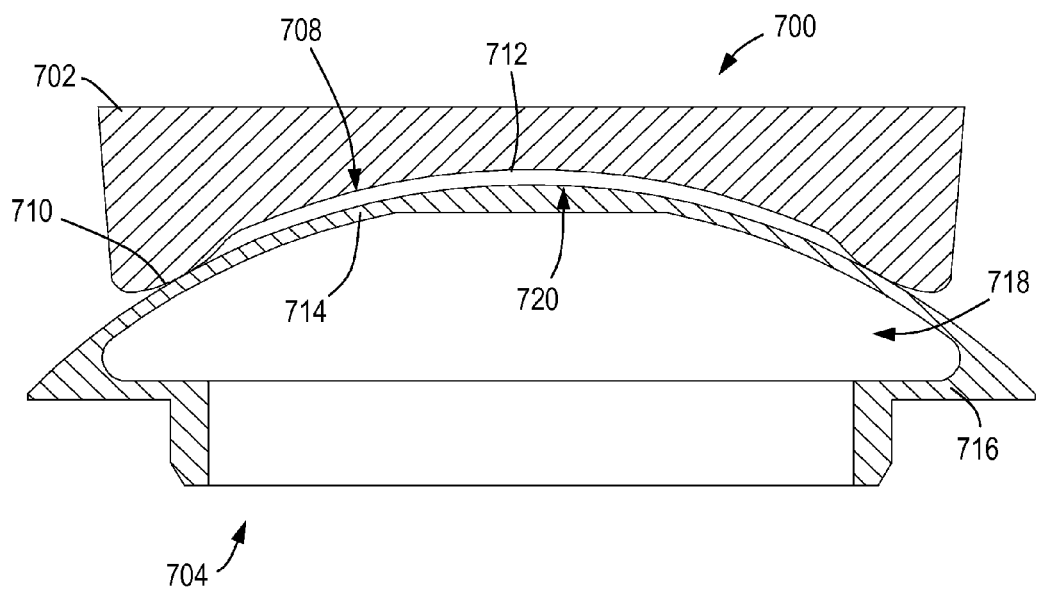
FIG. 22 is a cross-sectional view of a prosthetic joint constructed in accordance with yet another aspect of the present invention.

An inverted configuration of hollow members is also possible. For example, FIG. 22 illustrates a prosthetic joint 700 comprising first and second members 702 and 704, both constructed of rigid materials. The first member 702 is solid and includes a wear-resistant, concave first contact surface 708. The first contact surface 708 includes a protruding peripheral rim 710, and a recessed central portion 712, which may also be considered a "pocket" or a "relief".

The second member 704 is hollow and includes a dome 714 connected to a peripheral wall 716. An interior cavity 718 is defined behind the dome 714. The dome 714 defines a wear-resistant, convex second contact surface 720, which is shaped and sized enough to permit bending under working loads, but not so as to allow material yield or fatigue cracking The second contact surface 720 is thus conformable to the first contact surface 708 when the prosthetic joint 700 is placed under external load.

The first and second contact surfaces 708 and 720 bear directly against each other so as to transfer axial and lateral loads from one member to the other while allowing pivoting motion between the two members 702 and 704.

Figure 23:
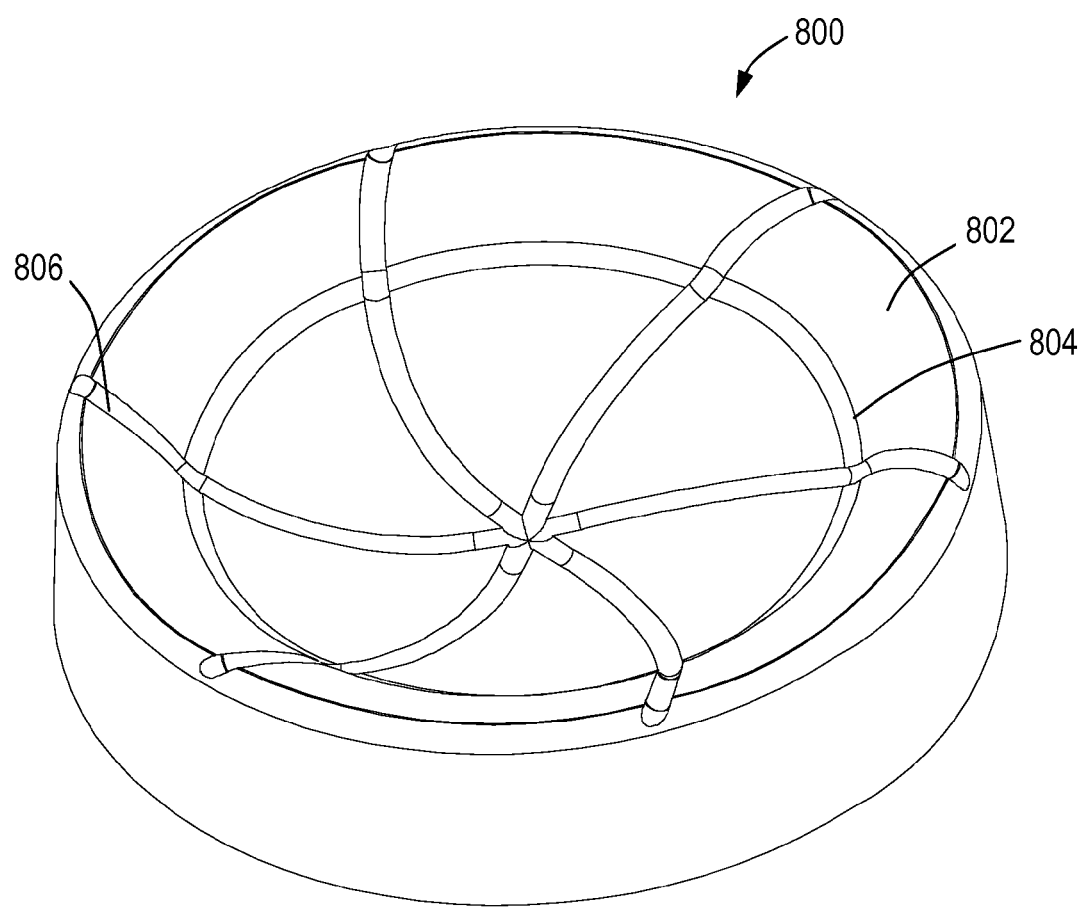
FIG. 23 is a perspective view of a joint member having a grooved surface.
Figure 24:
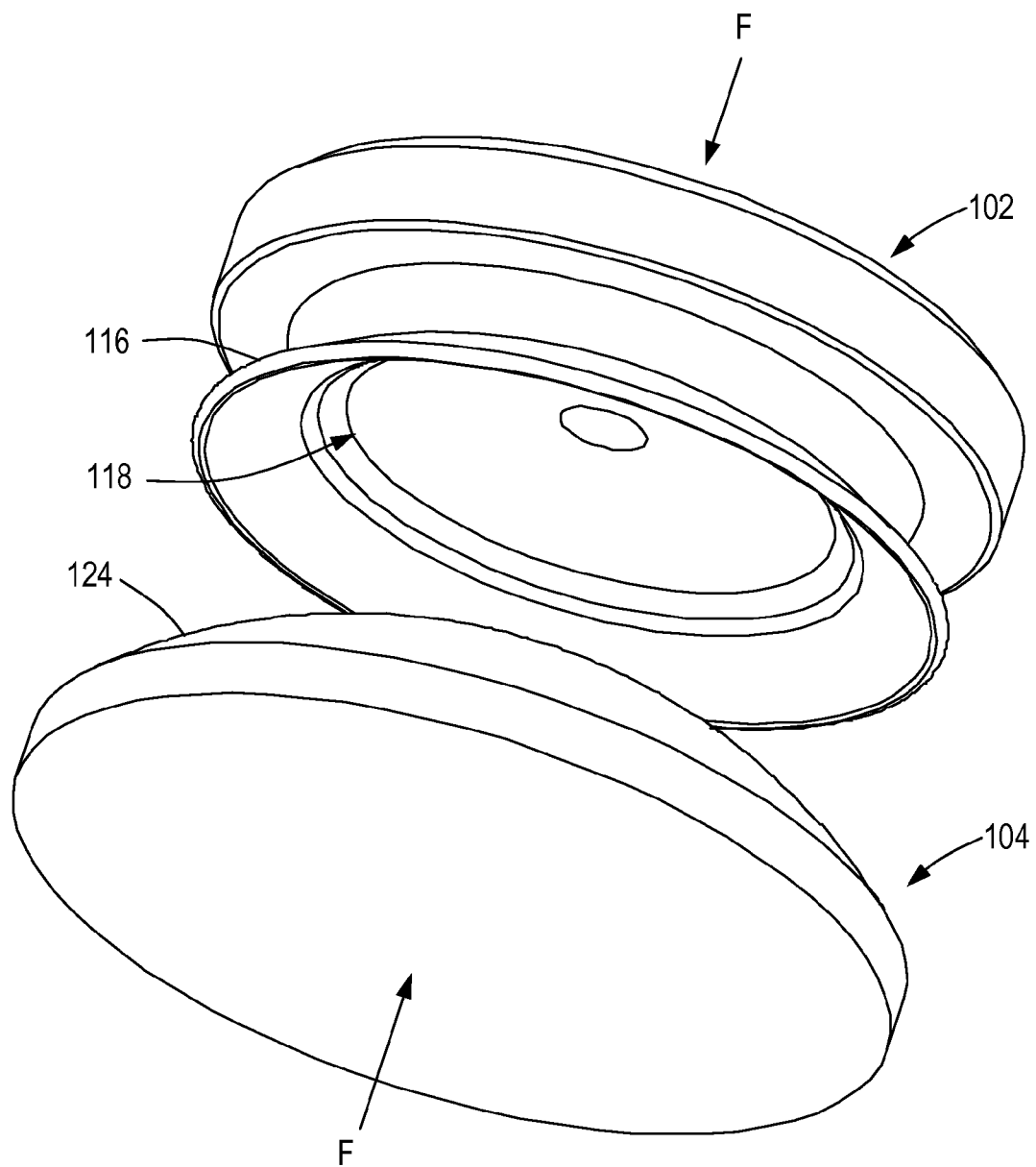
FIG. 24 is a exploded perspective view of two mating joint members.

Any of the contact surfaces described above may be provided with one or more grooves formed therein to facilitate flow of fluid or debris. For example, FIG. 23 illustrates a joint member 800 including a concave contact surface 802. The contact surface 802 includes a circular groove 804, and plurality of generally radially-extending grooves 806 which terminate at the center of the contact surface 802 and intersect the circular groove 804.

Figure 31:
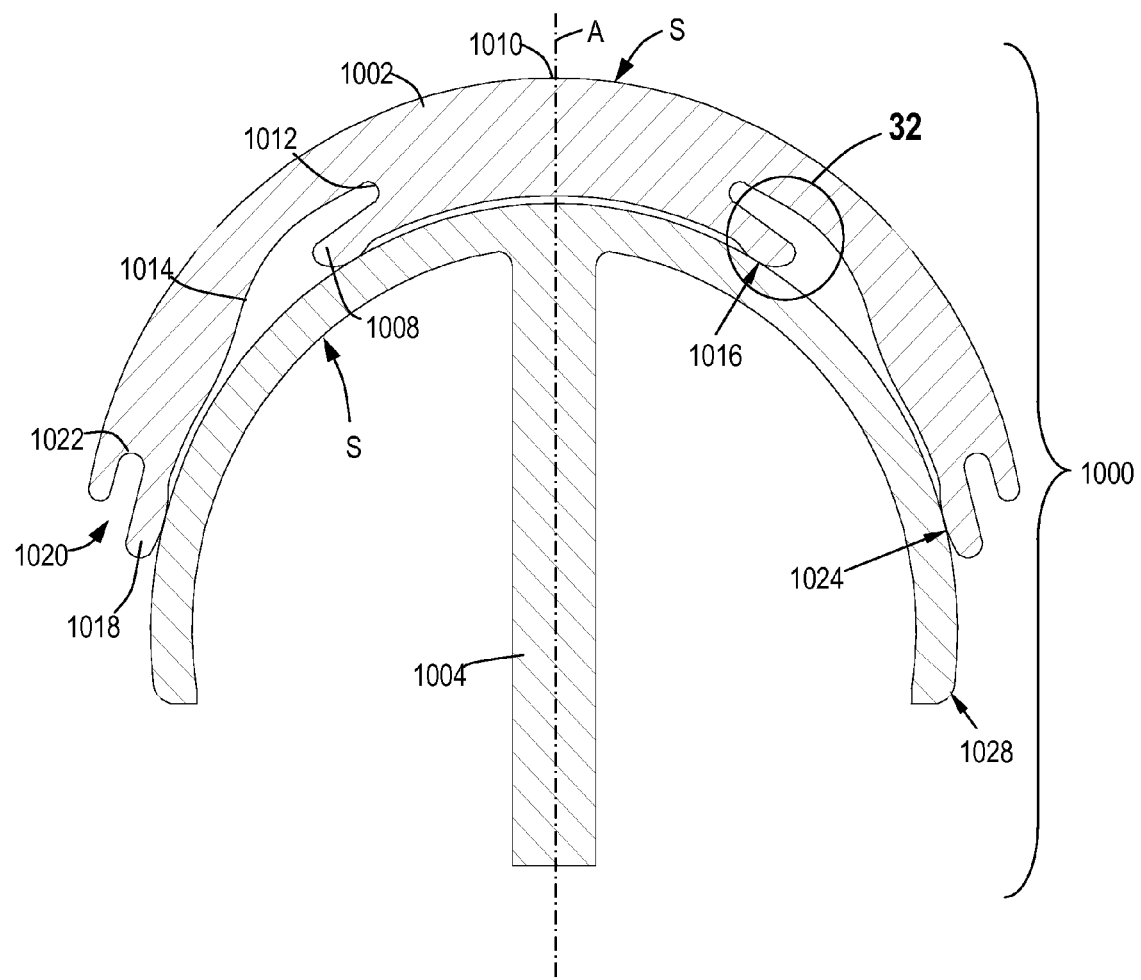
FIG. 31 is a cross-sectional view of a prosthetic joint constructed in accordance with another aspect of the present invention.
Figure 32:
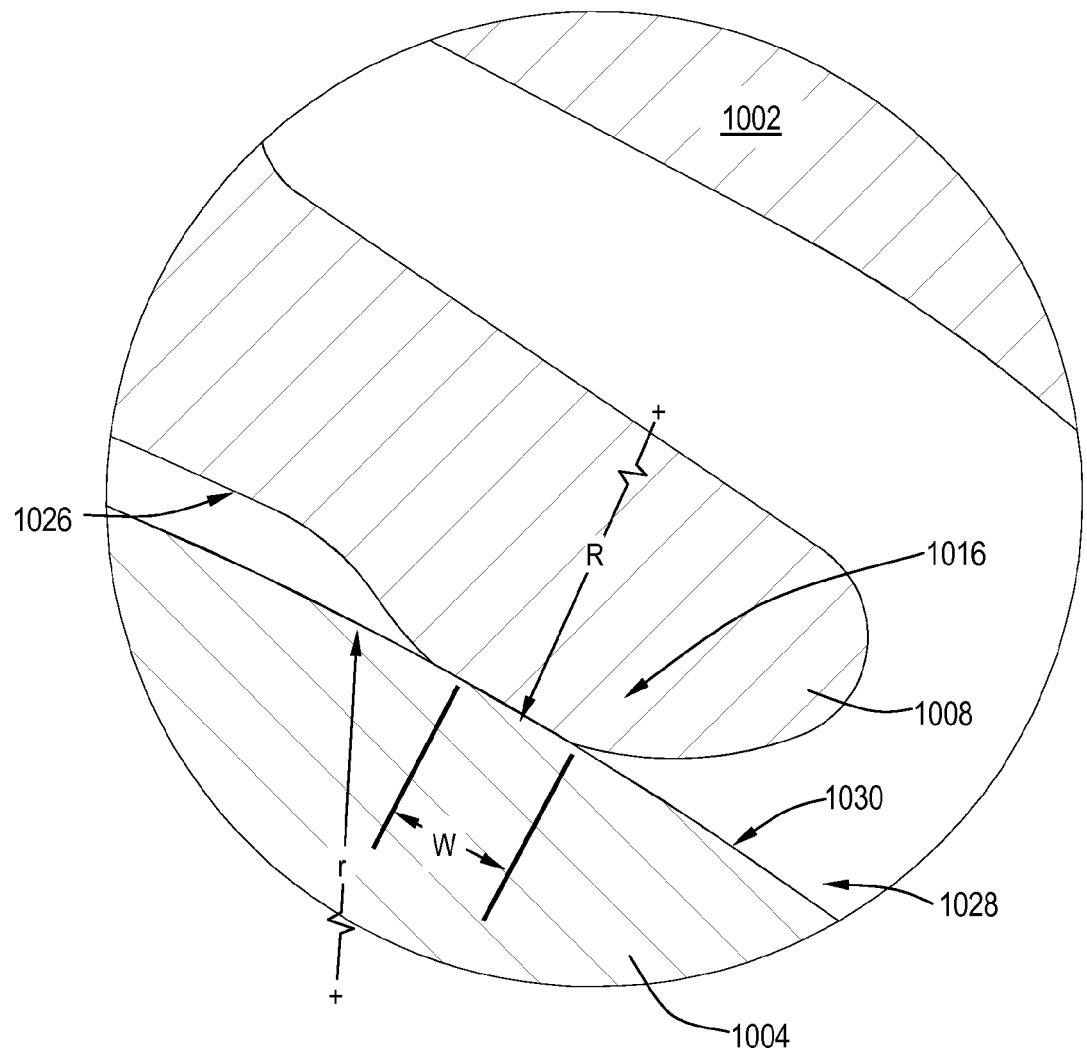
FIG. 32 is an enlarged view of a portion of the joint shown in FIG. 31.
Figure 33:
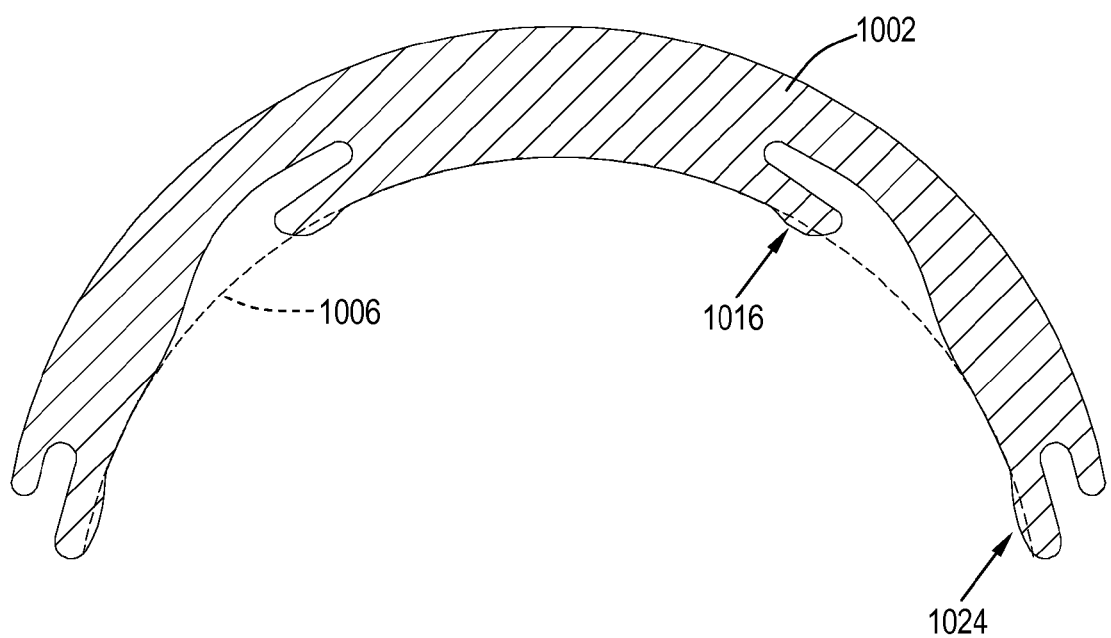
FIG. 33 is a cross-sectional view of a cup member of the joint shown in FIG. 31.

FIGS. 31-33 illustrate an alternative prosthetic joint 1000 comprising first and second members 1002 and 1004. The illustrated prosthetic joint 1000 is particularly adapted for a ball-and-socket joint application such as is found in a human hip joint (i.e. the acetabulofemoral joint) or shoulder joint (i.e. the glenohumeral joint), but it will be understood that the principles described herein may be applied to any type of prosthetic joint. Both of the members 1002 and 1004 may be bone-implantable, meaning they include osseointegration surfaces, labeled "S", which are surfaces designed to be infiltrated by bone growth to improve the connection between the implant and the bone. Osseointegration surfaces may be made from materials such as TRABECULAR METAL, textured metal, or sintered or extruded implant integration textures, as described above. As shown in FIG. 31, a nominal central axis "A" passes through the centers of the first and second members 1002 and 1004 In the illustrated examples, the first and second joint members 1002 and 1004 are bodies of revolution about this axis, but the principles of the present invention also extend to non-axisymmetric shapes.

The first member 1002 is constructed from a rigid material as described above. The first member 1002 is concave and may generally be thought of as a "cup", although it need not have any particular degree of curvature. Its interior defines a nominal cup surface 1006 shown by the dashed line in FIG. 33. The interior includes an annular first flange 1008 which is located relatively near an apex 1010 of the first member 1002 and which extends in a generally radial direction relative to the axis A. The first flange 1008 is defined in part by an undercut groove 1012 formed in the first member 1002. A ramped surface 1014 forms a transition from the groove 1012 to the nominal cup surface 1006. The first flange 1008 includes a protruding first contact rim 1016. As used herein, the term "protruding" as applied to the first contact rim 1016 means that the first contact rim 1016 lies inside of the nominal cup surface 1006 when the joint 1000 is assembled. The first contact rim 1016 may have a curved or toroidal cross-sectional shape.

The interior also includes an annular second flange 1018 which is located at or near an outer peripheral edge 1020 of the first member 1002 and which extends in a generally axial direction relative to the axis A. The second flange 1018 is defined in part by an undercut groove 1022 formed in the first member 1002. The second flange 1018 includes a protruding second contact rim 1024. As used herein, the term "protruding" as applied to the second contact rim 1024 means that the second contact rim 1024 lies inside of the nominal cup surface 1006 when the joint 1000 is assembled. The second contact rim 1024 may have a curved or toroidal cross-sectional shape. Depending on the particular application, joint 1000 may include more than two flanges defining more than two contact rims.

In the illustrated example, the first member 1002 includes a face layer 1026 of a known coating such as titanium nitride, chrome plating, carbon thin films, and/or diamond-like carbon coatings, and/or a another substantially thicker wear-resistant material such as ultra-high molecular weight (UHMW) polyethylene. This face layer 1026 is used to impart wear resistance, as described above. The face layer 1026 may be extraordinarily thin. In this particular example, its as-applied thickness is about 0.0041 mm (0.00016 in.), or 160 millionths of an inch thick. The face layer 1026 is applied at a substantially uniform thickness over the surface profile which is defined by machined or formed features of the substrate. Alternatively, and especially if a much thicker face layer were used, the face layer could be profiled so as to define both the nominal cup surface 1006 and the first and second contact rims 1016 and 1024.

The second member 1004 is also made from a rigid material and has a wear-resistant, convex contact surface 1028. In the specific example illustrated, the second member 1004 includes a face layer 1030 of a known coating such as titanium nitride, chrome plating, carbon thin films, and/or diamond-like carbon coatings, and/or a another substantially thicker wear-resistant material such as ultra-high molecular weight (UHMW) polyethylene. This face layer 1030 is used to impart wear resistance, and may be quite thin, as described above. The first and second contact rims 1016 and 1024 bear directly against the contact surface 1028 so as to transfer axial and lateral loads from one member to the other while allowing pivoting motion between the two members 1002 and 1004.

The annular configuration of contact rims 1016 and 1024 results in a joint configuration which permits only pivoting and rotational motion, and is statically and dynamically determinate for the life of the joint 1000. In particular, the presence of the relatively widely-spaced contact rims 1016 and 1024, and the peripheral positioning of the second contact rim 1024 is highly effective in resisting any translation of the first and second members 1002 and 1004 lateral to the axis A.

Nominally the first and second contact rims 1016 and 1024 define two separate "ring" or "band" contact interfaces with the contact surface 1028 of the second member 1004. In practice it is impossible to achieve surface profiles completely free of minor imperfections and variations. If the first and second members 1002 and 1004 were both completely rigid, this would cause high Hertzian contact stresses (i.e. non-uniform contact) and rapid wear. Accordingly, an important feature of the illustrated joint 1000 is that the flanges 1008 and 1018 (and thus the contact rims 1016 and 1024) of the first member 1002 are conformable to the contact surface 1028 when the joint 1000 is placed under load. The flanges 1008 and 1018 can conform to the imperfect contact surface 1028 and deflect in an irregular shape. In other words, in addition to any uniform deflection which may be present, the deflected shape of the flanges 1008 and 1018 can include one or more specific locations or portions that are deflected towards or away from the nominal free shape to a greater or lesser degree than the remainder of the flanges 1008 and 1018. To achieve this controlled deflection, the flanges 1008 and 1018 are thin enough to permit bending under working loads, but not so thin as to allow material yield or fatigue cracking, or to exceed the endurance limit of the material. The deflection is opposed by the elasticity of the flanges 1008 and 1018 in bending, as well as the hoop stresses in the flanges 1008 and 1018.

Figure 36:
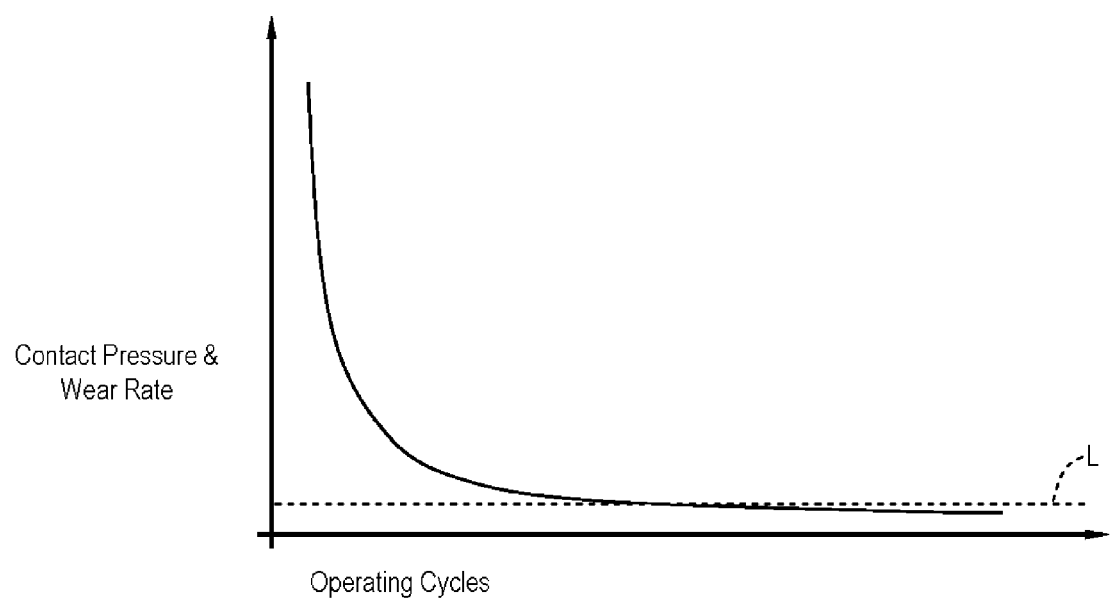
FIG. 36 is a graph showing contact pressure of the joint of FIG. 31 compared to the number of operating cycles.

The contact rims 1016 and 1024 are designed in conjunction with the contact surface 1028 to create a wear characteristic that is constantly diminishing (similar to an asymptotic characteristic). With reference to FIG. 32, the as-manufactured or initial curvatures (e.g. radii) of the first and second contact rims 1016 and 1024, denoted "R" are different from the curvature (e.g. radius) of the contact surface 1028, denoted "r". It is noted that the direction of curvature (i.e. the convexity or second derivative shape) of the first and second contact rims 1016 and 1024 may be the same as, or opposite to, that of the contact surface 1028 upon initial manufacture. In this example they are opposite. When assembled and placed under load, the annular interface between each of the contact rims 1016 and 1024 and the contact surface 1028 will have a characteristic width denoted "W", (effectively creating a contact band). The initial dimensions R and r are selected such that, even using highly wear-resistant surfaces or coatings, some wear takes place during an initial wear-in period of movement cycles. As a result, the contact band width W increases during the initial wear-in period. This increases contact area and therefore decreases contact stress for a given load. After the initial wear-in period (which preferably occurs before the joint is implanted), the contact band reaches a post wear-in width at which the contact stress is below a selected limit, below which the rate of wear in the contacting surfaces approaches a very low number or zero, consistent with a long life of the joint 1000. FIG. 36 illustrates this wear characteristic, with the limit "L" depicted as a horizontal line.

Figure 34:
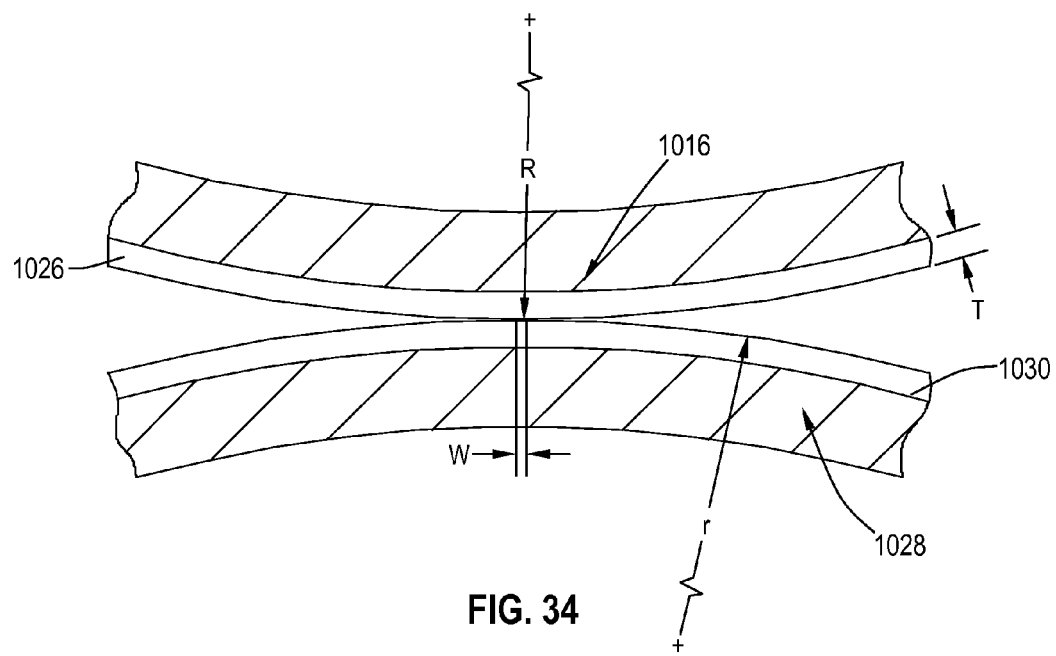
FIG. 34 is a greatly enlarged cross-sectional view of a portion of the joint shown in FIG. 31 in an initial condition.
Figure 35:
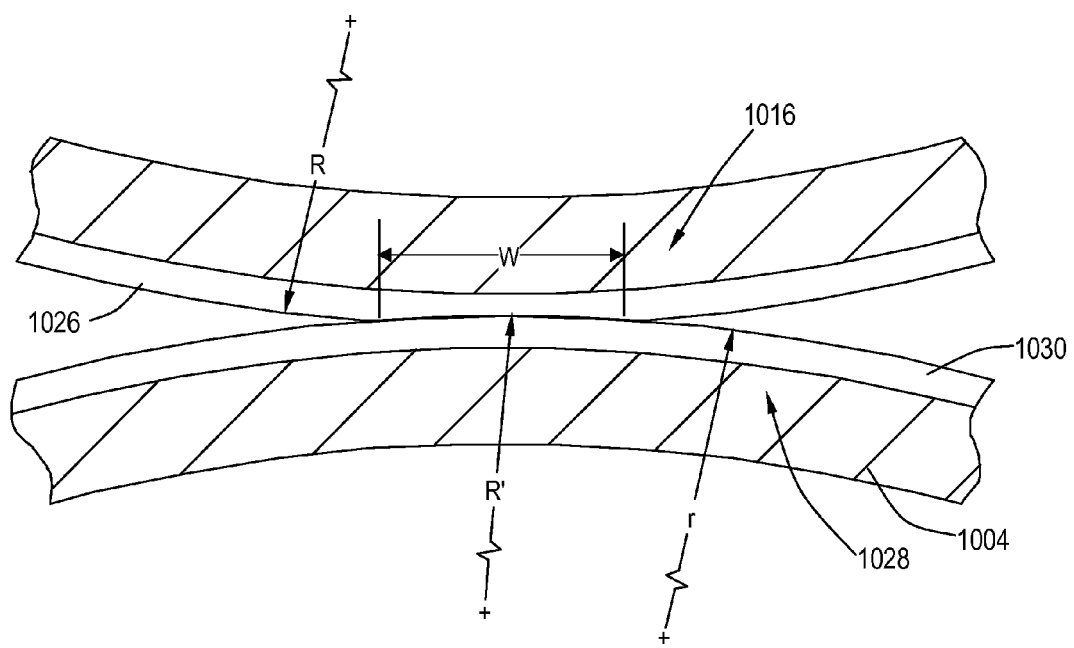
FIG. 35 is a greatly enlarged cross-sectional view of a portion of the joint shown in FIG. 31 after an initial wear-in period.

FIGS. 34 and 35 are schematic views showing the initial wear-in of the surface of the contact rim 1016 at a microscopic (or nearly microscopic) level. It will be understood that these figures are greatly exaggerated for the purposes of illustration. On initial manufacture, as shown in FIG. 34, the curvatures R and r of the contact rim 1016 and the contact surface 1028 have opposite directions. When assembled, the contact band width W is some nominal value, for example about 0.03 mm (0.001 in.), and the total thickness "T" of the face layer 1026 is at its as-applied value of about 0.0041 mm (0.00016 in.) for example. The action of the wear-in period described causes the face layer 1026 to wear to a shape complementary to the contact surface 1028. After this wear-in period the curvature of the portion of the contact rim 1016 within the contact band, denoted "R'", and the curvature r of the contact surface 1028 are in the same direction, and the values of the two curvatures are substantially the same. For example, the thickness T at the location of the contact band may decrease by about 0.0004 mm (0.000014 in.), with a corresponding increase in the width of the contact band W to about 0.2 mm (0.008 in.). Analysis shows that this increase in contact band width and surface area can reduce mean contact pressure by over 80%.

The configuration of the flanges 1008 and 1018 are important in developing the constantly diminishing wear characteristics described above. In particular, the flanges 1008 and 1018 are sized and shaped so that deflections of the contact rims 1016 and 1024 under varying load are always essentially normal to their respective tangent points on the opposing contact surface 1028, as the joint 1000 is loaded and unloaded. This ensures that the position of each of the contact bands remains constant and that the contact bands remain substantially uniform around the entire periphery of the joint 1000.

Figure 37:
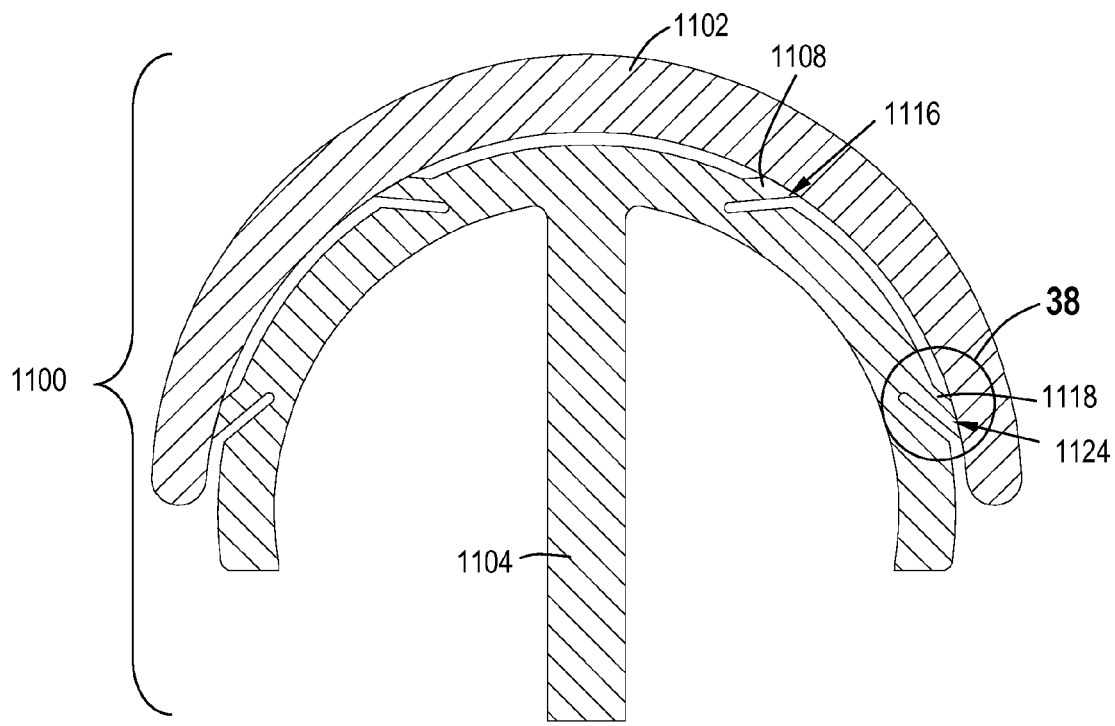
FIG. 37 is a cross-sectional view of a prosthetic joint constructed in accordance with another aspect of the present invention.
Figure 38:
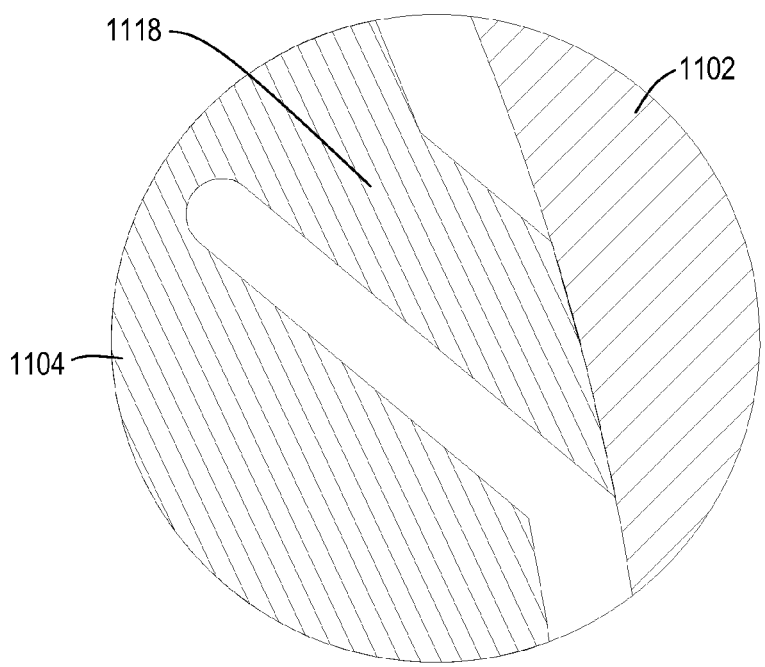
FIG. 38 is an enlarged view of a portion of the joint shown in FIG. 37

An inverted configuration of the joint described above may be used. For example, FIGS. 37 and 38 illustrate a prosthetic joint 1100 having first and second members 1102 and 1104 which are substantially similar in general construction to the members of the joint 1000 described above in terms of materials, coatings, and so for forth. However, in this joint 1100, the concave member 1102 has a contact surface without protruding rings. The convex member 1104 has first and second flanges 1108 and 1118 which define first and second contact rims 1116 and 1124 which function in the same manner that the flanges and contact rims described above.

Figure 39:
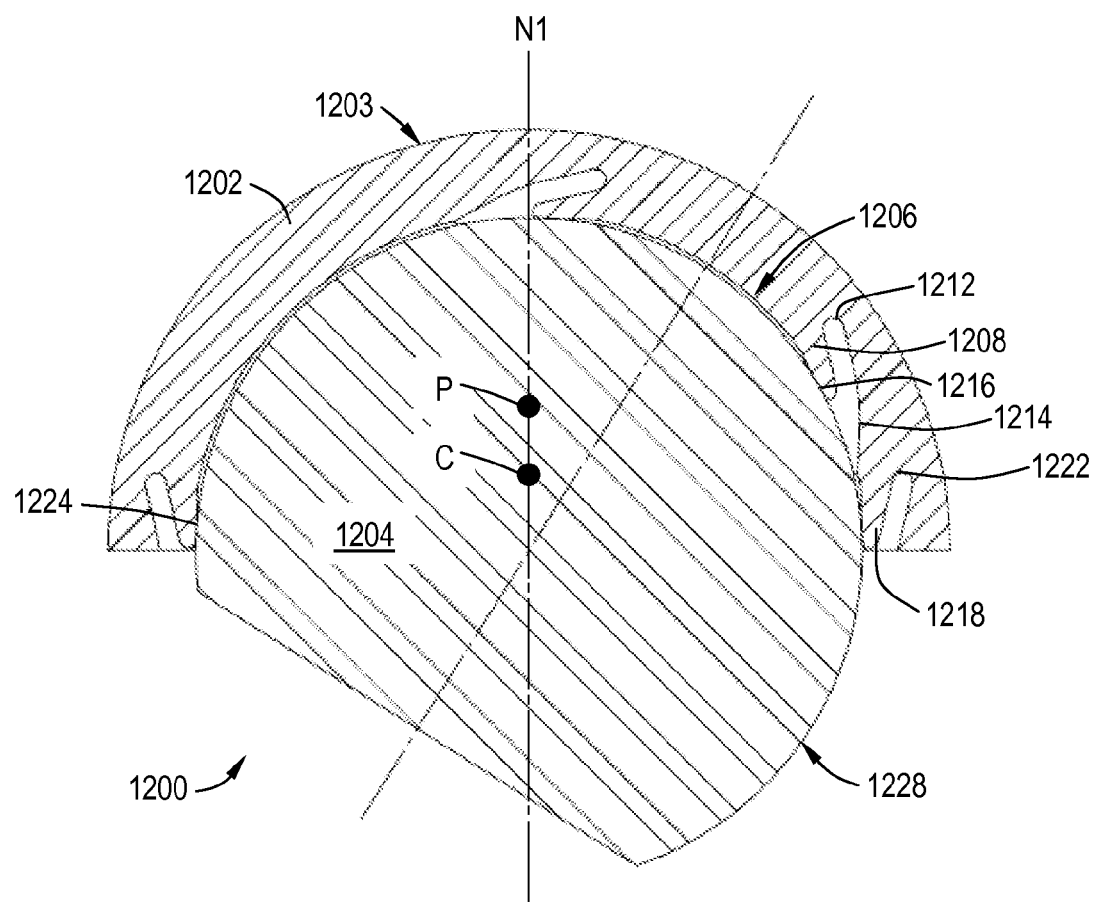
FIG. 39 is a cross-sectional view of a prosthetic joint constructed in accordance with another aspect of the present invention.

FIG. 39 illustrates an alternative prosthetic joint 1200 comprising first and second members 1202 and 1204. The illustrated prosthetic joint 1200 is generally similar in construction and function to the prosthetic joint 1000 described above, and one or both of the members 1202 and 1204 may be bone-implantable as described above.

A For purposes of explanation and illustration the first member 1202 will be described relative to a "balanced centroidal axis", labeled "N1" in FIG. 39, passing through it. As used herein, the term "balanced centroidal axis" refers to a virtual line, parallel to local gravity (i.e. a local vertical), which passes through the geometric centroid of the first member 1202, labeled "C", when the first member is in a balanced position (i.e. when there is no rotation of the first member due to unbalanced mass). It is noted that, where the first member 1202 is presumed to have a uniform density, the centroid C will be co-located with its center of mass. If the first member 1202 were suspended in a balanced condition by a point "P" vertically above the centroid C the balanced centroidal axis N1 would coincide with a local vertical axis passing through the centroid C. In the case where the first member 1202 is a body of revolution, the balanced centroidal axis N1 would coincide or nearly coincide with the generating axis of the first member 1202.

The first member 1202 is constructed from a rigid material and may generally be thought of as a "cup", as described above. Its interior defines a nominal cup surface 1206. The interior includes a cantilevered first flange 1208, defined in part by an undercut groove 1212 formed in the first member 1202. Without regard to the exact direction that the flange 1208 extends, it may be considered to be cantilevered relative to the remainder of the first member 1202. In other words, when viewed in cross-section, it is a projecting structure, that is supported at one end and carries a load at the other end or along its length. A ramped surface 1214 forms a transition from the groove 1212 to the nominal cup surface 1206. The first flange 1208 includes a protruding first contact rim 1216. The first contact rim 1216 may have a straight, curved, or toroidal cross-sectional shape.

The first flange 1208 has an angular offset relative to the balanced centroidal axis N1. In other words, the first flange 1208 is asymmetric to the balanced centroidal axis N1. This is also referred to as a "non-axisymmetric" condition. In the particular example and view shown in FIG. 39, the first flange 1208 is offset to the right side of the figure. The angular offset or asymmetric position allows the functional characteristics of the first flange 1208 to be tailored to specific operating conditions encountered by the prosthetic joint 1200. For example, the angular offset may be selected so that the first flange is aligned with an expected primary load vector.

The interior also includes a cantilevered second flange 1218 which is defined in part by an undercut groove 1222 formed in the first member 1202. The second flange 1218 includes a protruding second contact rim 1224. The second contact rim 1224 may have a straight, curved, or toroidal cross-sectional shape.

The second member 1204 is also made from a rigid material and has a wear-resistant, convex contact surface 1228. The first and second contact rims 1216 and 1224 bear directly against the contact surface 1228 so as to transfer axial and lateral loads from one member to the other while allowing pivoting motion between the two members 1202 and 1204. The annular configuration of contact rims 1216 and 1224 results in a joint configuration which permits only pivoting and rotational motion, and is statically and dynamically determinate for the life of the joint 1200.

Nominally the first and second contact rims 1216 and 1224 define two separate "ring" or "band" contact interfaces with the contact surface 1228 of the second member 1204. The flanges 1208 and 1218 (and thus the contact rims 1216 and 1224) of the first member 1202 are conformable to the contact surface 1228 when the joint 1200 is placed under load. The flanges 1208 and 1218 can conform to the imperfect contact surface 1228 and deflect in an irregular shape, in the manner described above for the joint 1200.

The facing surfaces of either or both of the first and second members 1202 and 1204 may include a face layer of a known coating such as titanium nitride, chrome plating, carbon thin films, and/or diamond-like carbon coatings, and/or a another substantially thicker wear-resistant material such as ultra-high molecular weight (UHMW) polyethylene. This face layer is used to impart wear resistance, as described above.

Figure 40:
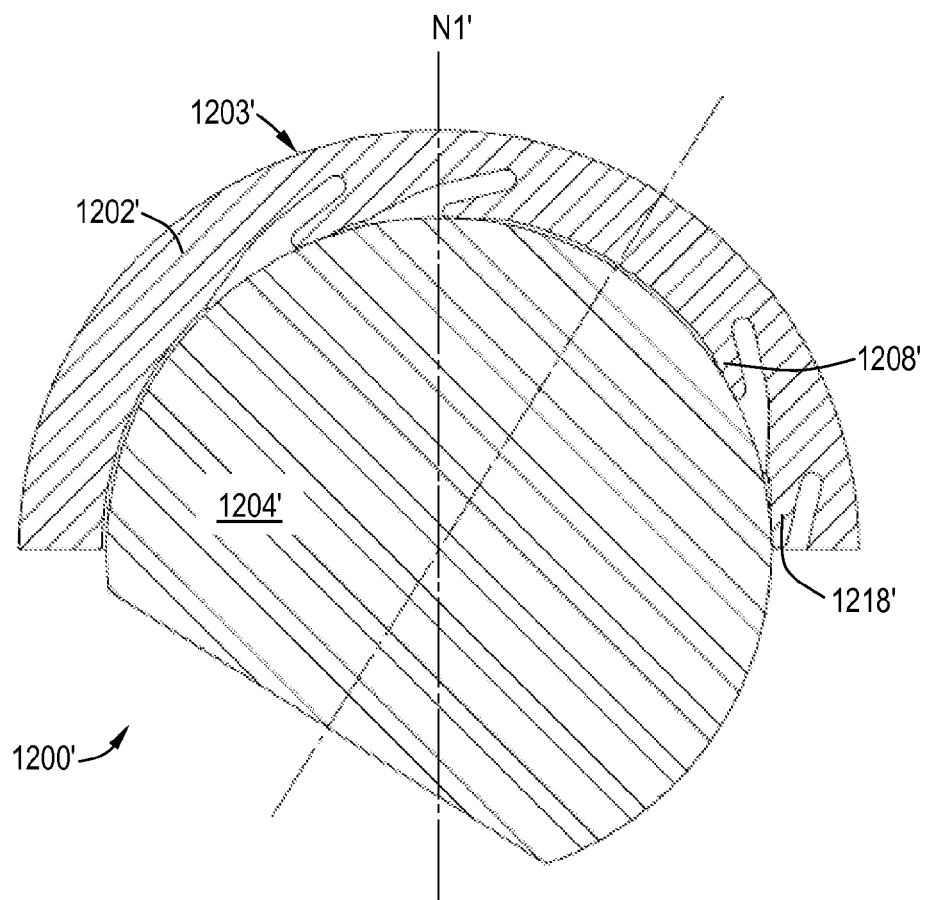
FIG. 40 is a cross-sectional view of a prosthetic joint constructed in accordance with another aspect of the present invention.

Depending on the specific application, the second flange 1218 may have an angular offset like the first flange 1208. For example, FIG. 40 illustrates a prosthetic joint 1200' substantially similar in construction to the prosthetic joint 1200, with first and second members 1202' and 1204'. The first member 1202' has a balanced centroidal axis "N1'", and first and second flanges 1208' and 1218'. The first flange 1208' is angularly offset from the balanced centroidal axis N1' (i.e. it is asymmetric relative to the balanced centroidal axis N1') and the second flange 1218 is also angularly offset from the nominal axis N1' (i.e. it is asymmetric relative to the balanced centroidal axis N1').

Figure 41:
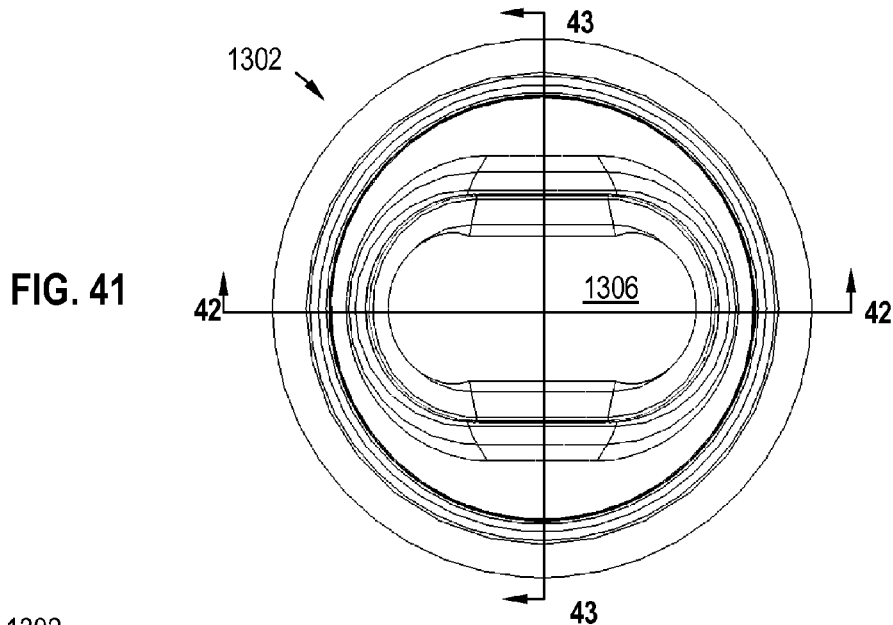
FIG. 41 is a plan view of a portion of a prosthetic joint constructed in accordance with another aspect of the present invention.
Figure 42:
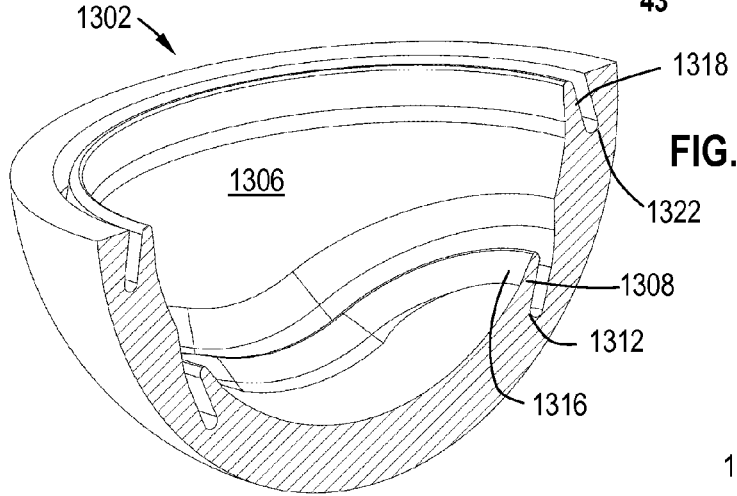
FIG. 42 is a view taken along lines 42-42 of FIG. 41.
Figure 43:
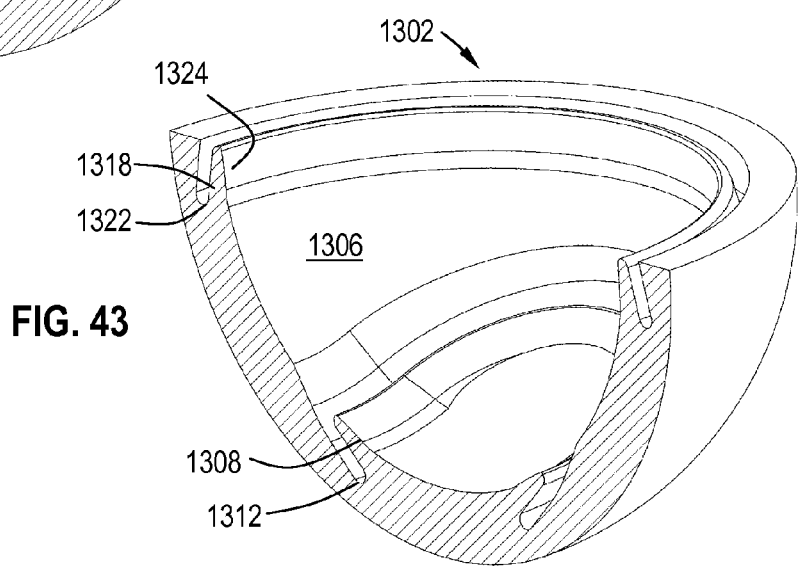
FIG. 43 is a view taken along lines 43-43 of FIG. 41.

The flange of the joint members described above need not be circular, elliptical, or another symmetrical shape in plan view, and need not lie in a single plane. For example, FIGS. 41-43 illustrate a joint member 1302. Its interior defines a nominal cup surface 1306. The interior includes a cantilevered first flange 1308, defined in part by an undercut groove 1312 formed in the first member 1302. The first flange 1308 includes a protruding first contact rim 1316. The first contact rim 1316 may have a straight, curved, or toroidal cross-sectional shape. The interior also includes a cantilevered second flange 1318 which is defined in part by an undercut groove 1322 formed in the first member 1302. The second flange 1318 includes a protruding second contact rim 1324. The second contact rim 1324 may have a straight, curved, or toroidal cross-sectional shape.

The first flange 1308 (and therefore the first contact rim 1316) have a "saddle" shape. In this particular example it has a racetrack shape in plan view, and the portions at the ends of the major axis of the racetrack shape are elevated (in the z-direction) relative to the remainder of the shape. The first contact rim 1316 is shaped so as to define a contact band in which some or all points on its surface lie on a sphere (or otherwise match the shape of the mating convex joint member described above). The second flange 1318 could have a similar saddle shape as well.

Figure 44:
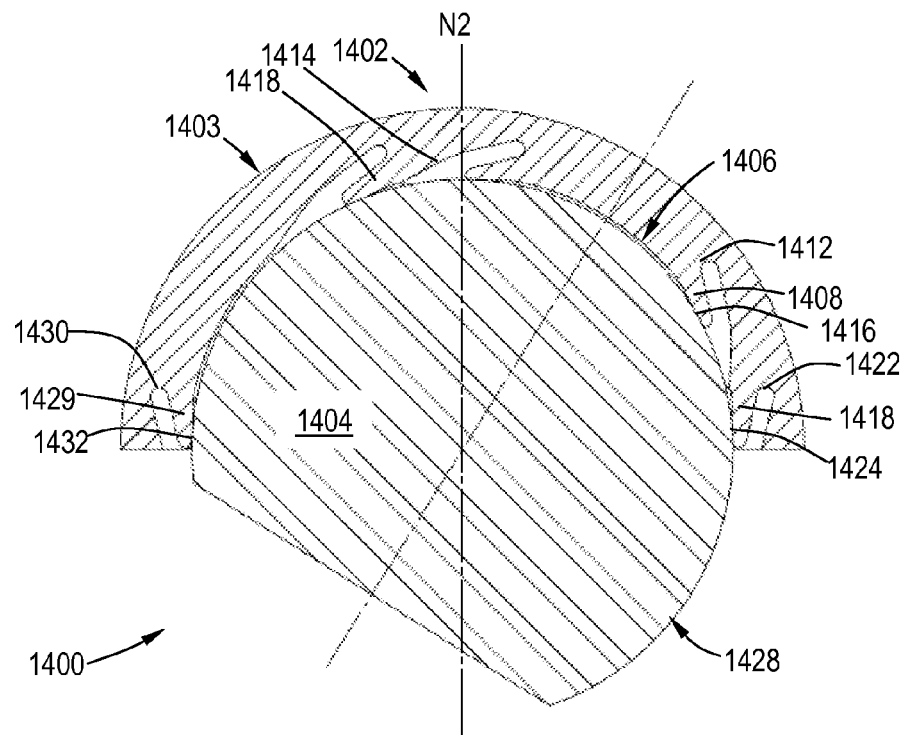
FIG. 44 is a cross-sectional view of a prosthetic joint constructed in accordance with another aspect of the present invention.
Figure 45:
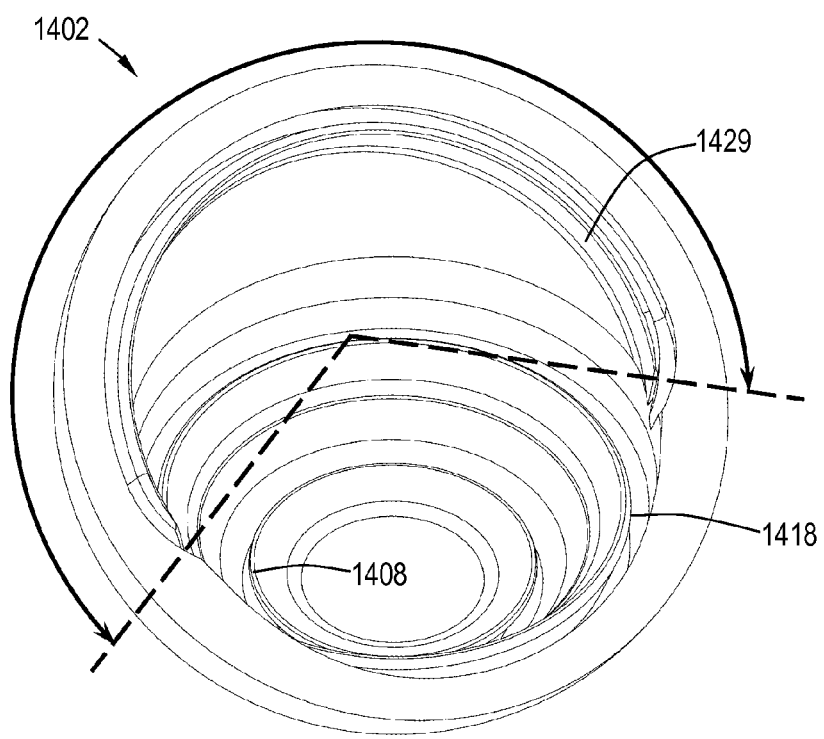
FIG. 45 is a perspective view of the prosthetic joint of FIG. 44.

The prosthetic joints described herein may include one or more flanges with an open perimeter. For example, FIGS. 44 and 45 illustrate another alternative prosthetic joint 1400 comprising first and second members 1402 and 1404. The illustrated prosthetic joint 1400 is generally similar in construction and function to the prosthetic joint 1000 described above, and one or both of the members 1402 and 1404 may bone-implantable as described above.

A balanced centroidal axis "N2", may be considered to pass through the first member 1402. This axis N2 is defined in the same manner as the balanced centroidal axis "N1" described above. The first member 1402 is constructed from a rigid material and may generally be thought of as a "cup", as described above. Its interior defines a nominal cup surface 1406. The interior includes a cantilevered first flange 1408, defined in part by an undercut groove 1412 formed in the first member 1402. A ramped surface 1414 forms a transition from the groove 1412 to the nominal cup surface 1406. The first flange 1408 includes a protruding first contact rim 1416. The first contact rim 1416 may have a straight, curved, or toroidal cross-sectional shape.

The first flange 1408 has an angular offset relative to the balanced centroidal axis N2, in other words it is asymmetric relative to the balanced centroidal axis N2. The interior also includes a cantilevered second flange 1418 which is defined in part by an undercut groove 1422 formed in the first member 1402. The second flange 1418 includes a protruding second contact rim 1424. The second contact rim 1424 may have a straight, curved, or toroidal cross-sectional shape.

In the example shown in FIGS. 44 and 45, the second flange 1418 is also angularly offset from the balanced centroidal axis N2, i.e. it is asymmetric relative to the balanced centroidal axis.

The interior also includes a cantilevered third flange 1429 which is defined in part by an undercut groove 1430 formed in the first member 1402. The third flange 1418 includes a protruding third contact rim 1432. The third contact rim 1432 may have a straight, curved, or toroidal cross-sectional shape. As best seen in FIG. 45, the third flange 1429 has an open perimeter, circumscribing less than 360 degrees. The distal ends of the third flange 1429 may be feathered away from the nominal cup surface, for example either by tapering the third flange's thickness or by tilting the distal ends outward relative to the remainder of the flange, so as not to contact the contact surface 1428 of the second member 1404.

The third flange 1429 could be symmetric or asymmetric relative to the balanced centroidal axis N2.

The second member 1402 is also made from a rigid material and has a wear-resistant, convex contact surface 1428. The first, second, and third contact rims 1416, 1424, and 1432, bear directly against the contact surface 1428 so as to transfer axial and lateral loads from one member to the other while allowing pivoting motion between the two members 1402 and 1404.

Nominally the first, second, and third contact rims 1416, 1424, and 1432 define three separate "ring" or "band" contact interfaces with the contact surface 1428 of the second member 1404. The flanges 1408, 1418, and 1429 (and thus the contact rims 1216, 1224, and 1432) of the first member 1402 are conformable to the contact surface 1428 when the joint 1400 is placed under load. The flanges 1408, 1418, and 1429 can conform to the imperfect contact surface 1428 and deflect in an irregular shape, in the manner described above for the joint 1000.

The facing surfaces of either or both of the first and second members 1402 and 1404 may include a face layer of a known coating such as titanium nitride, chrome plating, carbon thin films, and/or diamond-like carbon coatings, and/or a another substantially thicker wear-resistant material such as ultra-high molecular weight (UHMW) polyethylene. This face layer is used to impart wear resistance, as described above.

Figure 46:
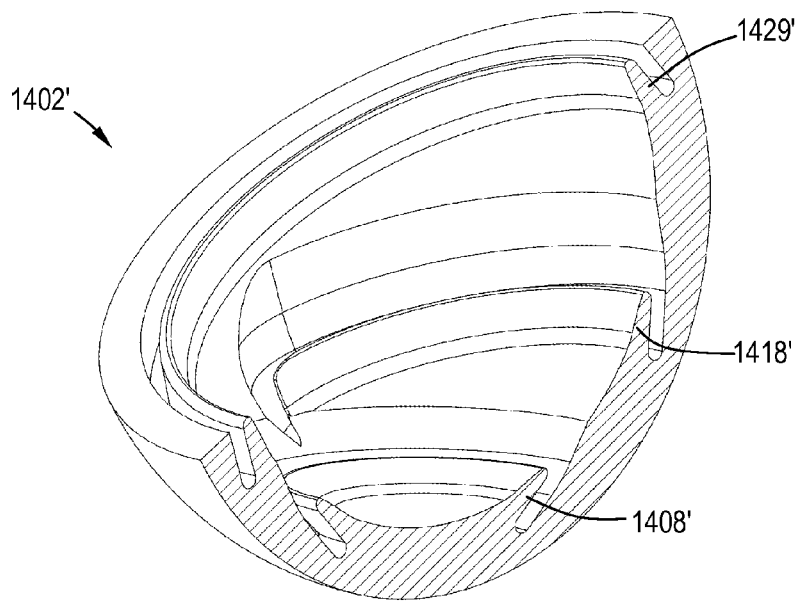
FIG. 46 is a perspective view of a prosthetic joint constructed in accordance with another aspect of the present invention.
Figure 47:
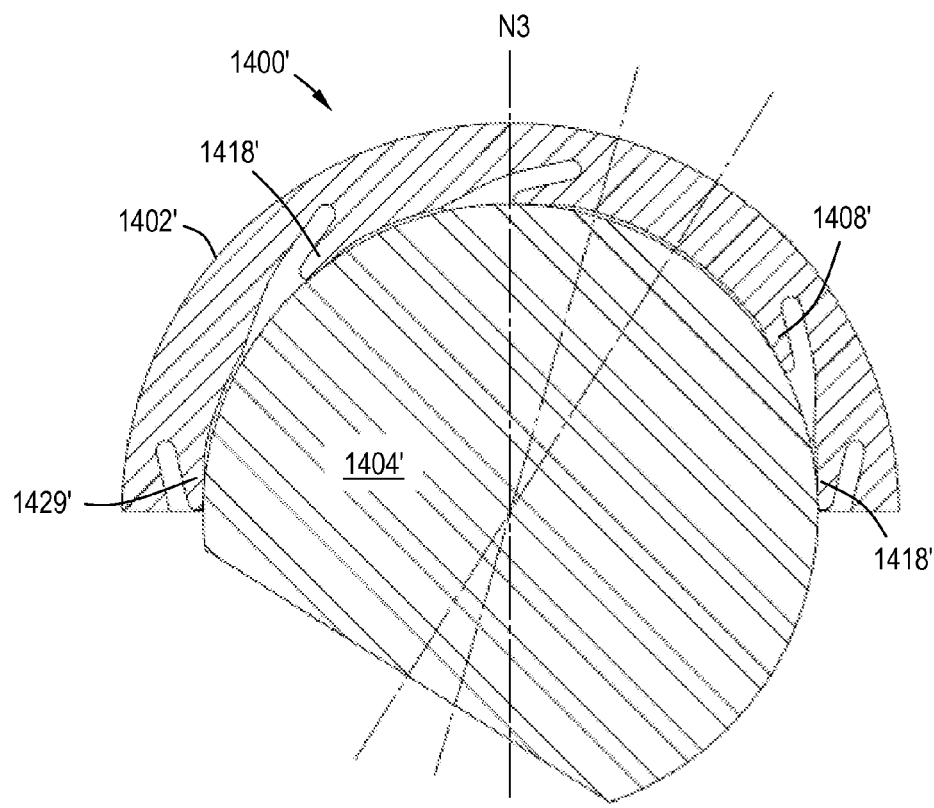
FIG. 47 is a cross-sectional view of the prosthetic joint of FIG. 46.
Figure 48:
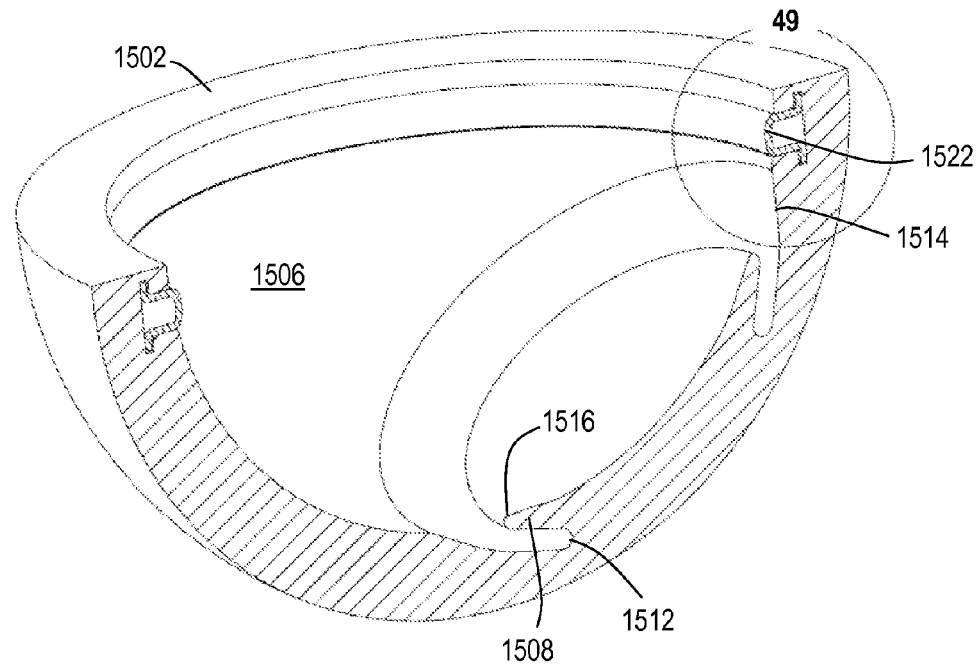
FIG. 48 is a sectional perspective view of a prosthetic joint constructed in accordance with another aspect of the present invention.
Figure 49:
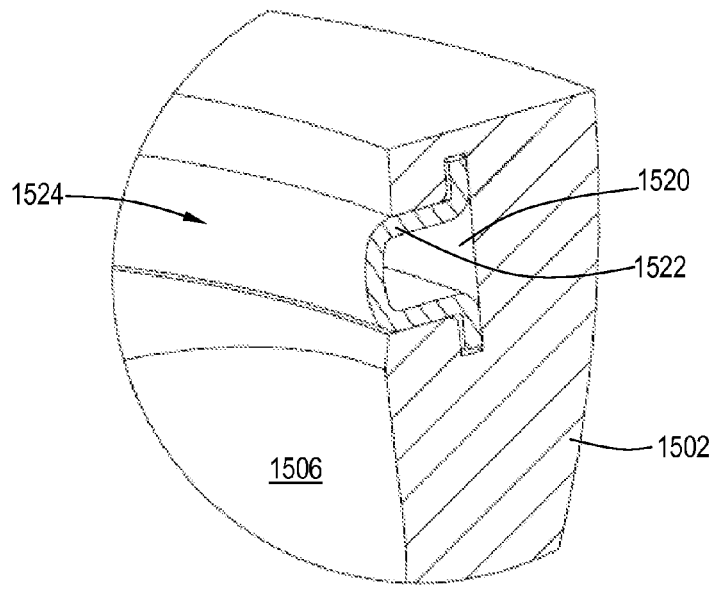
FIG. 49 is an enlarged portion of the joint of FIG. 48, showing a rim configuration thereof.

Any of the flanges may have an open perimeter. For example, FIGS. 46 and 47 illustrate a prosthetic joint 1400' similar in construction to the prosthetic joint 1400, including first and second members 1402' and 1404'. The first member 1402' includes cantilevered first, second, and third flanges 1408', 1418', and 1429'. In this example the first and third flanges 1408' and 1429' have a closed perimeter, and the second flange 1418' has an open perimeter, circumscribing less than 360 degrees. Any or all of the flanges 1408', 1418', and 1429' may be angularly offset from (i.e. asymmetric relative to) a balanced centroidal axis "N3" of the first member 1402', as described above. The construction and function of the joint 1400' is otherwise identical to the joint 1400. As described above for the flange 1429, the distal ends of any flange having an open perimeter may be feathered away from the nominal cup surface, for example either by tapering the flange's thickness or by tilting the distal ends outward relative to the remainder of the flange, so as not to contact the contact surface of opposing member FIGS. 48 and 49 illustrate a prosthetic joint member 1502, which may be used with any of the convex joint members described above.

The member 1502 is constructed from a rigid material and generally has a concave "cup" shape as described above. It may also be bone-implantable as described above. Its interior defines a nominal cup surface 1506. The interior includes a cantilevered flange 1508, defined in part by an undercut groove 1512 formed in the first member 1502. A ramped surface 1514 forms a transition from the groove 1512 to the nominal cup surface 1506. The flange 1508 includes a protruding first contact rim 1516. The first contact rim 1516 may have a straight, curved, or toroidal cross-sectional shape. The flange 1508 may include an angular offset relative to a balanced centroidal of the joint member 1502, as described above.

A peripheral groove 1520 is formed in the nominal cup surface 1506. In the example shown in FIGS. 48 and 49, it has a "T"-shaped cross-section. A contact ring 1522 is received in the groove 1520. A part of the contact ring 1522 protrudes from the nominal cup surface 1506 and defines a second contact rim 1524. In the illustrated example, the contact ring 1522 has "hat section" cross-sectional shape, with distal flanges that are received in the T-shaped groove 1520.

The contact ring 1522 is made of a rigid material and has a wear-resistant surface, as those terms are described above. It is sized and shaped to achieve controlled elastic deflection, and to be conformable in the manner of the flanges described above. Its construction is thin enough to permit bending under working loads, but not so thin as to allow material yield or fatigue cracking. Deflection of the contact ring 1522 is opposed by the elasticity of the contact ring 1522 in bending, as well as the hoop stresses therein. To achieve long life, the contact ring 1522 is sized so that stresses therein will be less than the endurance limit of the material.

Figure 50:
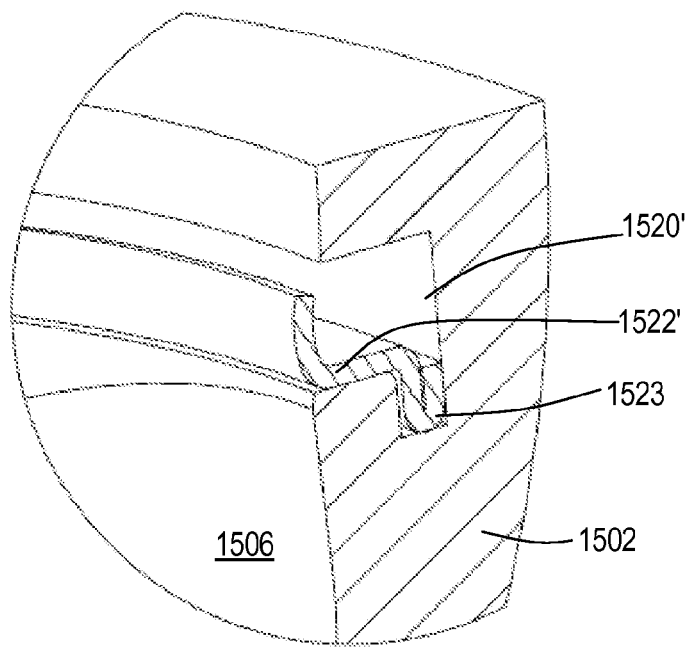
FIG. 50 is a sectional perspective view showing an alternative rim configuration for use with the joint shown in FIG. 49.
Figure 51:
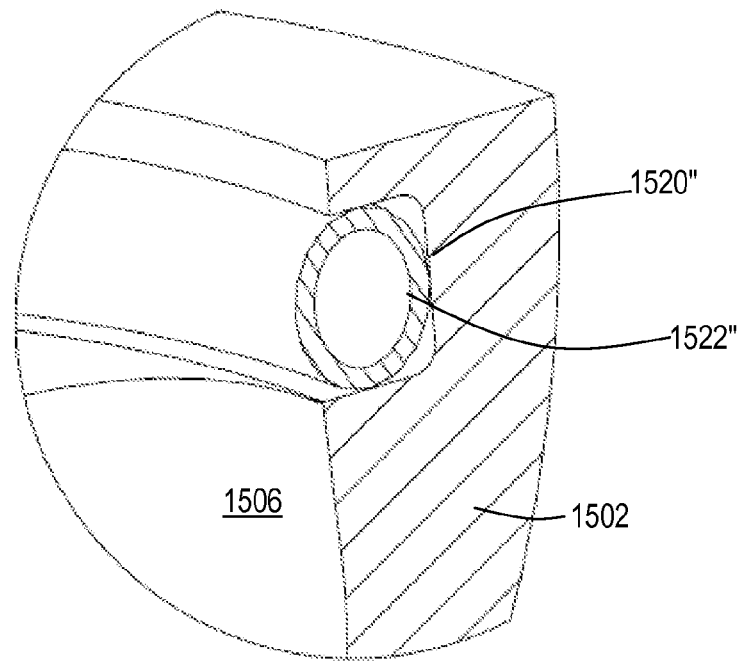
FIG. 51 is a sectional perspective view showing another alternative rim configuration for use with the joint shown in FIG. 49.

Various cross-sectional shapes may be used for the contact ring. For example, FIG. 50 illustrates a contact ring 1522' with a "Z" shape and a doubled-over retention flange 1523. FIG. 51 illustrates a contact ring 1522" with a circular cross-section. The grooves 1520' and 1520" are modified to accommodate their respective contact rings 1522' and 1522".

Nominally the first and second contact rims 1516 and 1524 define two separate "ring" or "band" contact interfaces with the contact surface of the opposed convex member (not shown). The contact rims 1516 and 1524 are conformable to an opposed contact surface when the joint is placed under load.

Figure 52:
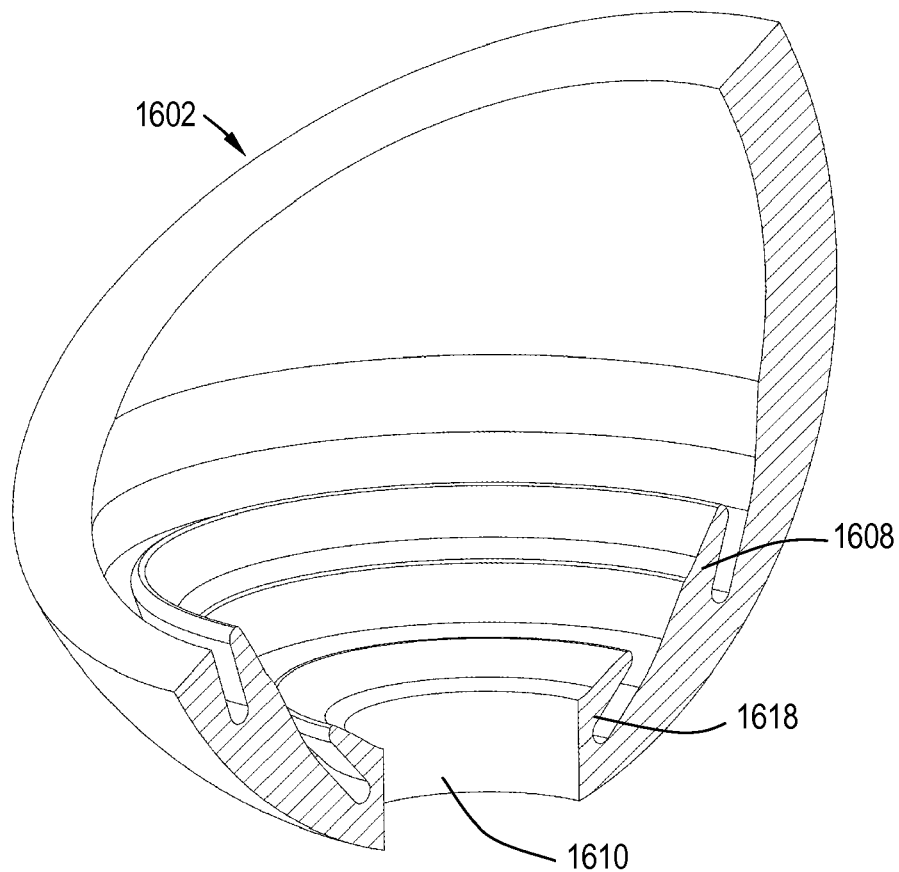
FIG. 52 is a sectional perspective view of a member of a prosthetic joint with an aperture formed therein.

Any of the joint members described above may include holes or apertures formed therein to reduce their weight, or to facilitate manufacture or installation. For example, FIG. 52 illustrates a cup joint member 1602 with first and second flanges 1608 and 1618, and an aperture 1610 formed near the apex of the cup shape.

Figure 53:
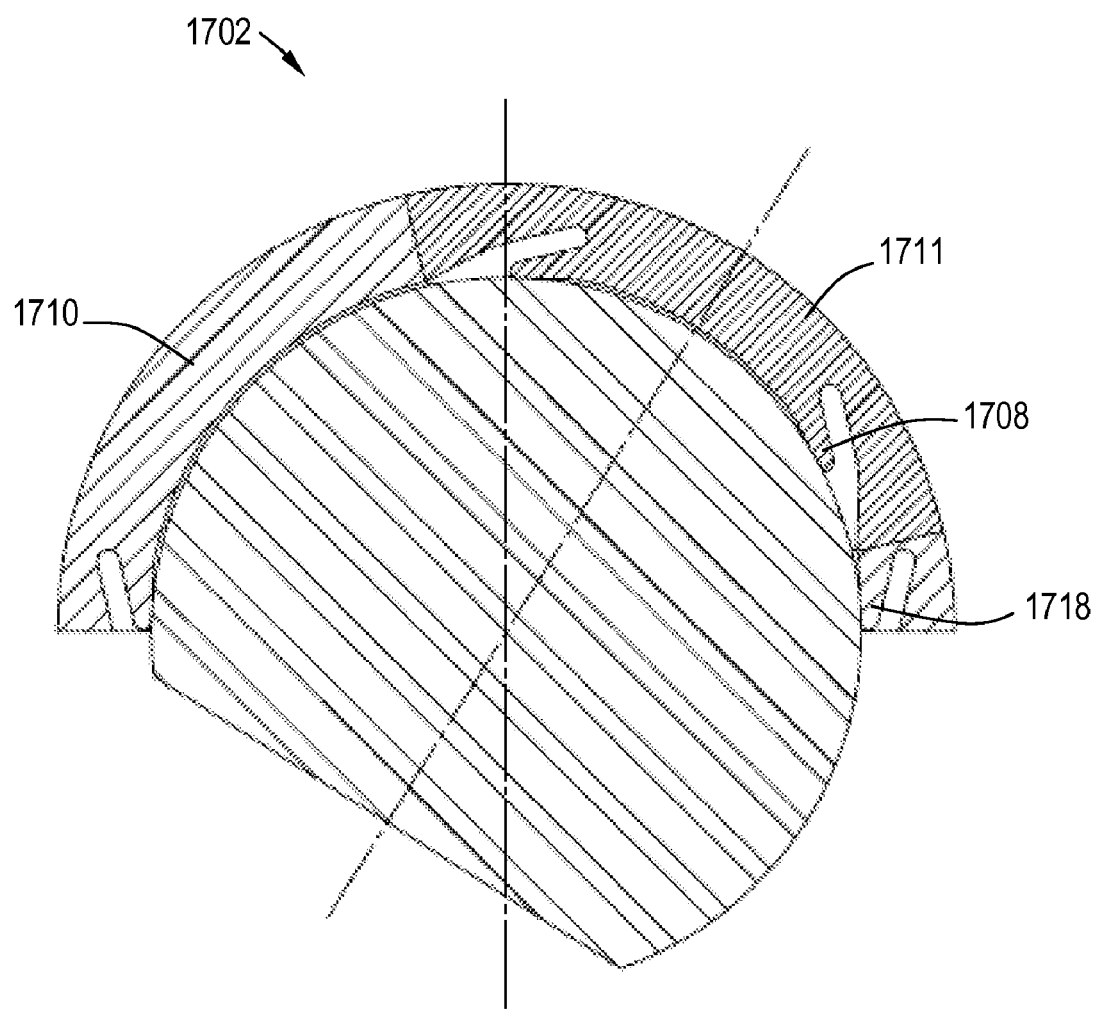
FIG. 53 is a cross-sectional view of a prosthetic joint showing a multi-piece construction.

While the joint members have been illustrated above with monolithic construction, any of the joint members may be made from one or more components built up to form the whole. For example, FIG. 53 illustrates a joint member 1702 which is a cup having a first flange 1708 and a second flange 1718 as described above. The joint member 1702 is made up from an annular first section 1710 and a cap-like second section 1711 which fit together to form the completed cup shape. The two sections 1710 and 1711 are fixed to each other, for example by a mechanical (e.g. interference) fit, an adhesive, welding or other thermal bonding method, or fasteners.

Figure 54:
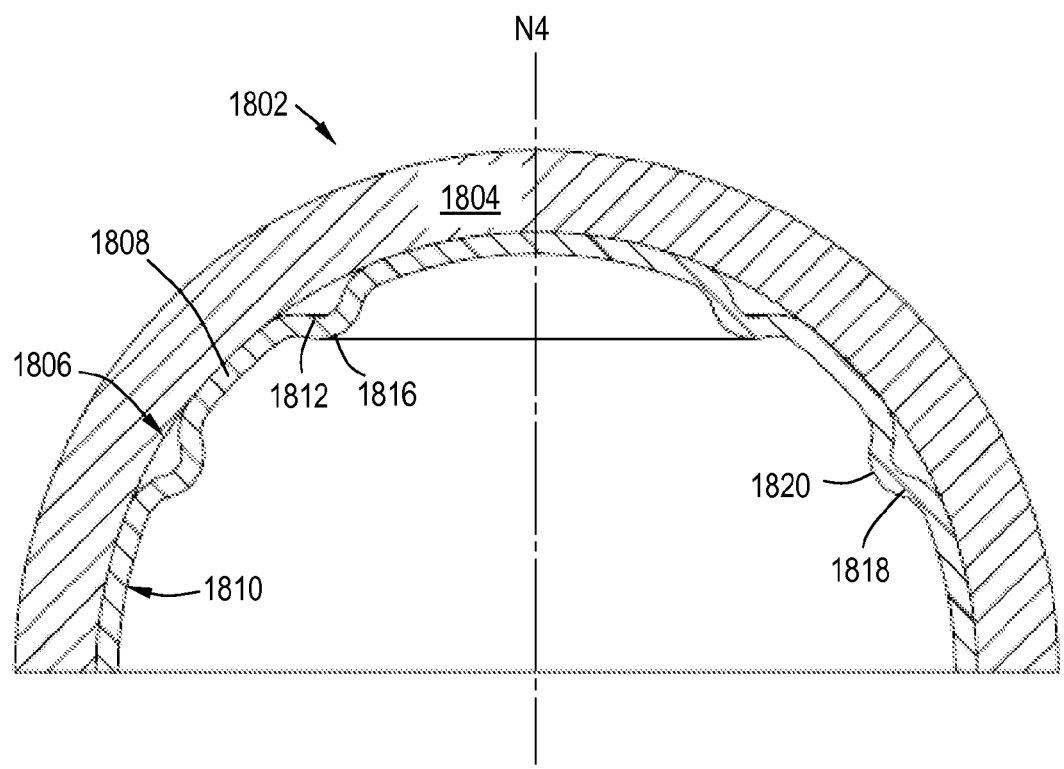
FIG. 54 is a cross-sectional view of a prosthetic joint constructed in accordance with another aspect of the present invention

FIG. 54 illustrates a prosthetic joint member 1802, which may be used with any of the convex joint members described above.

The member 1802 is constructed from a rigid material and generally has a concave "cup" shape as described above. It may also be bone-implantable as described above. It is made up from a shell 1804 with an interior surface 1806, and a liner 1808 which fits conformally against the interior surface 1806. The liner 1808 may be fixed or moveable relative to the shell 1804. An interior of the liner 1808 defines a nominal cup surface 1810. The liner 1808 includes a first peripheral ring 1812, defined as a generally "U"-shape formed in the liner 1808. The first peripheral ring 1812 includes a protruding first contact rim 1816. The first contact rim 1816 may have a straight, curved, or toroidal cross-sectional shape. The first peripheral ring 1812 may include an angular offset or asymmetric positioning relative to a balanced centroidal axis "N4" of the joint member 1802, as that concept is described above.

The liner 1808 also includes a second peripheral ring 1818, defined as a generally "U"-shape formed in the liner 1808. The second peripheral ring 1818 includes a protruding second contact rim 1820. The second contact rim 1820 may have a straight, curved, or toroidal cross-sectional shape. The second peripheral ring 1818 may include an angular offset relative to a balanced centroidal axis "N4" of the joint member 1802, as that concept is described above.

The liner 1808 is made of a rigid material and has a wear-resistant surface, as those terms are described above. The first and second peripheral rings 1812 and 1818 are sized and shaped to achieve controlled elastic deflection, and to be conformable in the manner of the flanges described above. Their construction is thin enough to permit bending under working loads, but not so thin as to allow material yield or fatigue cracking Deflection of the contact rings 1812 and 1818 are opposed by the elasticity of the rings in bending, as well as the hoop stresses therein. To achieve long life, the contact rings 1812 and 1818 are sized so that stresses therein will be less than the endurance limit of the material.

Nominally the first and second contact rims 1816 and 1820 define two separate "ring" or "band" contact interfaces with the contact surface of the opposed convex member (not shown). The contact rims 1816 and 1820 are conformable to the opposed contact surface when the joint is placed under load.

FIGS. 55-58 illustrate an alternative prosthetic joint member 1902. The illustrated prosthetic joint member 1902 is generally similar in construction and function to the prosthetic joint member 1202 described above, and is intended to be used with a complementary joint member having a convex or ball-like structure, such as the joint member 1204, in order to constitute a complete prosthetic joint.

Figure 55:
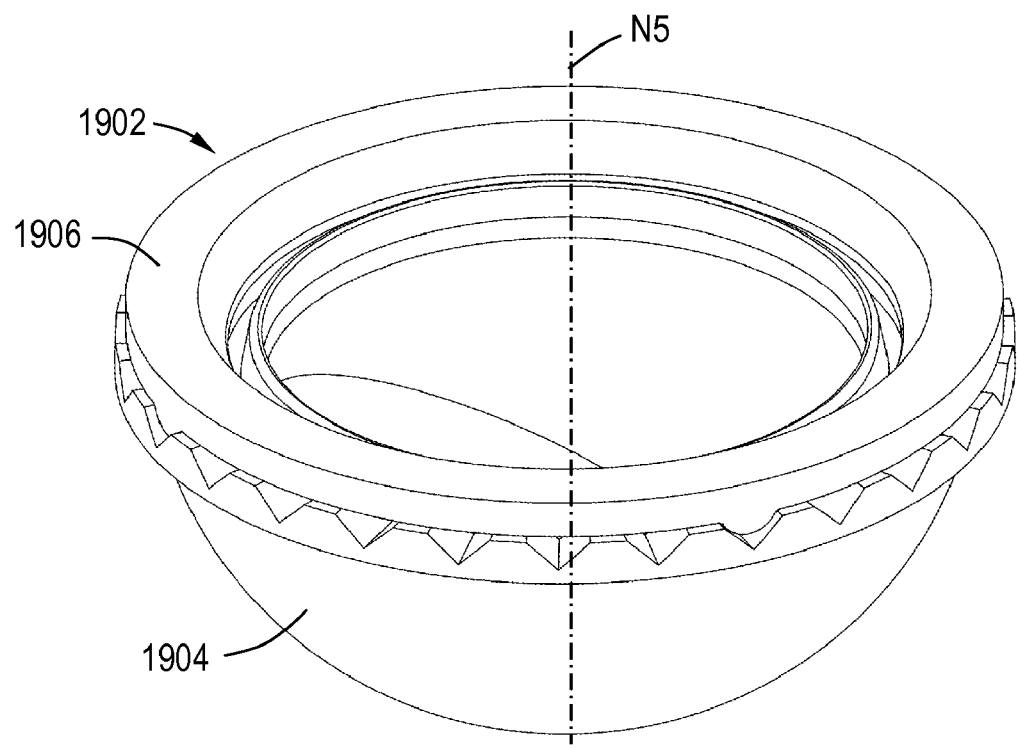
FIG. 55 is a perspective view of a prosthetic joint member.
Figure 56:
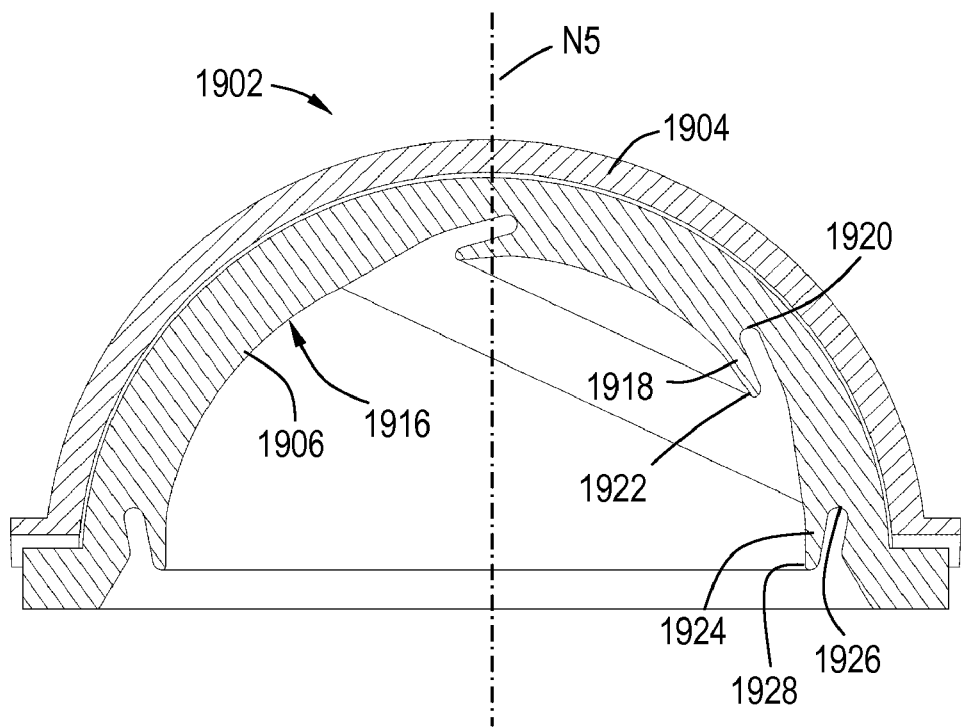
FIG. 56 is a cross-sectional view of the joint member of FIG. 55.
Figure 57:
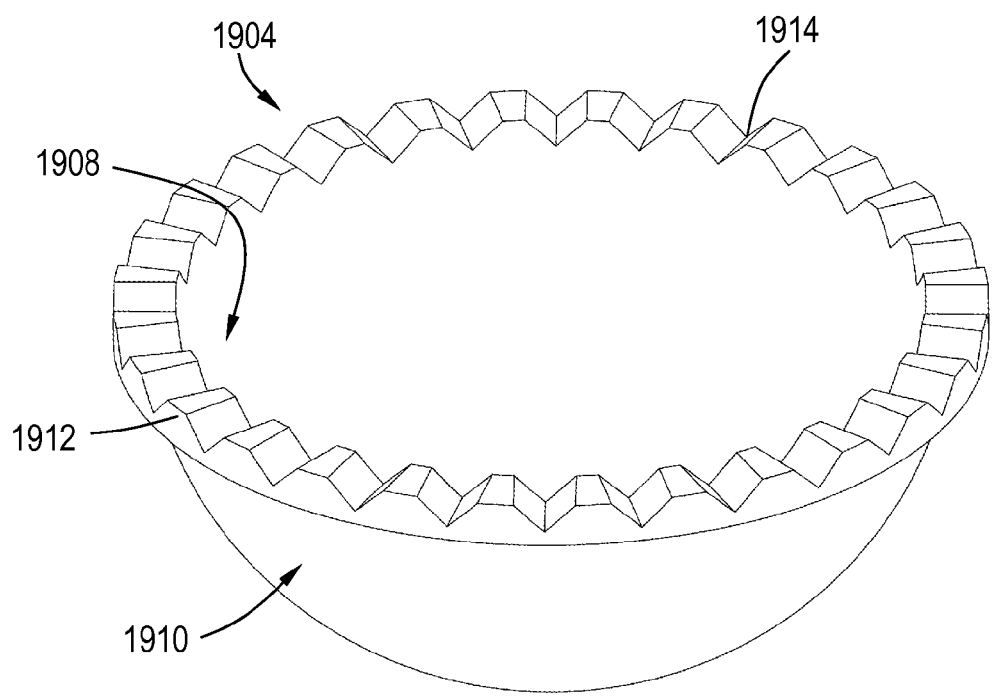
FIG. 57 is a perspective view of a cup of the joint member of FIG. 55.
Figure 58:
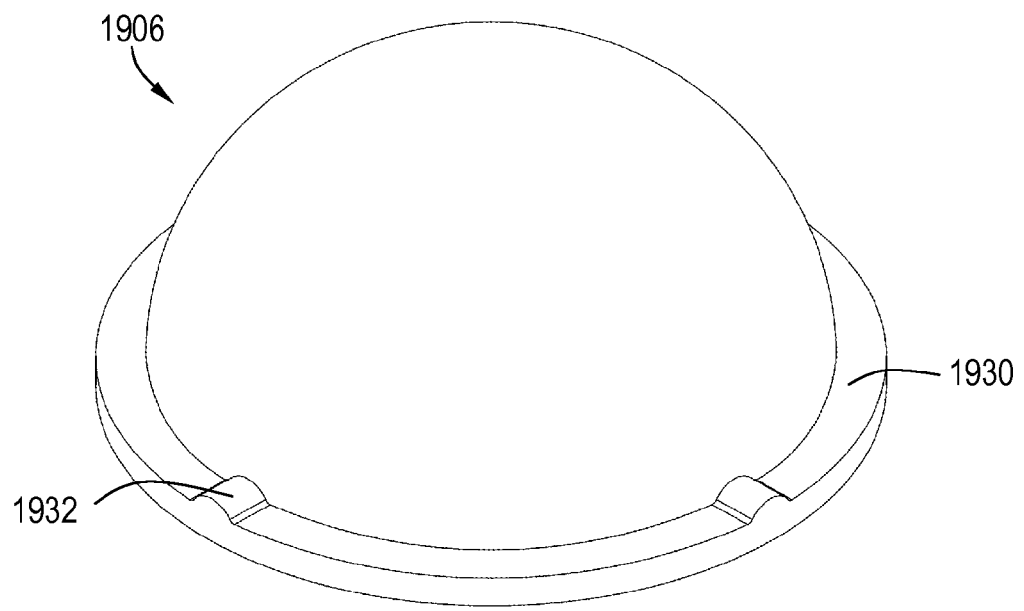
FIG. 58 is a perspective view of an insert of the joint member of FIG. 55.

For purposes of explanation and illustration the joint member 1902 will be described relative to a "balanced centroidal axis", labeled "N5" in FIG. 55, passing through it. The meaning of the term "balanced centroidal axis" is described above.

The joint member 1902 includes a cup 1904 and an insert 1906. The cup 1904 has interior and exterior surfaces 1908 and 1910, respectively. The exterior surface 1910 may be configured to be bone-implantable as described above. A peripheral rim 1912 extends around the open edge of the cup 1904. The peripheral rim 1912 includes a first indexing feature 1914 formed therein. In the particular example illustrated, the first indexing feature is a plurality of grooves or slots.

The insert 1906 is constructed from a rigid material and has a generally hemispherical shape. Its interior defines a nominal surface 1916. The interior is configured similar to that of the joint member 1202 described above and includes a cantilevered first flange 1918, defined in part by an undercut groove 1920 formed in the nominal surface 1916. The first flange 1918 has an angular offset relative to the balanced centroidal axis N5, and the first flange 1918 includes a protruding first contact rim 1922. The first contact rim 1922 may have a straight, curved, or toroidal cross-sectional shape.

The interior also includes a cantilevered second flange 1924 which is defined in part by an undercut groove 1926 formed in the nominal surface 1916. The second flange 1924 includes a protruding second contact rim 1928. The second contact rim 1928 may have a straight, curved, or toroidal cross-sectional shape. Depending on the specific application, the second flange 1924 may have an angular offset like the first flange 1918. The flanges 1918 and 1924 (and thus the contact rims 1922 and 1928) of the joint member 1902 are conformable to the contact surface of an opposed convex joint member when the joint is placed under load. The flanges 1918 and 1924 can conform to the imperfect contact surface and deflect in an irregular shape, in the manner described above for the joint 1000 described above. Contact between the contact rims and the contact surface of an opposed convex joint member permits transfer of axial and lateral loads from one member to the other while allowing pivoting motion between the two members.

A peripheral rim 1930 extends around the open edge of the insert 1906. The peripheral rim 1930 includes a second indexing feature 1932 formed therein. In the particular example illustrated, the second indexing feature 1932 is a plurality of tabs or ribs.

When the insert 1906 is assembled to the cup 1904, the first and second indexing features 1914 and 1932 engage each other and prevent relative rotation of the cup 1904 and the insert 1906 (i.e. retaining the insert 1906 in a fixed angular orientation relative to the cup 1904). The construction of the indexing features may be modified or inverted as needed to suit a particular application. For example, the peripheral rim 1930 of the insert 1906 may include slots or grooves while the peripheral rim 1912 of the cup 1904 could have tabs or ribs. The indexing features 1914 or 1932 may have a tapered or wedge shape to ensure that any clearance present between the two is taken up upon assembly of the cup 1904 to the insert 1906.

The joint member 1902 may be implanted by first placing the cup 1904 into a prepared bone surface (not shown), then selecting a specific orientation for the insert 1906. The insert 1906 is then placed into the cup 1904 in the selected orientation. The first and second indexing features 1914 and 1932 ensure that this orientation is maintained. Typically the cup 1904 would be placed using bone cement or a fastening process which must be completed in one step, or it would be difficult and/or undesirable to remove and replace the cup 1904. Because the cup 1904 and the insert 1906 are separate from each other, there is no need to maintain any particular rotational alignment of the cup 1904 about the axis N5 as it is placed, yet the insert 1906 can be clocked relative to the cup 1904 to place the flanges 1918 and 1924 in a precise orientation when finally assembled.

Figure 59:
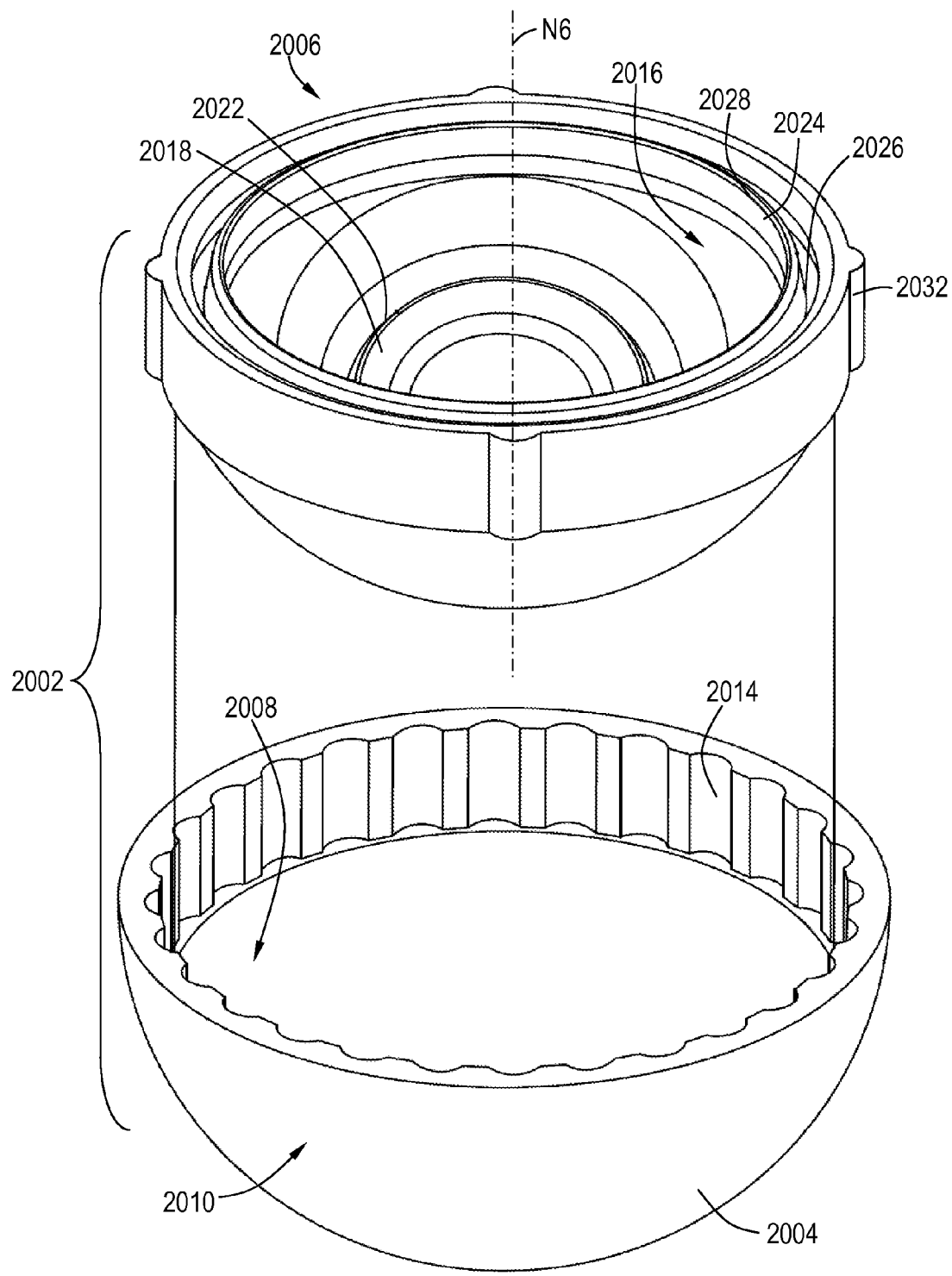
FIG. 59 is an exploded perspective view of a prosthetic joint member.

FIG. 59 illustrates an alternative prosthetic joint member 2002. It is generally similar in construction and function to the prosthetic joint member 1902 described above, and includes a cup 2004 and an insert 2006. The cup 2004 has interior and exterior surfaces 2008 and 2010, respectively, and the exterior surface 2010 may be configured to be bone-implantable as described above. A first indexing feature 2014 is formed in the interior of the cup 2004 adjacent the open edge of the cup 2004. In the particular example illustrated, the first indexing feature 2014 is a plurality of axially-aligned grooves or slots.

The insert 2006 is constructed from a rigid material and has a generally hemispherical shape. Its interior defines a nominal surface 2016. The interior is configured similar to that of the joint member 1202 described above and includes a cantilevered first flange 2018, defined in part by an undercut groove (not visible) formed in the nominal surface 2016. The first flange 2018 has an angular offset relative to a balanced centroidal axis N6 of the insert 2006, and the first flange 2018 includes a protruding first contact rim 2022. The first contact rim 2022 may have a straight, curved, or toroidal cross-sectional shape.

The interior also includes a cantilevered second flange 2024 which is defined in part by an undercut groove 2026 formed in the nominal surface 2016. The second flange 2024 includes a protruding second contact rim 2028. The second contact rim 2028 may have a straight, curved, or toroidal cross-sectional shape. Depending on the specific application, the second flange 2024 may have an angular offset like the first flange 2018. The flanges 2018 and 2024 (and thus the contact rims 2022 and 2028) of the joint member 2002 are conformable to the contact surface of an opposed convex joint member when the joint is placed under load. The flanges 2018 and 2024 can conform to the imperfect contact surface and deflect in an irregular shape, in the manner described above for the joint 1000 described above.

A second indexing feature 2032 is formed on the exterior of the insert 2006, adjacent its open edge. In the particular example illustrated, the second indexing feature 2032 is a plurality of axially-aligned ribs protruding radially outward. The ribs have a cross-sectional shape which is complementary to the grooves of the first indexing feature 2014.

The joint member 2002 may be implanted using the process described above for the joint member 1902. When the insert 2006 is assembled to the cup 2004, the first and second indexing features 2014 and 2032 engage each other and prevent relative rotation of the cup 2004 and the insert 2006. The construction of the indexing features may be modified or inverted as needed to suit a particular application. For example, the insert 2006 may include slots or grooves while the cup 2004 could have tabs or ribs. The indexing features 2014 or 2032 may have a tapered or wedge shape to ensure that any clearance present between the two is taken up upon assembly of the cup 2004 to the insert 2006.

Figure 60:
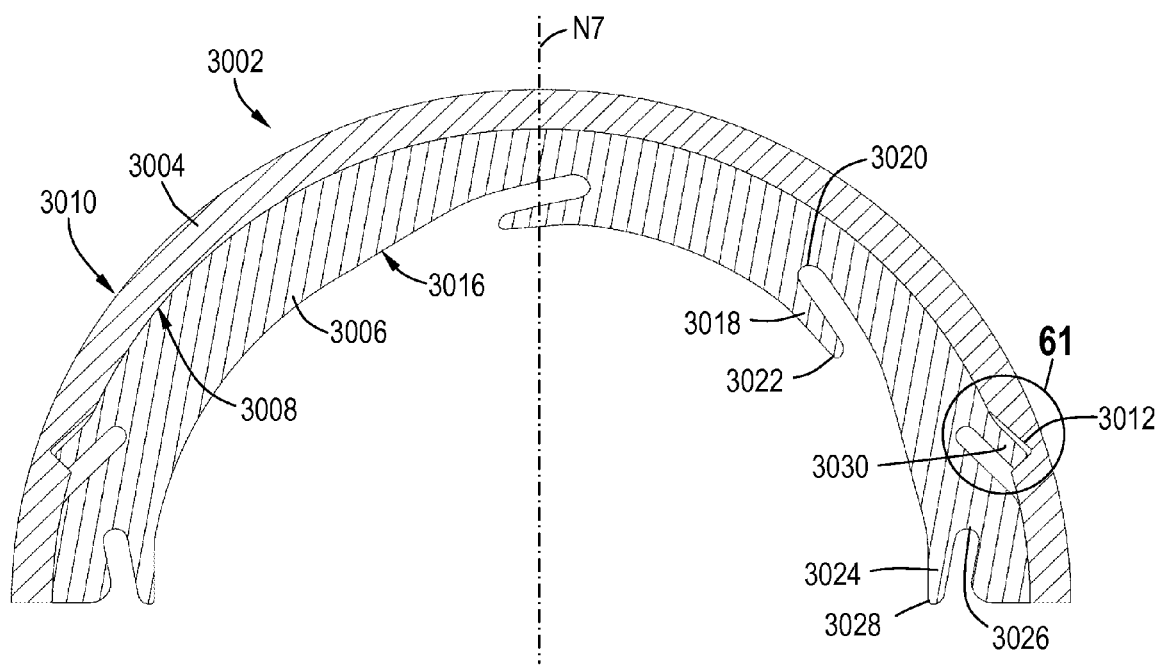
FIG. 60 is a cross-sectional view of a prosthetic joint member.
Figure 61:
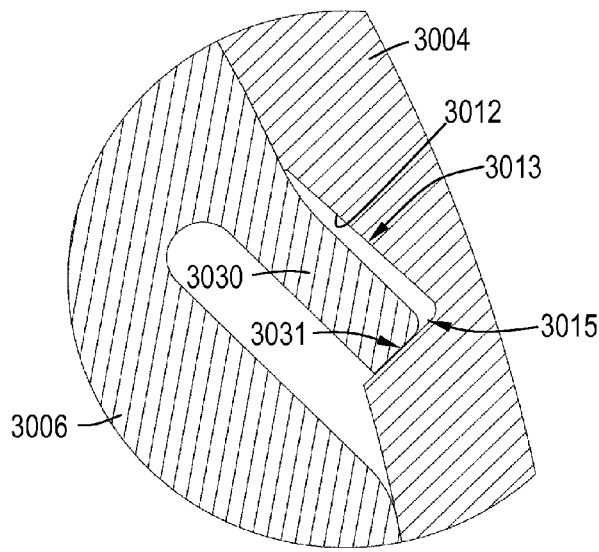
FIG. 61 is an enlarged view of a portion of the joint member of FIG. 60.
Figure 62:
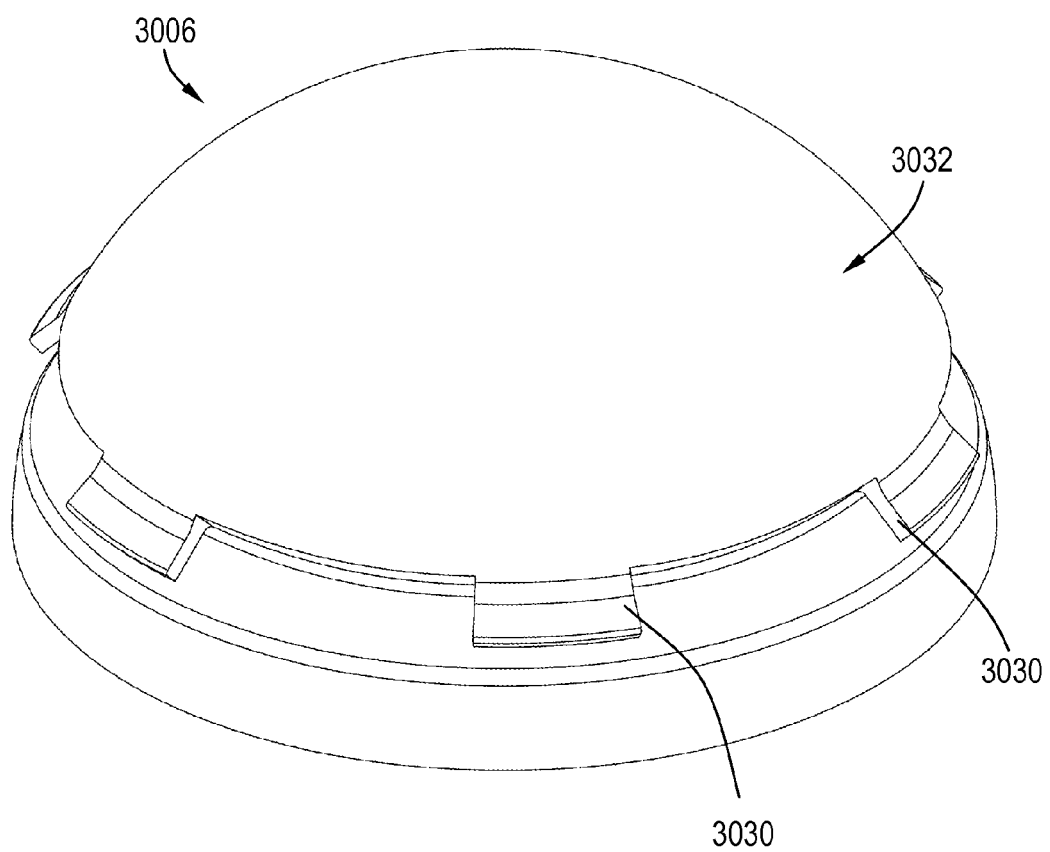
FIG. 62 is a perspective view of an insert of the joint member of FIG. 60.

FIGS. 60-62 illustrate an alternative prosthetic joint member 3002. The illustrated prosthetic joint member 3002 is generally similar in construction and function to the prosthetic joint member 1202 described above, and is intended to be used with a complementary joint member having a convex or ball-like structure, such as the joint member 1204, in order to constitute a complete prosthetic joint.

For purposes of explanation and illustration the joint member 3002 will be described relative to a "balanced centroidal axis", labeled "N7" in FIG. 60, passing through it. The meaning of the term "balanced centroidal axis" is described above.

The joint member 3002 includes a cup 3004 and an insert 3006. The cup 3004 has interior and exterior surfaces 3008 and 3010, respectively. The exterior surface 3010 may be configured to be bone-implantable as described above. The interior surface 3008 has an annular retention groove 3012 formed therein. The retention groove includes a side wall 3013 and an end wall 3015. The end wall 3015 may be angled, as shown in FIG. 61, so that its inboard end is closer to the open end of the cup 3004 than its outboard end.

The insert 3006 is constructed from a rigid material and has a generally hemispherical shape. Its interior defines a nominal surface 3016. The interior is configured similar to that of the joint member 1202 described above and includes a cantilevered first flange 3018, defined in part by an undercut groove 3020 formed in the nominal surface 3016. The first flange 3018 has an angular offset relative to the balanced centroidal axis N7, and the first flange 3018 includes a protruding first contact rim 3022. The first contact rim 3022 may have a straight, curved, or toroidal cross-sectional shape.

The interior also includes a cantilevered second flange 3024 which is defined in part by an undercut groove 3026 formed in the nominal surface 3016. The second flange 3024 includes a protruding second contact rim 3028. The second contact rim 3028 may have a straight, curved, or toroidal cross-sectional shape. Depending on the specific application, the second flange 3024 may have an angular offset like the first flange 3018. The flanges 3018 and 3024 (and thus the contact rims 3022 and 3028) of the joint member 3002 are conformable to the contact surface of an opposed convex joint member when the joint is placed under load. The flanges 3018 and 3024 can conform to the imperfect contact surface and deflect in an irregular shape, in the manner described above for the joint 1000 described above.

As best seen in FIG. 62, a plurality of retention tabs 3030 extend outward from an outer surface 3032 of the insert 3006. In the illustrated example the retention tabs 3030 are integrally formed with the insert 3006, but they could be formed separately and then attached to the insert 3006. The retention tabs 3030 are cantilevered spring members and are sized and shaped to fit into the retention groove 3012 of the cup 3004. As shown the retention tabs 3030 are arrayed evenly around the periphery of the insert 3006. The specific configuration of the retention tabs 3030 may be altered to suit a particular application, for example the angular width, length, thickness, and number of tabs may be altered as needed.

Referring to FIGS. 60 and 61, when the insert 3006 is assembled to the cup 3004, the retention tabs 3030 will be deflected inward. When the insert is fully seated the retention tabs 3030 will spring outward into the retention groove 3012, holding the insert 3006 securely engaged with the cup 3004. The retention tabs 3030 may be configured to have a "self-locking" function, such that their engagement with the retention groove 3012 is assured even if the insert 3006 is displaced further into the cup 3004. For example, as shown in FIG. 61, each retention tab 3030 includes an end face 3031 which is roughly parallel to the angled end wall 3015 of the retention groove 3012. Initial contact with the end wall 3015 limits the outward motion of the retention tabs 3030 before they contact the side wall 3013. It can be seen that if the insert 3006 is advanced further into the cup 3006 the retention tabs 3030 will spring outward an additional amount allowing the end face 3031 to advance further along the end wall 3015, but always maintaining contact.

Figure 63:
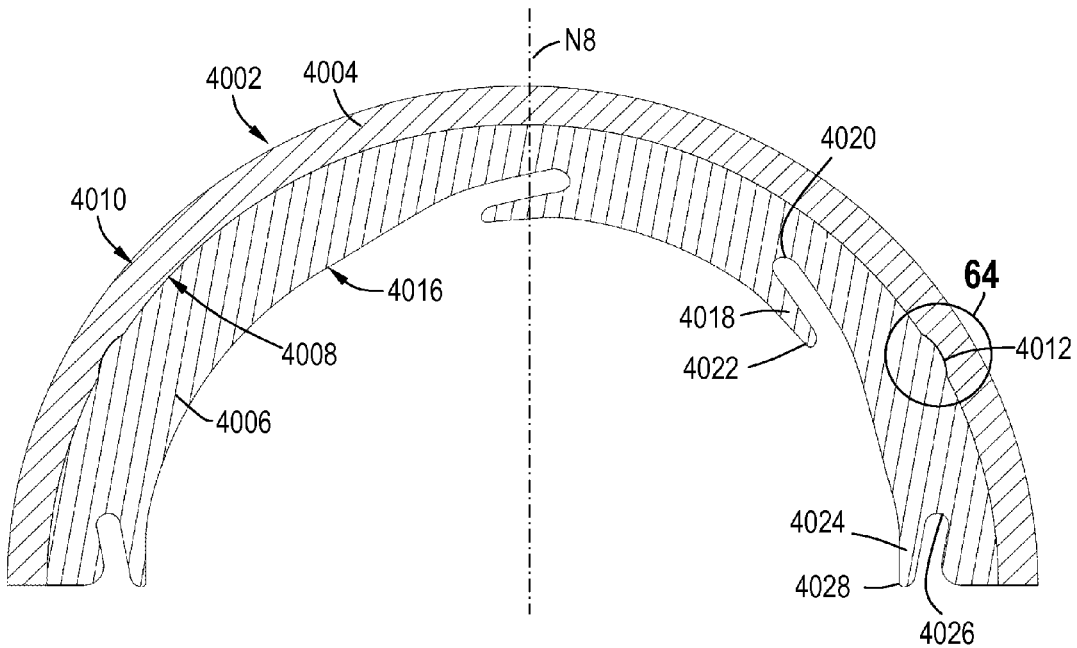
FIG. 63 is a cross-sectional view of a prosthetic joint member.
Figure 64:
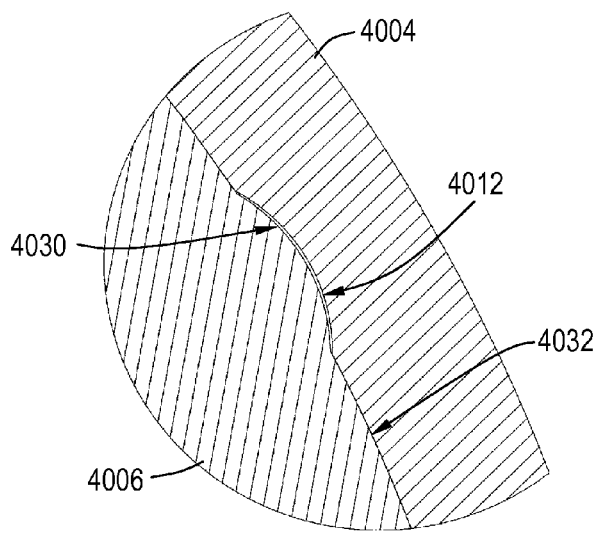
FIG. 64 is an enlarged view of a portion of the joint member of FIG. 63.

FIGS. 63 and 64 illustrate an alternative prosthetic joint member 4002. The illustrated prosthetic joint member 4002 is generally similar in construction and function to the prosthetic joint member 3002 described above, and is intended to be used with a complementary joint member having a convex or ball-like structure, such as the joint member 1204, in order to constitute a complete prosthetic joint.

For purposes of explanation and illustration the joint member 4002 will be described relative to a "balanced centroidal axis", labeled "N8" in FIG. 63, passing through it. The meaning of the term "balanced centroidal axis" is described above.

The joint member 4002 includes a cup 4004 and an insert 4006. The cup 4004 has interior and exterior surfaces 4008 and 4010, respectively. The exterior surface 4010 may be configured to be bone-implantable as described above. The interior surface 4008 has a first detent element 4012 formed therein, in this particular example a concave groove. The first detent element 4012 could be a continuous annular groove, or it could comprise an annular array of individual recesses.

The insert 4006 is constructed from a rigid material and has a generally hemispherical shape. Its interior defines a nominal surface 4016. The interior is configured similar to that of the joint member 3002 described above and includes a cantilevered first flange 4018, defined in part by an undercut groove 4020 formed in the nominal surface 4016. The first flange 4018 has an angular offset relative to the balanced centroidal axis N8, and the first flange 4018 includes a protruding first contact rim 4022. The first contact rim 4022 may have a straight, curved, or toroidal cross-sectional shape.

The interior also includes a cantilevered second flange 4024 which is defined in part by an undercut groove 4026 formed in the nominal surface 4016. The second flange 4024 includes a protruding second contact rim 4028. The second contact rim 4028 may have a straight, curved, or toroidal cross-sectional shape. Depending on the specific application, the second flange 4024 may have an angular offset like the first flange 4018. The flanges 4018 and 4024 (and thus the contact rims 4022 and 4028) of the joint member 4002 are conformable to the contact surface of an opposed convex joint member when the joint is placed under load. The flanges 4018 and 4024 can conform to the imperfect contact surface and deflect in an irregular shape, in the manner described above for the joint 1000 described above.

A second detent feature 4030, in this particular example a convex rib, is formed on an outer surface 4032 of the insert 3006. The second detent feature 4030 could be a continuous protruding annular rib, or it could comprise an annular array of individual, dome-like protrusions. The second detent element 4030 is sized and shaped to fit into the first detent elements 4012 of the cup 4004. Cooperatively, the detent elements 4012 and 4030 function as a "detent" in the sense that, when the detent elements 4012 and 4030 are engaged with each other, they prevent relative movement of the cup 4004 and the insert 4006. The specific configuration of the detent elements 4012 and 4030 may be altered to suit a particular application, for example the shape, size, and number of the detent elements may be altered as needed. Furthermore the concave/convex relationship between the detent elements 4012 and 4030 may be reversed.

When the insert 4006 is assembled to the cup 4004, the second detent elements 4030 will engage the first detent element 4012, holding the insert 4006 securely engaged with the cup 4004. In cases where the first and second detent elements 4012 and 4030 each comprise a plurality of discrete members, the cooperating detent elements would also serve to positively index the relative angular orientation of the cup 4004 and the insert 4006, in the manner described above.

Figure 65:
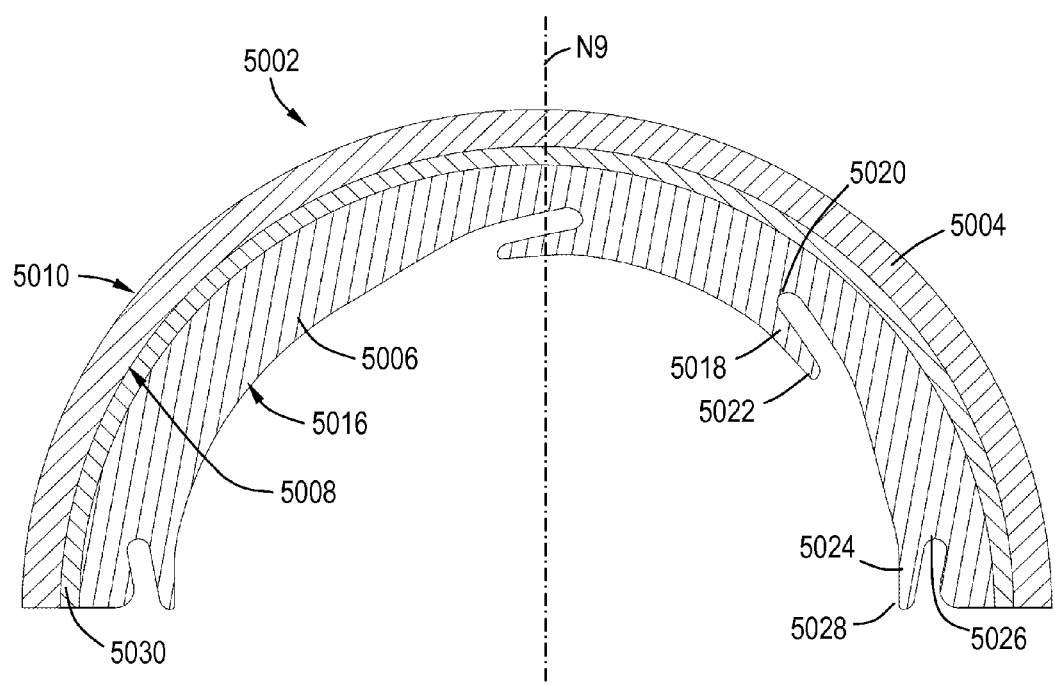
FIG. 65 is a cross-sectional view of a prosthetic joint member.

FIG. 65 illustrates an alternative prosthetic joint member 5002. The illustrated prosthetic joint member 5002 is generally similar in construction and function to the prosthetic joint member 1202 described above, and is intended to be used with a complementary joint member having a convex or ball-like structure, such as the joint member 1204, in order to constitute a complete prosthetic joint.

For purposes of explanation and illustration the joint member 5002 will be described relative to a "balanced centroidal axis", labeled "N9" in FIG. 65, passing through it. The meaning of the term "balanced centroidal axis" is described above.

The joint member 5002 includes a cup 5004 and an insert 5006. The cup 5004 has interior and exterior surfaces 5008 and 5010, respectively. The exterior surface 5010 may be configured to be bone-implantable as described above.

The insert 5006 is constructed from a rigid material and has a generally hemispherical shape. Its interior defines a nominal surface 5016. The interior is configured similar to that of the joint member 1202 described above and includes a cantilevered first flange 5018, defined in part by an undercut groove 5020 formed in the nominal surface 5016. The first flange 5018 has an angular offset relative to the balanced centroidal axis N9, and the first flange 5018 includes a protruding first contact rim 5022. The first contact rim 5022 may have a straight, curved, or toroidal cross-sectional shape.

The interior also includes a cantilevered second flange 5024 which is defined in part by an undercut groove 5026 formed in the nominal surface 5016. The second flange 5024 includes a protruding second contact rim 5028. The second contact rim 5028 may have a straight, curved, or toroidal cross-sectional shape. Depending on the specific application, the second flange 5024 may have an angular offset like the first flange 5018. The flanges 5018 and 5024 (and thus the contact rims 5022 and 5028) of the joint member 5002 are conformable to the contact surface of an opposed convex joint member when the joint is placed under load. The flanges 5018 and 5024 can conform to the imperfect contact surface and deflect in an irregular shape, in the manner described above for the joint 1000 described above.

A compliant spacer 5030 is disposed between the cup 5004 and the insert 5006. The spacer 5030 is constructed from a material that is sufficiently "soft" to deform compliantly when the insert 5006 is installed in the cup 5004. Nonlimiting examples of suitable materials for the spacer 5030 include polymers and elastomeric materials. The spacer 5030 is fixed relative to the insert 5006. One function of the spacer 5030 is to compliantly support the insert 5006 inside the cup 5004. It is possible that the cup 5004 can be implanted so that its interior surface 5008 is distorted from a nominal shape. Rigid installation of the insert 5006 directly against the cup 5004 could in turn cause excessive distortion of the insert 5006. In such situations the compliant nature of the spacer 5006 allows the insert 5006 to remain in a nominal shape.

It is also possible for the spacer 5030 to provide overload protection to the joint member 5002. Specifically, when the joint member 5002 is subjected to a load beyond the normal working range of the flanges 5018 and 5024, the convex joint member will tend to "bottom out" against the insert 5006, resulting in metal-to-metal contact with high local contact stresses. In such situations, the compliant nature of the spacer 5030 allows it to compress under loading and permit the insert 5006 to move towards the cup 5004, relieving the high contact stresses. The spacer 5030 will return to its original shape and dimensions when the loading is removed.

Figure 66:
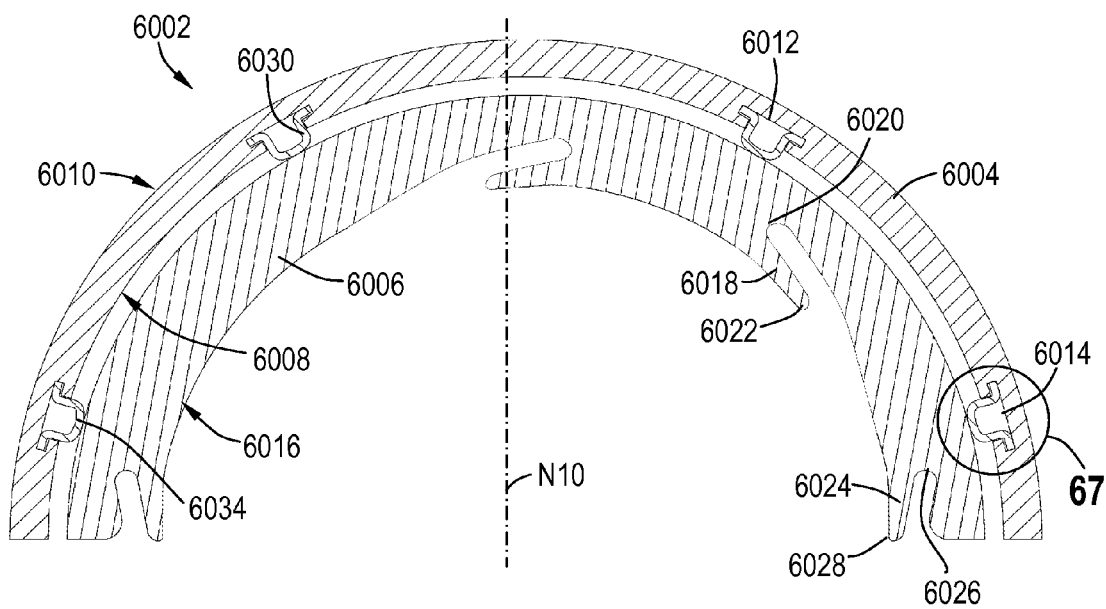
FIG. 66 is a cross-sectional view of a prosthetic joint member.
Figure 67:
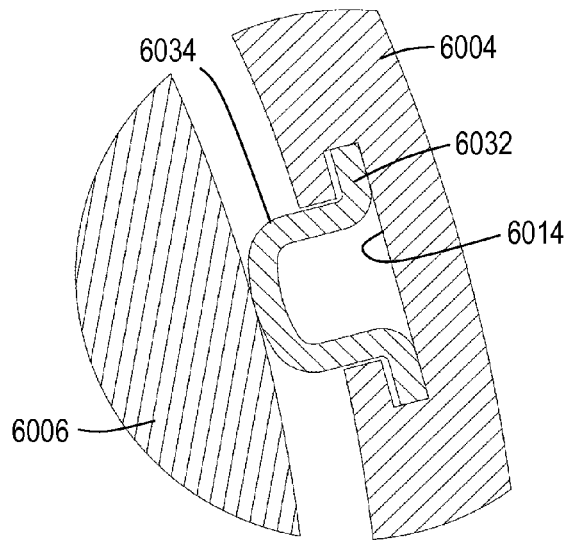
FIG. 67 is an enlarged view of a portion of the joint member of FIG. 66.

FIGS. 66 and 67 illustrate another alternative prosthetic joint member 6002. The illustrated prosthetic joint member 6002 is generally similar in construction and function to the prosthetic joint member 1202 described above, and is intended to be used with a complementary joint member having a convex or ball-like structure, such as the joint member 1204, in order to constitute a complete prosthetic joint.

For purposes of explanation and illustration the joint member 6002 will be described relative to a "balanced centroidal axis", labeled "N10" in FIG. 66, passing through it. The meaning of the term "balanced centroidal axis" is described above.

The joint member 6002 includes a cup 6004 and an insert 6006. The cup 6004 has interior and exterior surfaces 6008 and 6010, respectively. The exterior surface 6010 may be configured to be bone-implantable as described above. First and second annular spacer grooves 6012 and 6014 are formed in the interior surface 6008. Each spacer groove 6012 and 6014 has a generally "T"-shaped cross-sectional shape.

The insert 6006 is constructed from a rigid material and has a generally hemispherical shape. Its interior defines a nominal surface 6016. The interior is configured similar to that of the joint member 1202 described above and includes a cantilevered first flange 6018, defined in part by an undercut groove 6020 formed in the nominal surface 6016. The first flange 6018 has an angular offset relative to the balanced centroidal axis N10, and the first flange 6018 includes a protruding first contact rim 6022. The first contact rim 6022 may have a straight, curved, or toroidal cross-sectional shape.

The interior also includes a cantilevered second flange 6024 which is defined in part by an undercut groove 6026 formed in the nominal surface 6016. The second flange 6024 includes a protruding second contact rim 6028. The second contact rim 6028 may have a straight, curved, or toroidal cross-sectional shape. Depending on the specific application, the second flange 6024 may have an angular offset like the first flange 6018. The flanges 6018 and 6024 (and thus the contact rims 6022 and 6028) of the joint member 6002 are conformable to the contact surface of an opposed convex joint member when the joint is placed under load. The flanges 6018 and 6024 can conform to the imperfect contact surface and deflect in an irregular shape, in the manner described above for the joint 1000 described above.

A resilient first spacer ring 6030 is disposed between the cup 6004 and the insert 6006. The first spacer ring 6030 has a cross-sectional shape generally referred to as a "hat" section with laterally-extending flanges 6032. The flanges 6032 are received in the T-shaped first spacer groove 6012. A second spacer ring 6034 of identical configuration to the first spacer ring 6030 is received in the second spacer groove 6014. The first and second spacer rings 6030 and 6034 are configured so as to resiliently (or elastically) deflect under loading and permit the insert 6006 to move towards the cup 6004, then return to its original shape and dimensions when the loading is removed. Nonlimiting examples of suitable materials for the spacer rings 6030 include metal alloys, polymers and elastomeric materials.

Figure 68:
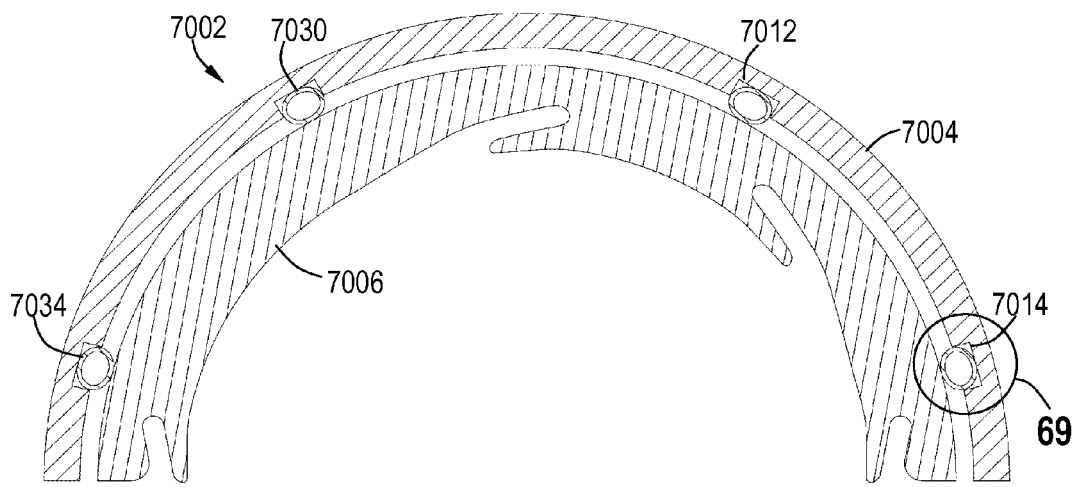
FIG. 68 is a cross-sectional view of a prosthetic joint member.
Figure 69:
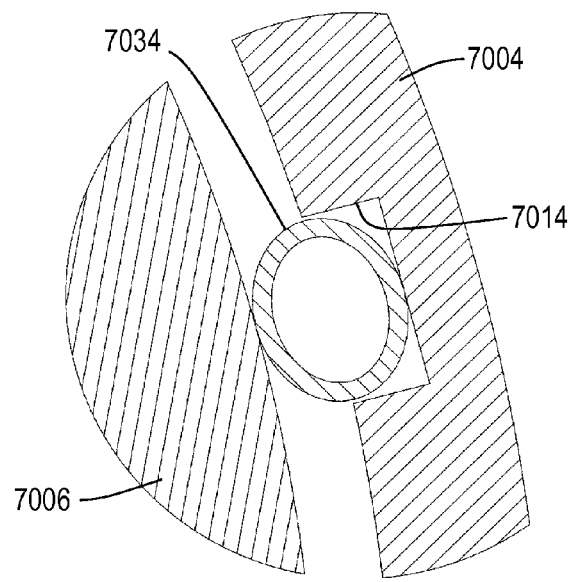
FIG. 69 is an enlarged view of a portion of the joint member of FIG. 68.

FIGS. 68 and 69 depict a joint member 7002 having a cup 7004 and insert 7006. The insert 7006 is of identical construction to the insert 6006 described above. The cup 7004 is identical in construction to the cup 6004 described above except for the configuration of the first and second spacer grooves 7012 and 7014, both of which have plain rectangular cross-sectional shapes.

A resilient first spacer ring 7030 is disposed between the cup 7004 and the insert 7006. The first spacer ring 7030 has a closed-loop cross-sectional shape (e.g. circular, oval, or elliptical). A second spacer ring 7034 of identical configuration to the first spacer ring 7030 is received in the second spacer groove 7014. The first and second spacer rings 7030 and 7034 are configured so as to resiliently (or elastically) deflect under loading and permit the insert 7006 to move towards the cup 7004, then return to its original shape and dimensions when the loading is removed. Nonlimiting examples of suitable materials for the spacer rings 7030 and 7034 include metal alloys, polymers and elastomeric materials.

Figure 70:
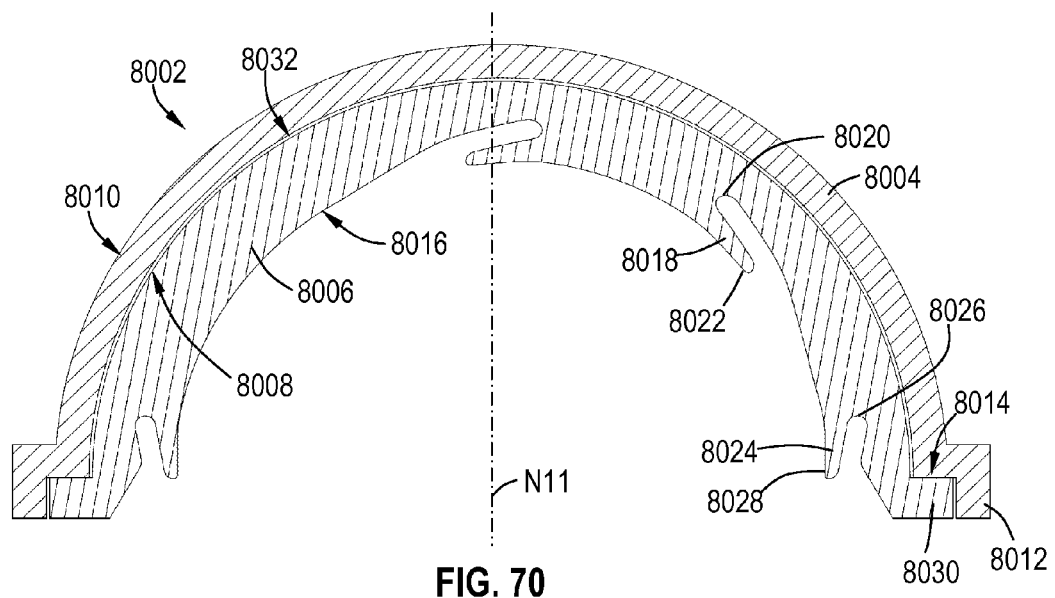
FIG. 70 is a cross-sectional view of a prosthetic joint member.

FIG. 70 illustrates another alternative prosthetic joint member 8002. The illustrated prosthetic joint member 8002 is generally similar in construction and function to the prosthetic joint member 1202 described above, and is intended to be used with a complementary joint member having a convex or ball-like structure, such as the joint member 1204, in order to constitute a complete prosthetic joint.

For purposes of explanation and illustration the joint member 8002 will be described relative to a "balanced centroidal axis", labeled "N11" in FIG. 70, passing through it. The meaning of the term "balanced centroidal axis" is described above.

The joint member 8002 includes a cup 8004 and an insert 8006. The cup 8004 has interior and exterior surfaces 8008 and 8010, respectively. The exterior surface 8010 may be configured to be bone-implantable as described above. A peripheral rim 8012 extends around the open edge of the cup 8004. The rim 8012 is shaped so as to define an annular, L-shaped interior corner or "step" 8014.

The insert 8006 is constructed from a rigid material and has a generally hemispherical shape. Its interior defines a nominal surface 8016. The interior is configured similar to that of the joint member 1202 described above and includes a cantilevered first flange 8018, defined in part by an undercut groove 8020 formed in the nominal surface 8016. The first flange 8018 has an angular offset relative to the balanced centroidal axis N11, and the first flange 8018 includes a protruding first contact rim 8022. The first contact rim 8022 may have a straight, curved, or toroidal cross-sectional shape.

The interior also includes a cantilevered second flange 8024 which is defined in part by an undercut groove 8026 formed in the nominal surface 8016. The second flange 8024 includes a protruding second contact rim 8028. The second contact rim 8028 may have a straight, curved, or toroidal cross-sectional shape. Depending on the specific application, the second flange 8024 may have an angular offset like the first flange 8018. The flanges 8018 and 8024 (and thus the contact rims 8022 and 8028) of the joint member 8002 are conformable to the contact surface of an opposed convex joint member when the joint is placed under load. The flanges 8018 and 8024 can conform to the imperfect contact surface and deflect in an irregular shape, in the manner described above for the joint 1000 described above.

An annular lip 8030 extends radially outward from the open edge of the insert 8006. The lip 8030 is received in the step 8014 of the cup 8004. The dimensions of the cup 8004 and the insert 8006, and the position of the step 8014 and the lip 8030 are selected such that, when the lip 8030 and the step 8014 are in contact, a definite clearance 8032 is present between the cup 8004 and the insert 8006.

This clearance allows the insert 8006 to resiliently deflect under loading and move towards the cup 8004, then return to its original shape and dimensions when the loading is removed. If desired, the clearance 8032 could be filled with a polymer or elastomeric material to tailor the deflection properties of the joint member 8002 and provide damping between the insert 8006 and the cup 8004.

Figure 71:
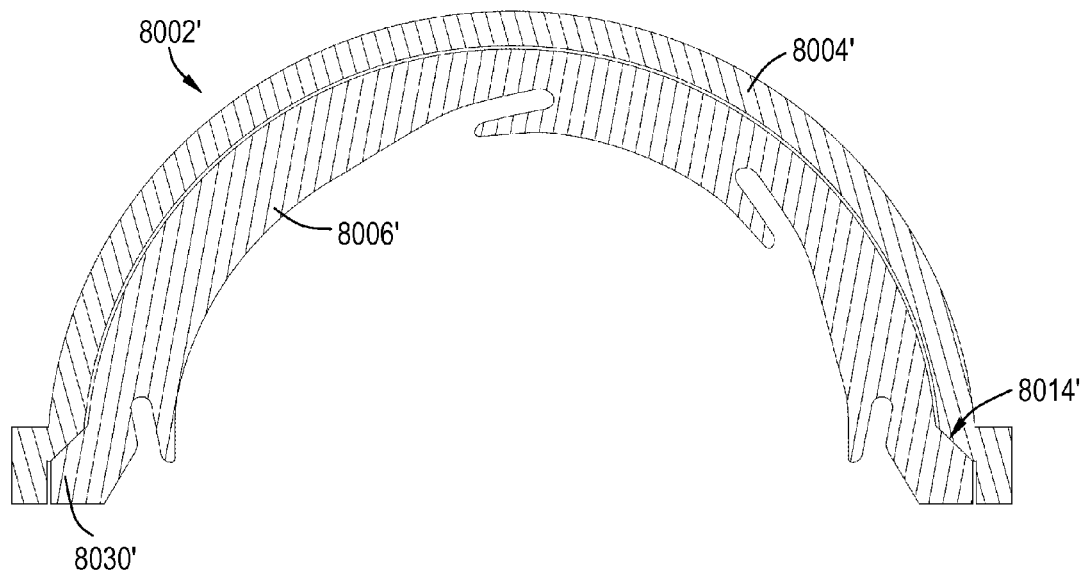
FIG. 71 is a cross-sectional view of a prosthetic joint member.

FIG. 71 depicts a joint member 8002' having a cup 8004' and insert 8006'. These two components are of identical construction to the cup 8004 and insert 8006, respectively, except for the configuration of the contact interface therebetween. Specifically, the step 8014' of the cup 8004' is angled rather than L-shaped in cross section. The lip 8030' of the insert 8006' has a surface with an angle matching the step 8014'.

Figure 72:
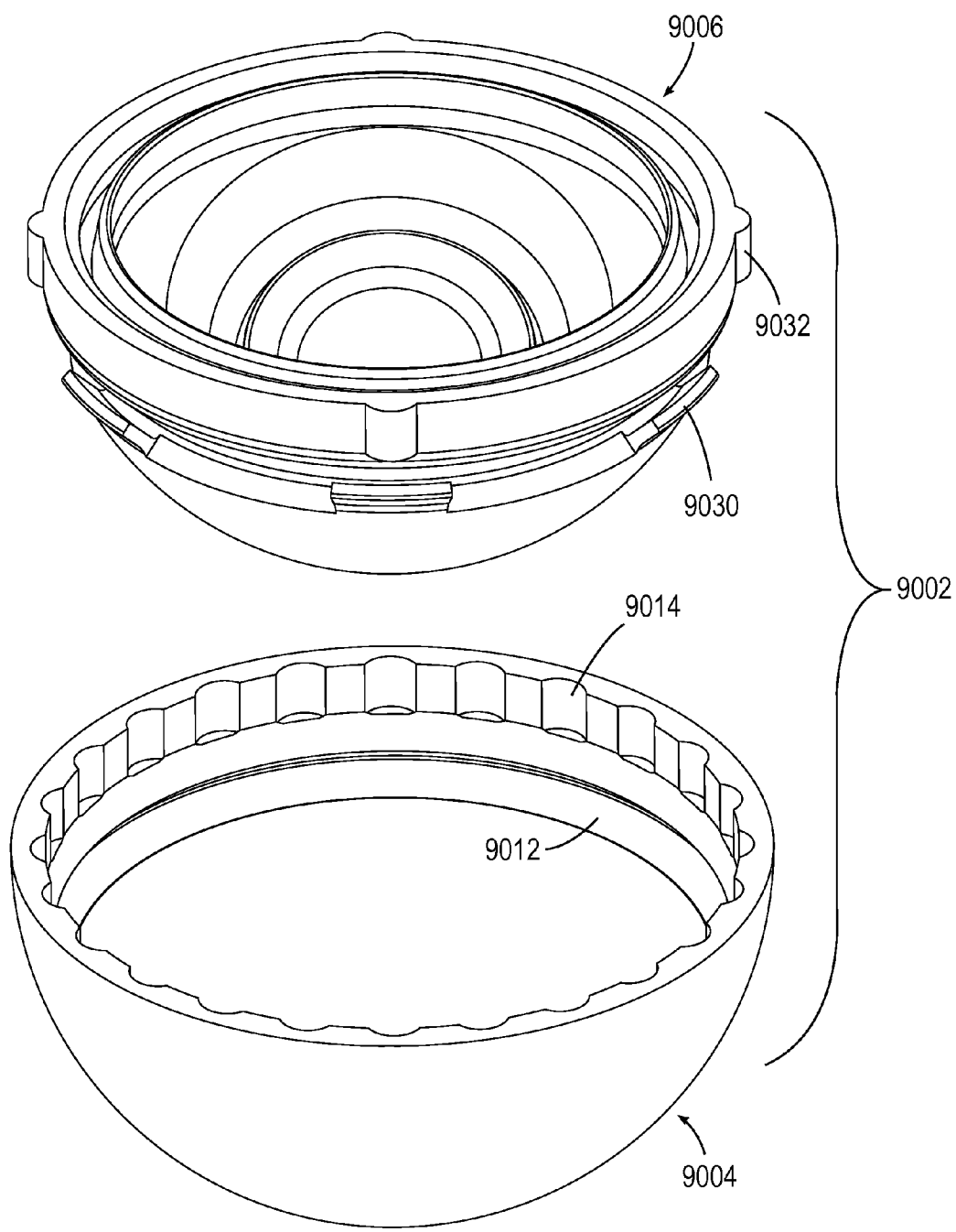
FIG. 72 is an exploded perspective view of a prosthetic joint.
Figure 73:
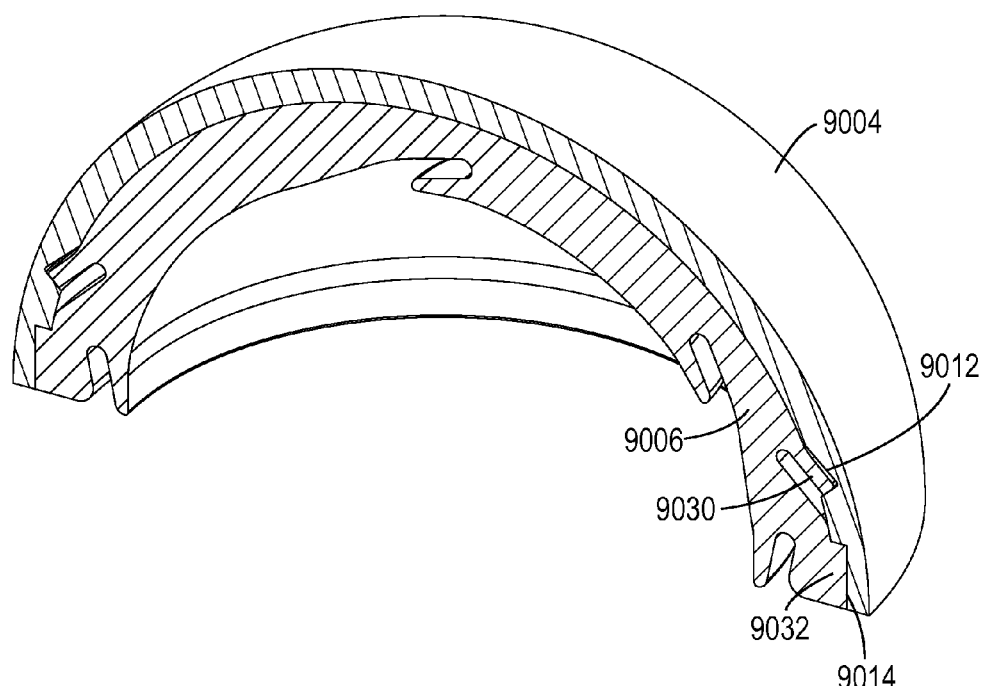
FIG. 73 is a perspective cross-sectional view of the prosthetic joint of FIGS. 72.
Figure 74:
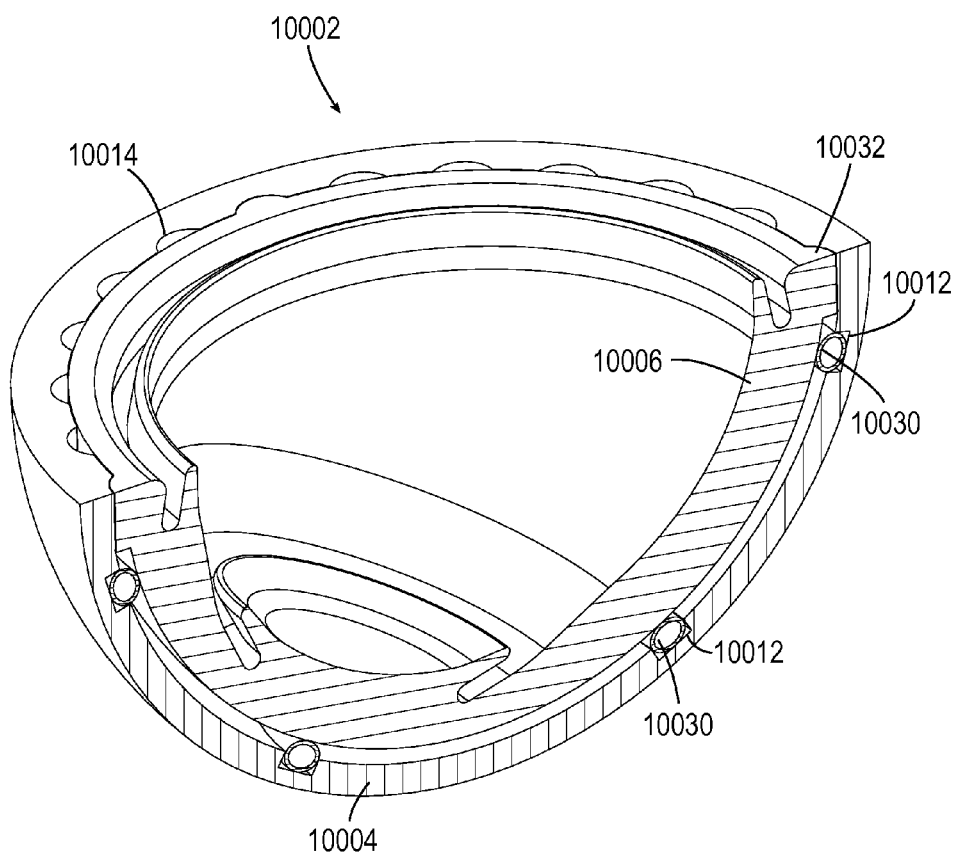
FIG. 74 is a perspective cross-sectional view of a prosthetic joint.

The features described above (that is, the indexing feature, the retention feature, or the resilient spacer) may be incorporated individually into a prosthetic joint member, or they may be applied to a joint member in any combination. For example, FIGS. 72 and 73 depict a prosthetic joint member 9002 similar in construction and function to the prosthetic joint member 2002 described above and having both indexing and retention features. The prosthetic joint member 9002 includes a cup 9004 and an insert 9006. The cup 9004 includes first indexing features 9014 and the insert 9006 includes second indexing features 9032. The cup 9002 also includes a retention groove 9012 and the insert 9006 includes retention tabs 9030. As another example, FIG. 74 depicts a prosthetic joint member 10002 similar in construction and function to the prosthetic joint member 7002 described above and having both resilient spacers and an indexing feature. The prosthetic joint member 10002 includes a cup 10004 and an insert 10006. The cup 10004 includes first indexing features 10014 and the insert 10006 includes second indexing features 10032. The cup 10012 also includes spacer grooves 10012 that receive resilient spacer rings 10030. It is also noted that, the flange of the joint members described above need not be circular, elliptical, or another symmetrical shape in plan view, and need not lie in a single plane. Plan view shapes such as oval, elliptical, and shapes formed from one or more splines is possible. One or more of the flanges may include an open perimeter. Furthermore, the sizing of the flanges and the contact rims relative to the expected loads applied thereto and considering fatigue considerations may be determined as described above for the similar flanges of the prosthetic joint 1000.

As noted above, known coatings such as titanium nitride, chrome plating, carbon thin films, and/or diamond-like carbon coatings may be used to impart wear resistance or augment the wear resistance of any of the contact surfaces and/or contact rims described above. To the same end, it may be desirable to surface treat either or both interfaces of any of the above-described implants or joints with a laser, shot peen, burnishing, or water shock process, to impart residual compressive stresses and reduce wear. The benefit could be as much from surface annealing and microstructure and microfracture elimination as smoothing itself.

The foregoing has described prosthetic joints with wear-resistant properties and conformal geometries. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

What is claimed is:

1. A prosthetic joint member comprising:
a concave cup with an outer surface that is bone-implantable, the cup including a first indexing feature;
a concave insert disposed inside the cup, the insert comprising a rigid material and including a concave interior defining a nominal surface, the interior including an elastically deformable cantilevered flange defined by an undercut in the insert, the flange defining a wear-resistant first contact surface which protrudes inward relative to the nominal surface and into the concave interior, the insert including a second indexing feature; and
wherein the first and second indexing features engage each other so as to retain the insert in a fixed angular orientation relative to the cup.

2. The prosthetic joint member of claim 1 wherein the first flange is asymmetric relative to a balanced centroidal axis of the prosthetic joint member.

3. The prosthetic joint member of claim 1 wherein the first indexing feature comprises a ring of notches or grooves.

4. The prosthetic joint member of claim 3 wherein the second indexing feature comprises one or more ribs complementary to the notches or grooves.

5. The prosthetic joint member of claim 1, wherein:
the cup includes a first retention feature;
the insert includes a second retention feature; and the first and second retention features engage each other to secure the cup and insert together.

6. The prosthetic joint member of claim 5, wherein the first retention feature is a groove and the second retention feature is a tab.

7. The prosthetic joint member of claim 5, wherein the first and second retention feature comprise complementary detent elements.

8. The prosthetic joint member of claim 6 wherein the tab and groove have cooperating shapes formed such that, after initial engagement of the tab with the groove, additional movement of the insert towards the cup will cause the tab to spring outward while remaining engaged with the groove.

9. The prosthetic joint member of claim 1 where the insert is resiliently suspended relative to the cup.

10. The prosthetic joint member of claim 1 wherein a compliant nonmetallic spacer is disposed between the cup and the insert.

11. The prosthetic joint member of claim 1 wherein the cup includes a step and the insert includes a lip which bears against the step, such that a clearance is present between the cup and the insert.

12. The prosthetic joint member of claim 1 wherein at least one elastically-deflectable spacer ring is disposed between the cup and the insert.

13. The prosthetic joint member of claim 12 wherein the spacer ring is received in a groove in the cup.

14. The prosthetic joint member of claim 1 wherein the flange has a plan view shape which is noncircular.

15. The prosthetic joint member of claim 1 wherein the flange has an open perimeter.

16. A prosthetic joint including the joint member of claim 1 and a convex member comprising a rigid material with a wear-resistant, convex contact surface received in the insert, where the first contact surface bears directly against the convex contact surface of the convex member, so as to transfer axial and lateral loads between the joint member and the convex member, while allowing pivoting motion between the joint member and the convex member.

17. The prosthetic joint of claim 16, where the contact surfaces are ceramic, metallic, or a combination thereof.

18. The prosthetic joint of claim 16, where the flange is sized so as to permit elastic deflection of the flange while limiting stresses in the flange to less than the endurance limit of the material, when a predetermined external load is applied to the joint.

* * * * *

UNITED STATES PATENT AND TRADEMARK OFFICE
CERTIFICATE OF CORRECTION

PATENT NO. : 8,308,812 B2
APPLICATION NO. : 13/342584
DATED : November 13, 2012
INVENTOR(S) : Franz W. Kellar et al.

Page 1 of 1

It is certified that error appears in the above-identified patent and that said Letters Patent is hereby corrected as shown below:

IN THE SPECIFICATIONS:
Column 2, line 61, delete "and".
Column 2, line 63, change "." to -- ; --.
Column 13, line 64, delete "A".

IN THE CLAIMS:
Column 26, Claim 2, line 57, delete "first".

Signed and Sealed this
Twelfth Day of March, 2013

Teresa Stanek Rea
*Acting Director of the United States Patent and Trademark Office*